US012676220B2

(12) United States Patent
Kasinathan et al.

(10) Patent No.: US 12,676,220 B2
(45) Date of Patent: Jul. 7, 2026

(54) METHODS, SYSTEMS, ARTICLES OF MANUFACTURE, AND APPARATUS TO REMOTELY MEASURE BIOLOGICAL RESPONSE DATA

(71) Applicant: Nielsen Consumer LLC, Chicago, IL (US)

(72) Inventors: Karthik Kasinathan, Oakland, CA (US); Avgusta Shestyuk, El Cerrito, CA (US)

(73) Assignee: Nielsen Consumer LLC, Chicago, IL (US)

( * ) Notice: Subject to any disclaimer, the term of this patent is extended or adjusted under 35 U.S.C. 154(b) by 0 days.

(21) Appl. No.: 18/575,730

(22) PCT Filed: Oct. 13, 2023

(86) PCT No.: PCT/US2023/076896
§ 371 (c)(1),
(2) Date: Dec. 29, 2023

(87) PCT Pub. No.: WO2024/081920
PCT Pub. Date: Apr. 18, 2024

(65) Prior Publication Data
US 2025/0246279 A1 Jul. 31, 2025

Related U.S. Application Data

(60) Provisional application No. 63/416,214, filed on Oct. 14, 2022.

(51) Int. Cl.
*G16H 10/20* (2018.01)
*G16H 15/00* (2018.01)
*G16H 50/70* (2018.01)

(52) U.S. Cl.
CPC ............. *G16H 15/00* (2018.01); *G16H 10/20* (2018.01); *G16H 50/70* (2018.01)

(58) Field of Classification Search
CPC ........ G16H 15/00; G16H 10/20; G16H 50/70; G16H 40/40; G16H 40/63; G16H 40/67;
(Continued)

(56) References Cited

U.S. PATENT DOCUMENTS 11,366,517 B2 * 6/2022 Alcaide .............. G02B 27/0093
11,877,856 B1 * 1/2024 Bibian ................... A61B 5/374
(Continued)

FOREIGN PATENT DOCUMENTS

WO 2012136599 A1 10/2012

OTHER PUBLICATIONS

International Searching Authority, "Written Opinion of the International Searching Authority," issued in connection with PCT Patent Application No. PCT/US2023/076896, mailed on Feb. 13, 2024, 5 pages.
(Continued)

*Primary Examiner* — Chad A Newton
(74) *Attorney, Agent, or Firm* — Hanley, Flight & Zimmerman, LLC

(57) ABSTRACT

Systems, apparatus, articles of manufacture, and methods are disclosed to remotely measure biological response data. An example apparatus includes interface circuitry; machine readable instructions; and programmable circuitry to at least one of instantiate or execute the machine readable instructions to generate a study based on one or more target modalities; transmit the study to electronic devices corresponding to study participants; obtain response data corresponding to the study; and aggregate the response data across the participants and across the modalities.

15 Claims, 19 Drawing Sheets

(58) Field of Classification Search
CPC .......... G06Q 30/0202; G06Q 30/0203; G06Q
30/0242; G06Q 30/0201
See application file for complete search history.

(56) References Cited

U.S. PATENT DOCUMENTS

| | | | |
|---|---|---|---|
| 2009/0030303 A1* | 1/2009 | Pradeep | G06Q 30/00 |
| | | | 600/411 |
| 2012/0259240 A1 | 10/2012 | Llewellynn et al. | |
| 2013/0331729 A1 | 12/2013 | De Lemos et al. | |
| 2018/0315063 A1 | 11/2018 | Cheesman | |
| 2021/0090097 A1* | 3/2021 | Froman | H04L 51/02 |

OTHER PUBLICATIONS

International Searching Authority, "International Search Report," issued in connection with PCT Patent Application No. PCT/US2023/076896, mailed on Feb. 13, 2024, 3 pages.

\* cited by examiner

900

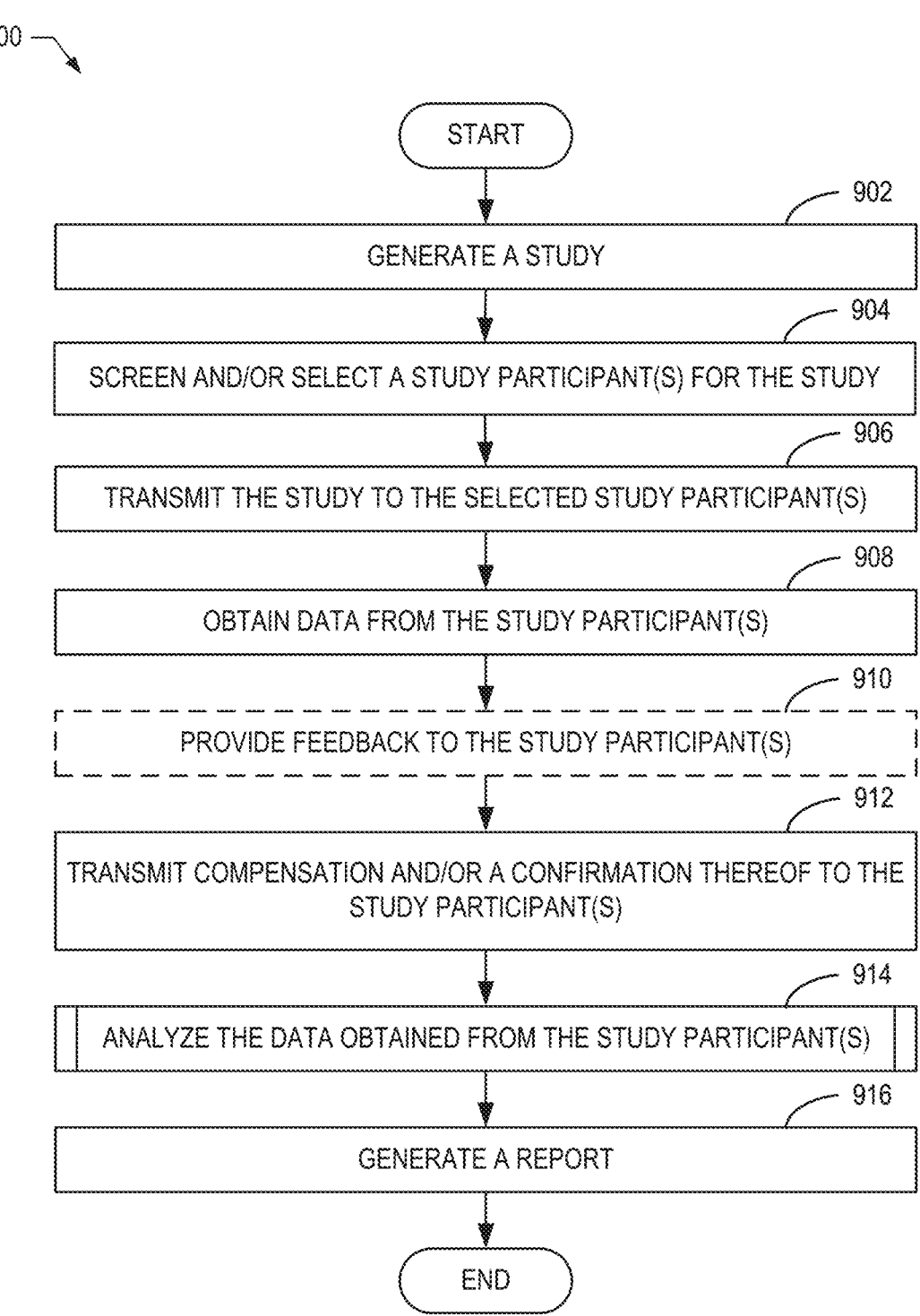

START

902

GENERATE A STUDY

904

SCREEN AND/OR SELECT A STUDY PARTICIPANT(S) FOR THE STUDY

906

TRANSMIT THE STUDY TO THE SELECTED STUDY PARTICIPANT(S)

908

OBTAIN DATA FROM THE STUDY PARTICIPANT(S)

910

PROVIDE FEEDBACK TO THE STUDY PARTICIPANT(S)

912

TRANSMIT COMPENSATION AND/OR A CONFIRMATION THEREOF TO THE STUDY PARTICIPANT(S)

914

ANALYZE THE DATA OBTAINED FROM THE STUDY PARTICIPANT(S)

916

GENERATE A REPORT

END

Figure 11:
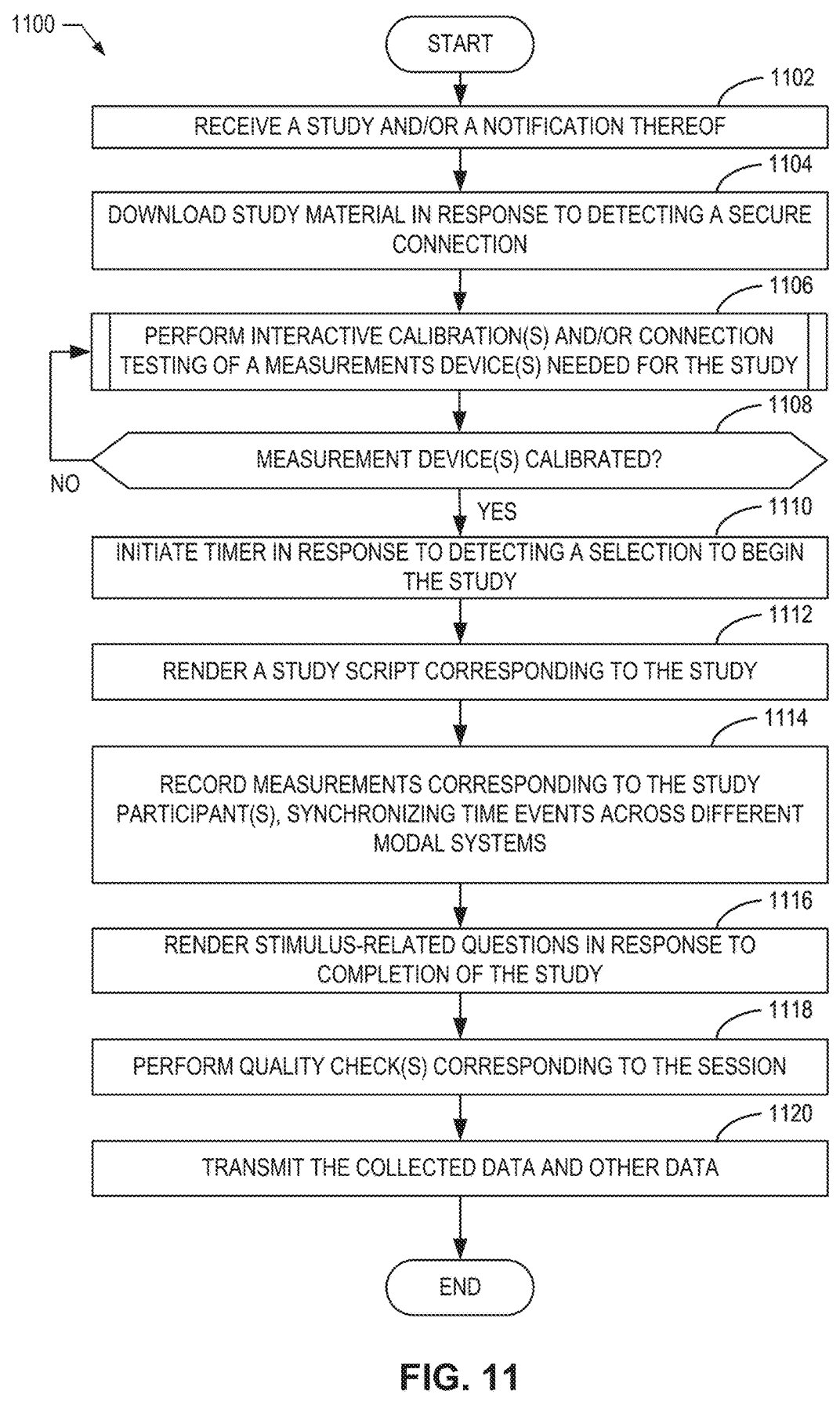

START

— 1102

RECEIVE A STUDY AND/OR A NOTIFICATION THEREOF

— 1104

DOWNLOAD STUDY MATERIAL IN RESPONSE TO DETECTING A SECURE CONNECTION

— 1106

PERFORM INTERACTIVE CALIBRATION(S) AND/OR CONNECTION TESTING OF A MEASUREMENTS DEVICE(S) NEEDED FOR THE STUDY

— 1108

MEASUREMENT DEVICE(S) CALIBRATED?

NO

YES

— 1110

INITIATE TIMER IN RESPONSE TO DETECTING A SELECTION TO BEGIN THE STUDY

— 1112

RENDER A STUDY SCRIPT CORRESPONDING TO THE STUDY

— 1114

RECORD MEASUREMENTS CORRESPONDING TO THE STUDY PARTICIPANT(S), SYNCHRONIZING TIME EVENTS ACROSS DIFFERENT MODAL SYSTEMS

— 1116

RENDER STIMULUS-RELATED QUESTIONS IN RESPONSE TO COMPLETION OF THE STUDY

— 1118

PERFORM QUALITY CHECK(S) CORRESPONDING TO THE SESSION

— 1120

TRANSMIT THE COLLECTED DATA AND OTHER DATA

END

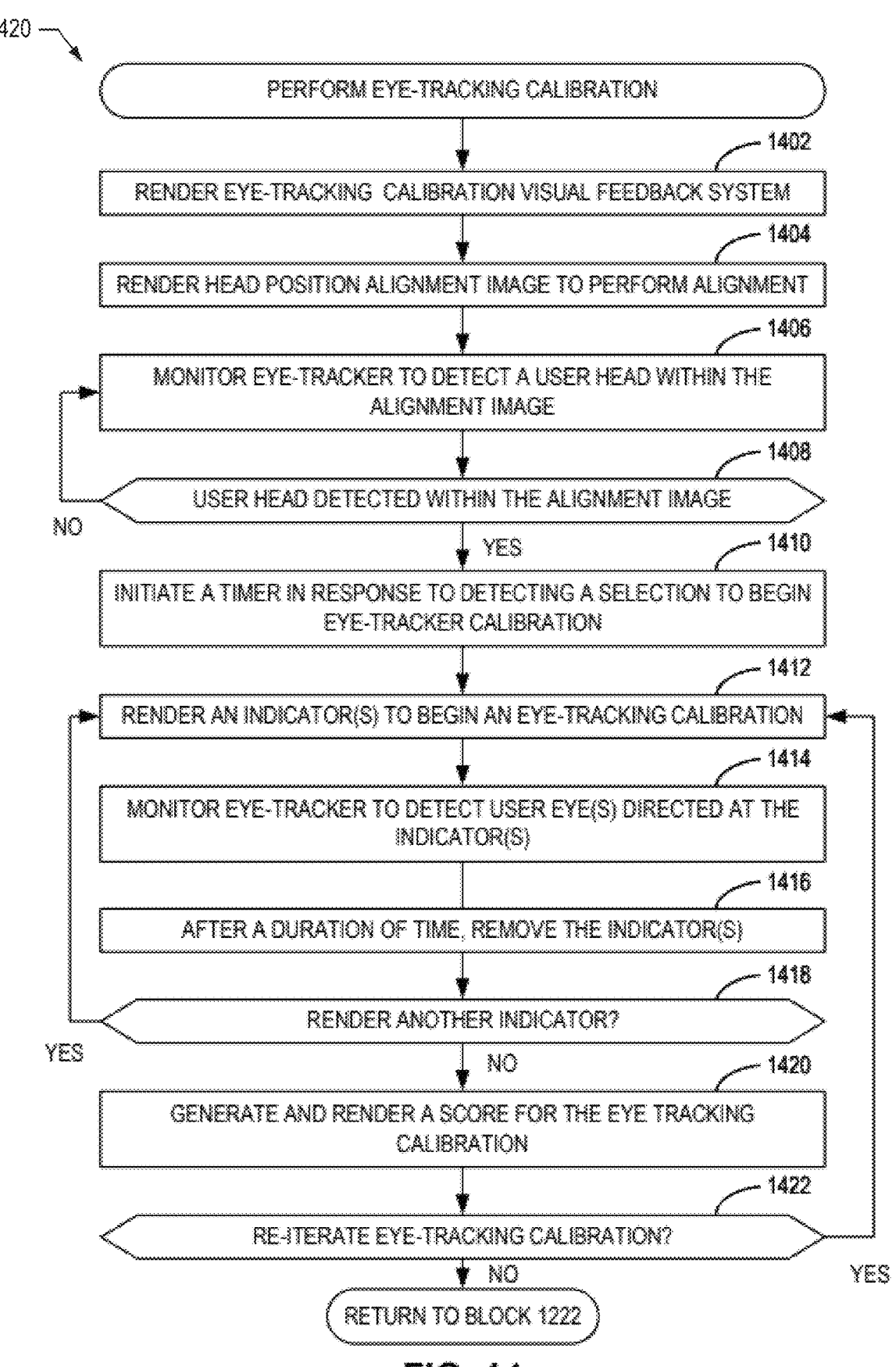

PERFORM EYE-TRACKING CALIBRATION

RENDER EYE-TRACKING CALIBRATION VISUAL FEEDBACK SYSTEM — 1402

RENDER HEAD POSITION ALIGNMENT IMAGE TO PERFORM ALIGNMENT — 1404

MONITOR EYE-TRACKER TO DETECT A USER HEAD WITHIN THE ALIGNMENT IMAGE — 1406

USER HEAD DETECTED WITHIN THE ALIGNMENT IMAGE — 1408

NO

INITIATE A TIMER IN RESPONSE TO DETECTING A SELECTION TO BEGIN EYE-TRACKER CALIBRATION — 1410

YES

RENDER AN INDICATOR(S) TO BEGIN AN EYE-TRACKING CALIBRATION — 1412

MONITOR EYE-TRACKER TO DETECT USER EYE(S) DIRECTED AT THE INDICATOR(S) — 1414

AFTER A DURATION OF TIME, REMOVE THE INDICATOR(S) — 1416

RENDER ANOTHER INDICATOR? — 1418

YES

GENERATE AND RENDER A SCORE FOR THE EYE TRACKING CALIBRATION — 1420

NO

RE-ITERATE EYE-TRACKING CALIBRATION? — 1422

NO     YES

RETURN TO BLOCK 1222

FIG. 14

METHODS, SYSTEMS, ARTICLES OF MANUFACTURE, AND APPARATUS TO REMOTELY MEASURE BIOLOGICAL RESPONSE DATA

RELATED APPLICATION

This patent arises from the national stage of International Application No. PCT/US23/76896, which was filed on Oct. 13, 2023, which claims the benefit of U.S. Provisional Patent Application No. 63/416,214, which was filed on Oct. 14, 2022. International Application No. PCT/US23/76896 and U.S. Provisional Patent Application No. 63/416,214 are hereby incorporated herein by reference in their entireties. Priority to International Application No. PCT/US23/76896 and U.S. Provisional Patent Application No. 63/416,214 is hereby claimed.

FIELD OF THE DISCLOSURE

This disclosure relates generally to the technical field of market research and, more particularly, to methods, systems, articles of manufacture, and apparatus to remotely measure biological response data.

BACKGROUND

Market research entities aim to provide market participants (e.g., manufacturers, retailers, etc.) with actionable information that brands use to grow their businesses. For example, a market research entity can help brand owners understand an impact of a marketing material on a consumer by directly measuring emotional, memory, and attention activity in the brain of the consumer. To do so, the market research entity may collect neurological and/or physiological response data such as central nervous system, autonomic nervous system, and effector system measurements while the consumer engages with the marketing material. The market research entity may analyze the response data along with survey based data to generate actionable insights.

BRIEF DESCRIPTION OF THE DRAWINGS

FIGS. 9-14 are flowcharts representative of example machine readable instructions and/or example operations that may be executed, instantiated, and/or performed by example programmable circuitry to implement the data collection system 100 of FIGS. 1-7.

In general, the same reference numbers will be used throughout the drawing(s) and accompanying written description to refer to the same or like parts. The figures are not necessarily to scale.

DETAILED DESCRIPTION

Figure 1:
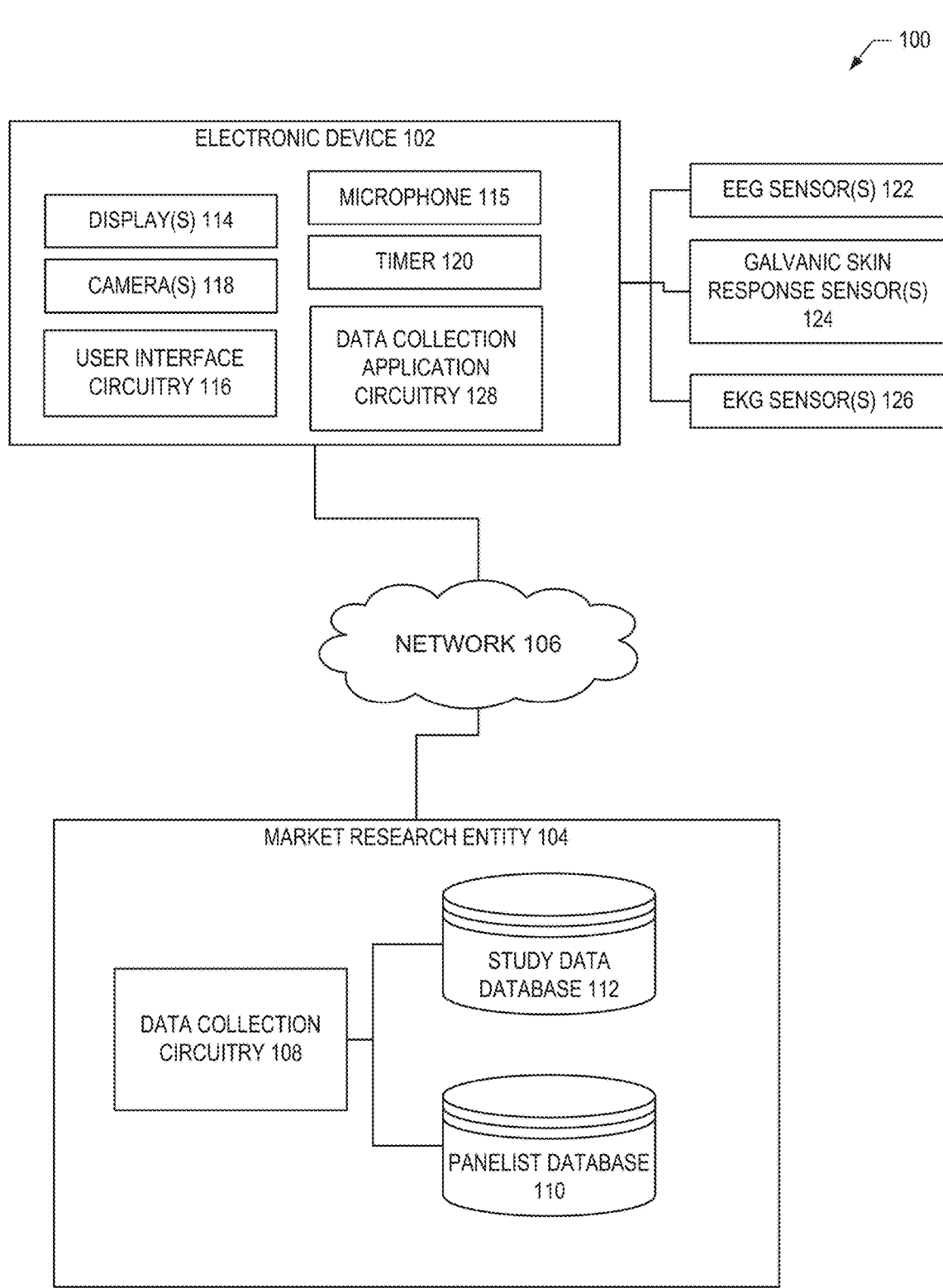
FIG. 1 is a block diagram of an example environment in which an example data collection system operates to facilitate remote response data collection in accordance with teachings of this disclosure.

Data collection systems for evaluating marketing materials such as, but not limited to, products, packages, and/or advertisements involve, for example, monitoring and/or surveying individuals exposed to the materials. Some systems involve the use of sensors and/or other data collection devices to measure electrical activity of a study participant(s) during the exposure to the marketing material. Traditional data collection systems involve the use of such data collection devices in a brick-and-mortar testing location, such as a central testing location. However, the traditional data collection systems pose several limitations. For example, such data collection systems often require human supervision.

Some nervous system measurement devices used in traditional data collection systems include multiple, separate data collection devices, which may be connected through external ports to synchronize time events. In some such systems, trained technicians are required to set up, calibrate, initiate and/or monitor a data collection process (e.g., a session). The traditional data collection systems often rely on one or more trained experts for data collection. Such a data collection system is costly, inefficient, and causes difficulties for participants who desire to participate in a study at a time during which the trained experts are unavailable. For example, central testing locations may only operate during specific times and/or days, limiting an ability of potential participants who have other obligations (e.g., work, childcare, etc.) during those hours of operating.

The traditional data collections systems can also limit an ability of certain demographic groups to participate in the study. For example, due to limited geographic presence of testing locations, rural participants may have difficulty attending a study. In some examples, potential participants may be limited based on conditions of the participant, such as health conditions, familial obligations, etc. These limitations became more evident during the COVID-19 pandemic, which effectively shut down all in-person testing methods. In some cases, the effects remain, such as for potential participants who may be immunocompromised and continue to practice social distancing or isolation.

Further, an amount of data collected in such data collections systems is limited by an availability of such trained technicians. If trained technicians are unavailable, the market research entity may be unable to collect biological data, limiting the market research entity's ability to generate insights and, as a result, the market research entity's profits. Examples disclosed herein provide an innovative data collection system that is efficient, accessible, and convenient. Examples disclosed herein include an integrated platform to collect biological data from a participant(s) at a remote location(s) (e.g., at home, etc.) at a time that is convenient to the participant.

Disclosed herein are example methods, systems, articles of manufacture, and apparatus for collecting and analyzing response data measured at a remote location. Examples disclosed herein implement an example data collection system having an integrated platform that enables collection and analysis of biological data including neurological, physiological, and/or behavioral data from participants in different locations. As disclosed herein, a participant (e.g., a study participant) is a person who is an eligible consumer that agrees to engage with example data collection systems disclosed herein. In the following description, the terms user, participant, subject, patient, panelist, etc. are used interchangeably to refer to a participant and/or a potential participant that uses an electronic device in accordance with teachings of this disclosure. As opposed to the traditional data collection techniques that are performed at a testing location, example response data collection systems disclosed herein easily facilitate studies that include participants distributed across geographic regions (e.g., across countries, states, etc., urban, rural, etc.). In some examples, any eligible consumer with access to a network (e.g., internet) connection can potentially qualify to participate in a study.

As disclosed herein, response data refers to measurements collected as the participant(s) engages with a marketing materials that can be used to determine the participant's response to the marketing material(s). For example, response data can include (but is not limited to) neuro-physiological response measurements such as central nervous system (e.g., EEG, etc.), autonomic nervous system (e.g., galvanic skin response data, EKG response data, etc.), effector measurements (e.g., facial encoding data, eye-tracking data, reaction time, etc.), as well as survey-based response data, and/or other data collected during a study session. Though the examples disclosed herein are directed towards studies of marketing materials, teachings of this disclosure can apply to other stimuli or media of any type including, for example, entertainment, educational materials, informational materials, etc. providing a method and a system for the neuro-physiological and neuro-behavioral response based measurement of audience response and resonance to attributes of marketing, advertising and other audio/visual/tactile/olfactory stimulus including but not limited to communication, concept, experience, message, images, audio, pricing, packaging, etc.

Certain example data collection systems include an onboarding process for a participant(s) that includes one or more training sessions. In some examples, a participant completes an initial training session before receiving data collection devices from a market research entity to gain an understanding of a session before agreeing to participate. However, in other examples, the participant can obtain the data collection devices prior to performing a training session. In some examples, the participant(s) completes one or more training sessions before being onboarded to the data collection system as a participant. In some examples, the one or more training session(s) systemically guide a potential participant(s) through a calibration(s) of a data collection device(s), the application for completing a study, trouble shooting, and/or an example study session(s).

Certain example data collection systems disclosed herein generate a study at a first location. For example, the first location can be a facility (e.g., a central facility, etc.) associated with an entity, such as a market research entity. In some examples, a central server associated with the central facility may be used to generate the study, select participants for the study, and/or analyze data collected from the selected participants. The study may include instructions (e.g., for completing the study), definitions, goals, and/or other information corresponding to one or more marketing materials for which the market research entity desires to gain insights. The marketing material(s) can include, but is not limited to, a video communication (e.g., animatics, rough cuts, finish copies, etc.); a package design; a physical pack (e.g., having a shape, weight, texture, etc.); a product; an ad strategy and/or brand position (e.g., manifesto, idea, etc.); a circular, point of sale (POS) presentation, and/or key visual; a website, product page, etc.; brand essence and/or brand cue(s); etc. In some examples, the central facility can transmit a data packet for the study (e.g., a study data packet, etc.) to the selected participants. The data packet can include, but is not limited to, a market material(s); a series of stimuli (e.g., a video(s), an image(s), entertainment stimulus material, etc.); response data to be collected; instructions to setup, connect, and/or calibrate a participant's data connection(s); a stimulus-related survey(s) (e.g., questionnaire, series of questions, etc.); a behavioral feedback segment; and/or other information that enables the participant(s) to complete the study.

Example data collection systems disclosed herein collect response data for the study at a second location(s), which is a location in which a participant(s) performs the study. Certain examples collect response data for the study at a plurality of locations, wherein the locations correspond to respective participants of the study. Example data collection systems disclosed herein enable monitoring of participants during a session in a location that is outside the central facility using an electronic device. That is, example data collection systems disclosed herein enable collection and/or monitoring of neuro-response, physiological response, and/or survey based data in a remote location. As disclosed herein, a session refers to a duration in which a participant engages in a study.

Examples of the central nervous system measurements collected by disclosed response data collection systems disclosed herein include, but are not limited to, electroencephalography (EEG), eye-tracking, pupil dilation, facial emotion encoding, response time, galvanic skin response, and electrocardiograms (EKG). EEG involves measuring and recording electrical activity resulting from neural processes associated with different portions of the brain. Eye-tracking data can be used to measure eye movements and convert them into points of gaze on a display (e.g., a personal computer screen, a monitor, etc.). Facial emotion encoding measures physical facial movements and converts them into identifications or labels of expressed emotions. Response time measures a time to respond to a stimulus of interest. Galvanic skin response measures arousal through changes in sweat gland activity. An EKG measures arousal through electrical activity from the heart. Example response data collection systems disclosed herein can collect additional or alternative central nervous system measurements in other examples, such as blink rate, breathing, motion, muscle movement, and/or any other response correlated with changes in emotion of a viewer of a marketing material. As disclosed herein, a modality refers to a type of response data, such as EEG, eye-tracking, facial encoding, galvanic response, timing, survey-based response data, etc.

Example data collection techniques disclosed herein blend multiple modes of neural signatures and/or data collection devices for each participant to assess the effectiveness of a marketing material(s). Certain disclosed examples pre-process study data for the participant prior to analysis of the study data. By enabling remote collection of neuro-response data and/or physiological response data, certain examples disclosed herein enable an increase in participants who return for additional studies. In some such examples, data collection systems disclosed herein analyze the individual study data to generate personalized data by, for example, identifying signatures in the study data that are unique to the participant. In some examples, the personalization component increases an efficacy of measures and/or an effectiveness of a study session by reducing or otherwise eliminating certain parts of the session. For example, the personalized data may include calibration settings in a session that can be applied to another session, removing the need to re-calibrate the data collection device(s). In some examples, the personalized data can be used across sessions to ensure a participant that agreed to participate in the study is the same person from which the study data is collected. The personalized data, however, can be used for other tasks, such as future research, baseline measurements, etc.

Disclosed examples aggregate the measured neurophysiological and behavior responses across participants to provide a robust measure of engagement to generate insights and predict actionable behavior. Disclosed examples can blend multiple datasets, and blended manifestations of multi-modal responses, across multiple datasets, individuals and modalities, to reveal and validate the elicited measures of preference and resonance to stimulus and stimulus attributes.

Example methods, systems, articles of manufacture, and apparatus of the present disclosure will be described in the context of particular types of data such as, for example, central nervous system, autonomic nervous system, and effector data. However, it is noted that the techniques and mechanisms of the present disclosure can be applied to different types of data. While example data collection techniques disclosed herein are discussed in terms of market research, disclosed examples can be applied to other areas. For example, example data collection systems disclosed herein can be used for medical applications, such as remote data collection for patients, clinical applications, active and/or passive monitoring of people (e.g., of a panelist, a consumer, etc.), etc.

FIG. 1 is a block diagram of an example environment including an example data collection system 100 to collect and analyze response data and/or other data corresponding to a participant(s) (e.g., study participant) that is measured at a remote location. The data collection system 100 of FIG.

Figure 2:
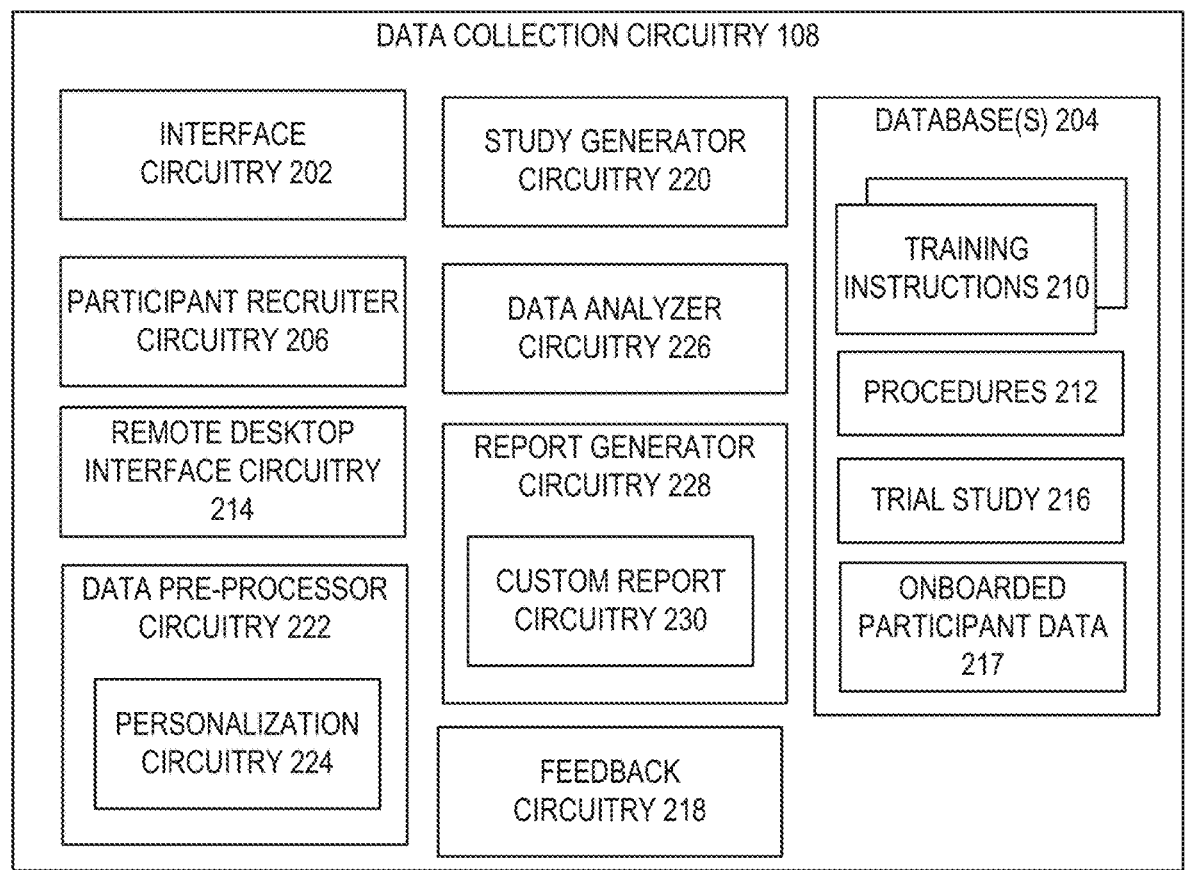
FIG. 2 is a block diagram of the example data collection platform of FIG. 1 structured in accordance with teachings of this disclosure.
Figure 3:
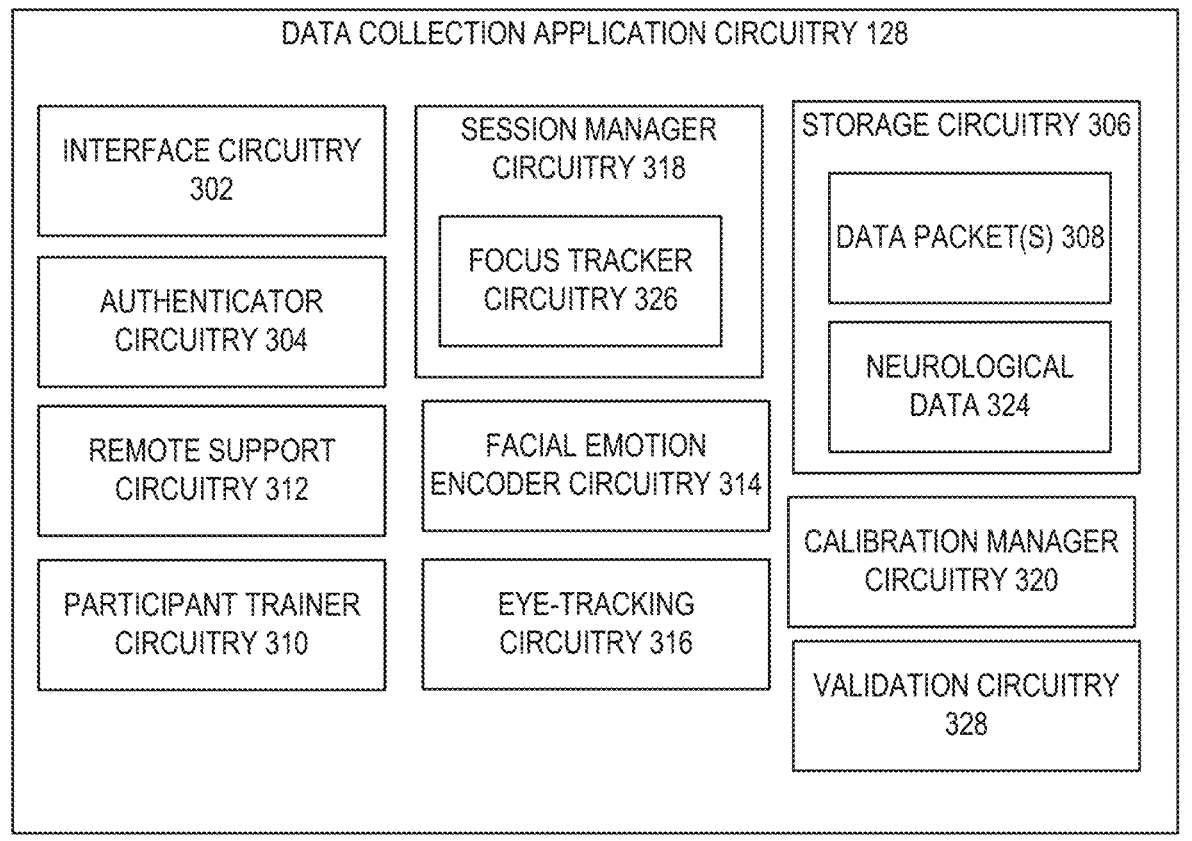
FIG. 3 is a block diagram of the example data collection application circuitry of FIG. 1 structured in accordance with teachings of this disclosure.
Figure 6:
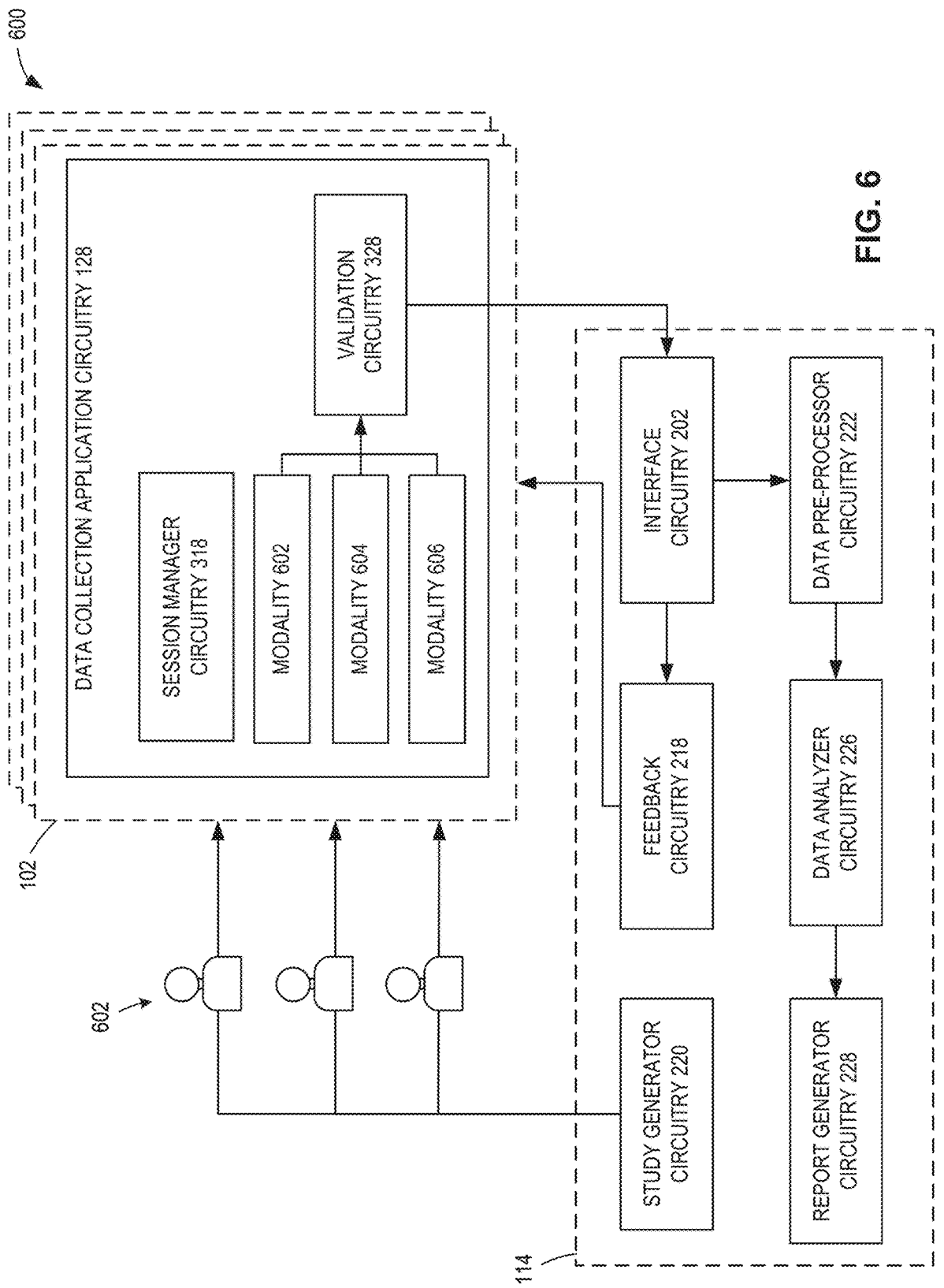
FIG. 6 is a block diagram of an example implementation of the data collection system of FIGS. 1-3 in accordance with teachings of this disclosure.

1 includes an example electronic device(s) 102, which is communicatively coupled to an example market research entity 104 via an example network 106. The electronic device 102 is an electronic device associated with a panelist (e.g., a panel member, a market cooperator, an eligible consumer, etc.) that may agree to be a participant. The electronic device 102 can be, for example, a personal computing (PC) device such as a laptop, a smartphone, an electronic tablet, a watch, a headset, virtual reality goggles, a smart television, a hybrid or convertible PC, etc. An example implementation of the data collection system 100 is also depicted in FIGS. 2, 3, and 6.

The market research entity 104 can be, for example, an entity that generates insights for use by market participants based on neurological, physiological, and/or behavioral data collected from the participant(s). In some examples, the market research entity 104 is implemented by one or more servers. For example, the market research entity 104 can be a physical processing center including servers. In some examples, at least some functionality of the market research entity 104 is implemented via an example cloud and/or Edge network (e.g., AWS®, etc.). In some examples, the market research entity 104 is absent. For example, the functionality of the market research entity 104 may be implemented by any suitable device or combination of devices (e.g., electronic device 102, etc.).

In the illustrated example of FIG. 1, the network 106 is the Internet. However, the example network 106 may be implemented using any other network over which data can be transferred. The example network 106 may be implemented using any suitable wired and/or wireless network(s) including, for example, one or more data buses, one or more Local Area Networks (LANs), one or more wireless LANs, one or more cellular networks, one or more private networks, one or more public networks, among others. In additional or alternative examples, the network 106 is an enterprise network (e.g., within businesses, corporations, etc.), a home network, among others.

The market research entity 104 includes example data collection platform implemented by example data collection circuitry 108 to obtain, aggregate, and/or analyze data collected from a participant(s) corresponding to the electronic device(s) 102. The example data collection circuitry 108 of FIG. 1 facilitates the development of protocols and/or study designs to generate a study. In some examples, the data collection circuitry 108 enables a selection or subset of available neuro-physiological data to be collected for a particular study. An example implementation of the data collection circuitry 108 is also depicted in FIG. 2.

While example data collection circuitry 108 as disclosed herein is discussed in terms of response data collection corresponding to a study, examples disclosed herein are not limited thereto. Rather, the data collection circuitry 108 can be applied in additional or alternative application such as (but not limited to) monitoring of an individual(s) and/or a group of individuals (e.g., a household, a family, etc.). For example, the example data collection circuitry 108 can be utilized for time-based monitoring (e.g., duration(s) of time, etc.), task-based monitoring, passive monitoring, etc. It is understood that the example data collection circuitry 108 can be utilized for any application in which response data associated with the target individual(s) and/or the group of individuals.

In some examples, the data collection circuitry 108 enables screening (e.g., vetting, assessing, etc.) individuals to find potential participants that qualify for a study based on information associated with the individuals. In some examples, the potential participant(s) is a panel member associated with the market research entity 104 that agrees to participate in a screening process. In some examples, the data collection circuitry 108 enables selection of participants that qualify for a study based on information associated with the potential participants.

In some examples, the example market research entity 104 includes an example panelist database 110, which is structured to store data associated with panelists. For example, the panelist database 110 can include information for different people who have agreed to provide purchase data and/or other information (e.g., demographic, household information, etc.) to the market research entity 104. The panelist database 110 may include different information associated with the panelist(s), such as demographics, purchase preferences, consumption history, etc. In some examples, the panelist database 110 includes biometric data, such as (but not limited to) facial recognition data, fingerprint data, etc., for one or more panelists. In some such examples, the panelist database 110 only includes biometric data for consumers who agree to utilize biometric authentication (e.g., to log into the data collection circuitry 108, the data collection application circuitry described below, etc.). In some examples, the panelist database 110 includes indices that indicate panelists that have already agreed to participate in one or more studies. In some examples, the data collection circuitry 108 searches the panelist database 110 based on the study design and/or protocols to identify potential participants that may qualify for the study.

The example market research entity 104 includes an example study data database 112, which is structured to store response data, study data, and/or reports corresponding to the response data. For example, the study data database 112 may include neurological response data and/or physiological response data from participants that agreed to participate in a study. In some examples, the study data database 112 includes reports and/or insights generated based on the neurological response data and/or physiological response data from the participants. As disclosed herein, response data refers to individual response measurements gathered during a session. As disclosed herein, study data refers to response data associated with a study and uploaded to or otherwise communicated with the data collection circuitry 108.

The example panelist database 110 and/or the example study data database 112 of the illustrated example of FIG. 1 is implemented by any memor(ies), storage device(s) and/or storage disc(s) for storing data such as, for example, flash memory, magnetic media, optical media, etc. Furthermore, the data stored in the example panelist database 110 and/or the example study data database 112 may be in any data format such as, for example, binary data, comma delimited data, tab delimited data, structured query language (SQL) structures, image data, etc.

When the example data collection circuitry 108 has generated the study and/or selected a participant(s) to participate in the study, the data collection circuitry 108 can transmit the study to the electronic device(s) 102 associated with the selected participant(s). For example, the data collection circuitry 108 can transmit a data packet that contains a marketing material(s) or other stimulus for the study, instructions, and/or other information the participant may use to complete the study.

The electronic device 102 of FIG. 1 is communicatively coupled to an example display(s) 114 (e.g., via a wired and/or wireless connection), which may be any suitable display device to display data, such as a touchscreen display, a liquid crystal display (LCD), a projector, etc. In some examples, the display(s) 114 is physically attached to the electronic device 102, such as when the electronic device 102 is a laptop. In some examples, the display(s) 114 is communicatively coupled to the electronic device 102, such as when the electronic device 102 is a personal computing device that is coupled to a monitor. In some examples, the display(s) 114 allows a participant(s) to view and/or interact with study materials corresponding to the study. For example, the study may include a series of stimuli, tasks that require active response, image or word probes, and/or instructions. The participant(s) can view the stimuli, tasks, image or word probes, and/or the instructions via the display(s) 114.

The example electronic device 102 of FIG. 1 includes example microphone 115 and/or other audio sensor to sense audio. In some examples, the microphone 115 is an array of microphones. In some examples, the microphone 115 is utilized to detect noise in an environment surrounding the electronic device 102 (e.g., to identify noise interference that affects response data collected during a study). In some examples, the microphone includes an A/D converter. In some examples, the microphone(s) 115 implements means for recording audio.

The example electronic device 102 of FIG. 1 includes example user interface circuitry 116, which enables a user to interact with the electronic device 102. In some examples, the user interface circuitry 116 enables the electronic device 102 to obtain information from the user via an input device and provide information to the user via an output device, such as the display(s) 114.

The electronic device 102 includes an example camera(s) 118 and/or other image sensor(s) capable of capturing image data of the participant during a session. In some examples, the camera(s) 118 generates image data that can be used, for example, for eye-tracking, facial emotion encoding, facial recognition, etc. For example, the camera(s) 118 can be used to track eye movements of the participant relative to display 114 of the electronic device(s) 102. In some examples, the camera 118 can track pupil dilation of a participant. In some examples, the camera 118 can be used to track facial movements of the participant for identification of physical expressions of emotions. In some examples, the camera 118 can be used to identify the panelist (e.g., via facial recognition).

In the example of FIG. 1, the camera(s) 118 is carried by the electronic device 102 such that when the user faces the display 114 of the electronic device 102, the user is within a field of view of the camera(s) 118. For example, the camera(s) 118 can be carried by a bezel of the display 114. In some examples, the camera(s) 118 can be a separate component that is communicatively coupled to the electronic device 102 (e.g., a webcam coupled to the electronic device 102 via a wired and/or wireless connection). In some examples, the camera(s) 118 implements means for capturing image data.

The electronic device 102 includes an example clock or timer 120 to monitor time (e.g., a duration of time, a time at which an event occurs, etc.). In some examples, the timer 120 may monitor and/or identify a response time associated with a session. For example, the timer 120 may measure a duration of time during which a participant responds to a target stimulus. In some examples, the timer 120 monitors a time at which a sensor measurement is determined. In some examples, the timer 120 monitors time by identifying a time at which the measurement is sensed. In some examples, the timer 120 can be used to create timestamps that are to be associated with data measured during a study. In some examples, the timer 120 monitors time relative to a point in time. For example, the timer 120 may monitor a time at which a measurement is determined relative to a start of a study. In some examples, the timer 120 implements means for monitoring time.

The electronic device 102 is communicatively coupled to an example EEG sensor(s) 122, which is structured to measure electrical activity in a participant's brain. In particular, the EEG sensor(s) 122 is to measure electrical activity associated with post-synaptic currents (e.g., occurring in the milliseconds range). EEG involves measuring and recording electrical activity resulting from neural processes associated with different portions of the brain. EEG data is typically measured using a plurality of electrodes placed on the scalp of a person to measure voltage fluctuations resulting from this electrical activity within the neurons of the brain. EEG data provides a wealth of electrophysiological information with temporal and frequency resolution. In some examples, the EEG sensor(s) 122 implements means for measuring electrical activity of neurons of a brain. In some examples, the EEG sensor(s) 122 implements means for measuring a neuro-physiological response.

The electronic device 102 is communicatively coupled to an example galvanic skin response sensor(s) 124, which is structured to detect changes in electrical (e.g., ionic) activity resulting from changes in sweat gland activity. For example, the galvanic skin response sensor(s) 124 can be used to measure participant stimulation through changes in sweat gland activity of the participant. In some examples, the galvanic skin response sensor(s) 124 implements means for measuring a change in electrical activity resulting from a change in sweat gland activity. In some examples, the galvanic skin response sensor(s) 124 implements means for measuring a neuro-physiological response.

The electronic device 102 is communicatively coupled to an example EKG (e.g., ECG) sensor(s) 126, which is structured to measure electrical activity from a heart of the participant(s). In some examples, the EKG sensor(s) 126 implements means for measuring electrical activity from a heart. In some examples, the EKG sensor(s) 126 implements means for measuring a neuro-physiological response.

In some examples, at least one of the example camera(s) 118, the example timer 120, the example EEG sensor(s) 122, the example galvanic skin response sensor(s) 124, and/or the example EKG sensor(s) 126 implement an example measurement device(s) (e.g., a data collection device(s), etc.). As disclosed herein, a data collection device(s) refers to one or more of the EEG sensor(s) 122, the galvanic skin response sensor(s) 124, the EKG sensor(s) 126, the camera, etc. In some examples, the electronic device(s) 102 includes or is otherwise communicatively coupled to one or more additional or alternatives sensors, such as an electrooculography (EOG) sensor, a blood oxygen sensor, etc.

The electronic device 102 includes example data collection application circuitry 128, which can implement an example data collection application, data collector, or other component that enables a participant(s) to participate in a session. In some examples, the data collection application circuitry 128 implements an application programming interface (API). In some examples, the data collection application circuitry 128 is implemented within a browser that executes a protocol to obtain the data collection application. In some examples, the data collection application circuitry 128 is instantiated by processor circuitry executing data collection application instructions and/or configured to perform operations such as those represented by the flowcharts of FIGS. 11-14. An example implementation of the data collection application circuitry 128 of the example electronic device 102 is discussed in further detail in relation to FIG. 3.

The example data collection application circuitry 128 a is discussed herein in terms of response data collection corresponding to a study. However, the data collection application circuitry 128 can be applied in additional or alternative applications in other examples. In some examples, the example data collection application circuitry 128 can be utilized for monitoring of an individual(s) and/or a group of individuals (e.g., a household, a family, etc.). For example, the data collection application circuitry 128 can be used to facilitate time-based monitoring, task-based monitoring, passive monitoring, etc. For example, the data collection application circuitry 128 can be utilized to facilitate monitoring of a panelist(s) while the panelist(s) performs a task, such watching television, browsing the Internet, interacting with smartphone apps, etc. In examples, the data collection application circuitry 128 can be used to enable passive monitoring of one or more panelist(s). It is understood that the example data collection application circuitry 128 can be utilized for different applications that use response data associated with the individual(s) and/or the group of individuals.

The data collection application circuitry 128 of FIG. 1 enables the collection of multiple nervous system modal measurements integrated from single device. In some examples, the data collection application circuitry 128 enables communication across connected hardware devices to provide a unified dashboard across various modalities. In some examples, the data collection application circuitry 128 synchronizes time events with precision (e.g., within 10 milliseconds) across multiple nervous system measurements.

FIG. 2 is a block diagram of an example implementation of the data collection circuitry 108 of FIG. 1 to obtain, process, and/or analyze neuro-response data, physiological response data, and/or other data corresponding to biological measurements of a participant(s) during a study session performed at a remote location. The data collection circuitry 108 of FIG. 2 may be instantiated (e.g., creating an instance of, bring into being for any length of time, materialize, implement, etc.) by programmable circuitry such as a Central Processor Unit (CPU) executing first instructions. Additionally or alternatively, the data collection circuitry 108 of FIG. 2 may be instantiated (e.g., creating an instance of, bring into being for any length of time, materialize, implement, etc.) by (i) an Application Specific Integrated Circuit (ASIC) and/or (ii) a Field Programmable Gate Array (FPGA) structured and/or configured in response to execution of second instructions to perform operations corresponding to the first instructions. It should be understood that some or all of the circuitry of FIG. 2 may, thus, be instantiated at the same or different times. Some or all of the circuitry of FIG. 2 may be instantiated, for example, in one or more threads executing concurrently on hardware and/or in series on hardware. Moreover, in some examples, some or all of the circuitry of FIG. 2 may be implemented by microprocessor circuitry executing instructions and/or FPGA circuitry performing operations to implement one or more virtual machines and/or containers.

The data collection circuitry 108 includes example interface circuitry 202, which is structured to facilitate communication (e.g., data transfer, etc.) between the data collection circuitry 108 (e.g., components thereof) and the example data collection application circuitry 128 of the electronic device(s) 102 (FIG. 1). In some examples, interface circuitry 202 facilitates communication between the data collection circuitry 108 and other components of the market research entity 104. In some examples, the interface circuitry 202 is instantiated by programmable circuitry executing interface instructions and/or configured to perform operations such as those represented by the flowchart(s) of FIGS. 9-10.

The data collection circuitry 108 includes an example database 204, which is structured to store data associated with the data collection circuitry 108. The database 204 of the illustrated example of FIG. 2 is implemented by any memor(ies), storage device(s) and/or storage disc(s) for storing data such as, for example, flash memory, magnetic media, optical media, etc. Furthermore, the data stored in the database 204 may be in any data format such as, for example, binary data, comma delimited data, tab delimited data, structured query language (SQL) structures, image data, etc.

The data collection circuitry 108 includes example participant recruiter circuitry 206, which is structured to recruit and/or identify potential participants for a study. In some examples, the participant recruiter circuitry 206 is instantiated by processor circuitry executing participant recruiter instructions and/or configured to perform operations such as those represented by the flowchart of FIG. 9. In some examples, the participant recruiter circuitry 206 identifies a potential participant(s) to take part in a specific study based on attributes of the potential participant(s). As disclosed herein, a potential participant is an interested panelist that has competed the onboarding process (described below). As disclosed herein, an interested panelist is a panelist that transmits an indication of interest to participate in a study but has not completed the onboarding process.

The attributes of the potential participant can include, but are not limited to, demographics, purchase preferences, consumption history, geographic data, and/or other information associated with the potential participant. In some examples, the participant recruiter circuitry 206 generates a survey including a series of survey questions that enable the participant recruiter circuitry 206 to determine a potential participant's qualification to participate in the study. The participant recruiter circuitry 206 may transmit the survey to potential participant's (e.g., via interface circuitry 202). In some examples, the participant recruiter circuitry 206 also transmits a notification (e.g., an email, a text message, an application alert, etc.) to the potential participant regarding the survey. The participant recruiter circuitry 206 can use survey responses received from the potential participants to select participants for the study.

The participant recruiter circuitry 206 of FIG. 2 identifies interested panelists that may be willing to undergo an onboarding process and/or to participate in a study. For example, the participant recruiter circuitry 206 may identify possible interested panelists from the example panelist database 110 of FIG. 1. The panelist database 110 may include a plurality of panel members and associated information, such as, for example, an email address, phone number, etc. The example participant recruiter circuitry 206 can send a message to one or more panelists from the panelist database 110 that requests a reply or other communication from interested panelist. In response to receiving a reply from an interested panelist, the example participant recruiter circuitry 206 can transmit an example consent form to the interested panelist. In some examples, the consent form includes a description of a study, data security protocols, etc. In some examples, the consent form can be omitted.

In some examples, in response to receiving an executed consent form from the interested panelist, the participant recruiter circuitry 206 transmits a data packet(s) to the interested panelist that allows the panelist to engage in an initial training session. In some examples, the initial training session is a first step in the onboarding process. In some examples, the initial training session data packet includes example training instruction(s) 210, example procedure(s) 212, and/or a link to the training instruction(s) 210 and/or the procedure(s) 212. The initial training session is structured to provide the interest panelist(s) with a description of and/or obligations for a typical study session. The training instruction(s) 210 may include a walk-through of data collection devices (e.g., the EEG sensor(s) 122, galvanic response sensor(s) 124, EKG sensor(s) 126, etc.) and/or other devices that may be used during a study. The procedure(s) 212 may include methods and instructions corresponding to the study, such as how to care for the equipment, how to log into the study, how to connect the equipment during the study, etc. It is understood that the initial training session may be omitted from the onboarding process.

In some examples, upon a detection that the interested panelist completed the initial training session, the participant recruiter circuitry 206 transmits a link and/data packet(s) to the interested panelist that allows the interested panelist to schedule an intermediate training session. In some examples, the intermediate training session can be completed with a trained technician(s) (e.g., a one-on-one training session, group training session, etc.). In some examples, the interested panelist is sent equipment (e.g., data collection devices) when the intermediate training session is scheduled. In some examples, the interested participant may be sent (e.g., provided with) the equipment in response to returning the consent form.

The data collection circuitry 108 includes example remote desktop interface circuitry 214 to enable a technician to access a desktop of the electronic device 102 corresponding to the interested panelist. For example, the technician may access the desktop of the electronic device 102 during the intermediate training and/or any other point during the onboarding process or during a study (e.g., for purposes of calibration, troubleshooting, etc.). In some examples, the technician(s) and the interested panelist are in visual and/or audio communication (e.g., via an audio and/or video interface). During the intermediate training session, the technician may re-iterate information from the training instruction(s) 210 and/or the procedure(s) 212, introduce the interested panelist to the equipment, set the interested panelist up for a trial (e.g., training) study session, etc. It is understood that the intermediate training session may be omitted in additional or alternative examples.

In the illustrated example of FIG. 2, the database 204 includes one or more example trial studies 216, which facilitate the training of the interested panelist to perform a study. For example, the trial study 216 may be a study that is designed to introduce the interested panelist to a typical study and to provide the interested panelist with firsthand experience with performing a study session. The trial study 216 may call for the interested panelist to connect and utilize one or more data collection devices, such as for example, the EEG sensor 122, the EKG sensor 126, and/or eye-tracking. The trial study 216 may be configured to teach the interested panelist how to troubleshoot when experiencing an issue with a data collection device. For example, the trial study 216 may interactively guide the interested panelist on how to generate strong connections between the EEG sensor 122 and the electronic device 102 and/or location on their body for data gathering, what type of felts or pins to use with electrodes of the EEG sensor 122 (e.g., based on hair presence and/or type), etc. In some examples, the interested panelist may be able to connect with a trained technician during the trial study 216 (e.g., via the remote desktop interface circuitry 214). In some examples, the interest panelist(s) may need to complete two or more (e.g., four) trial study sessions before being considered onboarded. It is understood that the trail study(ies) 216 may be omitted in other examples.

In some examples, the database 204 includes onboarded participant(s) data 217, which may be a data structure that includes panelists that have complete the onboarding process. In some examples, the onboarded participant data 217 includes indices that map the onboarded participants to corresponding data in the panelist database 110 of FIG. 1. In some examples, the onboarded participant(s) data 217 is cross-citable with the panelist database 110. In some examples, the participant recruiter circuitry 206 may search the onboarded participant(s) data 217 and/or the panelist database 110 to identify potential participants for a study.

The data collection circuitry 108 of FIG. 2 includes example feedback circuitry 218, which is structured to provide feedback to an interested panelist, a participant(s), and/or another panelist (e.g., via the electronic device(s) 102). In some examples, the feedback circuitry 218 is instantiated by processor circuitry executing feedback instructions and/or configured to perform operations such as those represented by the flowchart of FIG. 9. Upon receipt of data corresponding to a trial study session, the feedback circuitry 218 can provide feedback to the interested panelist indicating a quality of the study data and/or whether troubleshooting is needed to generate better data. For example, a human and/or machine may review the trail study data corresponding to the interest panelist during the onboarding process to identify a condition of the data and/or connections of the data collection devices. In response to identifying an issue, the feedback circuitry 218 can transmit information to the interested participant that can help the interested participant address the issue(s). In some examples, the feedback includes whether the panelist can continue based on engagement metrics, data quality metrics, etc. measured from training session(s).

In some examples, the data collection circuitry 108 includes means for providing feedback to a participant. For example, the means for providing feedback may be implemented by feedback circuitry 218. In some examples, the feedback circuitry 218 may be instantiated by programmable circuitry such as the example programmable circuitry 1512 of FIG. 15. For instance, the feedback circuitry 218 may be instantiated by the example microprocessor 1700 of FIG. 17 executing machine executable instructions such as those implemented by at least blocks 910 of FIG. 9. In some examples, the feedback circuitry 218 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the feedback circuitry 218 may be instantiated by any other combination of hardware, software, and/or firmware. For example, the feedback circuitry 218 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection circuitry 108 includes example study generator circuitry 220, which is structured to generate a study (e.g., to develop protocols/study designs). In some examples, the study generator circuitry 220 is instantiated by processor circuitry executing study generator instructions and/or configured to perform operations such as those represented by the flowchart of FIG. 9. In some examples, the study generator circuitry 220 facilitates the development of protocols and/or study designs for a study. In some examples, the data collection circuitry 108 allows a researcher and/or other conductor of a study (e.g., a healthcare provider, etc.) to select a set or subset of neurological and/or physiological data to be collected for a particular study or protocol. In some examples, the example data collection application circuitry 128 used by the participant during the study is structured to be capable of collecting a plurality of modalities for collecting all of these modalities (e.g., EEG, eye tracking, biometrics, facial encoding, galvanic skin response, heart rate, etc.). During generation of the study, the researcher can input one or more modalities of interest for the study based on a target for the study. For example, the researcher may select EEG and eye-tracking, just EEG, just eye-tracking, etc. In some examples, a potential participant may be alerted to the one or more modalities of interest prior to agreeing to participate in the study.

In some examples, the study generator circuitry 220 generates detailed instructions (e.g., step-by-step instructions) that describe how to set up, connect, and calibrate a participant's data connection(s) based on the one or modalities of interest. In some examples, the study generator circuitry 220 provides detailed instructions that include specific calibration guidance for each nervous system measurement to facilitate self-calibration. For example, the detailed instructions can include guidance on how to set up, connect, and calibrate a sensor(s) needed for the nervous system measurements, such as the EEG sensor(s) 122, the galvanic skin response sensor(s) 124, the EKG sensor(s) 126, the camera(s) 118, etc. During the session, the participant need only to calibrate measurement devices from which measurements need to be collected (as opposed to every possible measurement device). In some examples, the study generator circuitry 220 transmits an example data packet(s) (e.g., data packet(s) 308 of FIG. 3) to the electronic device(s) 102 corresponding to the participant(s).

In some examples, the data collection circuitry 108 includes means for generating a study. For example, the means for generating a study may be implemented by study generator circuitry 220. In some examples, the study generator circuitry 220 may be instantiated by programmable circuitry such as the example programmable circuitry 1512 of FIG. 15. For instance, the study generator circuitry 220 may be instantiated by the example microprocessor 1700 of FIG. 17 executing machine executable instructions such as those implemented by at least blocks 902 of FIG. 9. In some examples, the study generator circuitry 220 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the study generator circuitry 220 may be instantiated by any other combination of hardware, software, and/or firmware. For example, the study generator circuitry 220 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

Upon receipt of the participant's data and/or responses, the feedback circuitry 218 provides feedback and/or confirmation of compensation for the participants. In some examples, the feedback circuitry 218 provides feedback when feedback after each study session. In some examples, the feedback circuitry 218 provides feedback when feedback is warranted (e.g., based on data quality check(s), validation results, etc.).

The example data collection circuitry 108 includes example data pre-processor circuitry 222, which is structured to process study data obtained from a participant (e.g., via the electronic device(s) 102) prior to detailed analysis of the data. In some examples, the data pre-processor circuitry 222 is instantiated by processor circuitry executing data pre-processor instructions and/or configured to perform operations such as those represented by the flowchart of FIGS. 9-10. In some examples, the data pre-processor circuitry 222 pre-processes study data at a participant level prior to aggregation of study data across participants. In other words, the data pre-processor circuitry 222 can perform individual session-based analysis of study data to perform data personalization and/or prepare the study data for group analysis, which is performed at the group level.

The data pre-processor circuitry 222 of FIG. 2 can perform one or more pre-processing functions. In some examples, the data pre-processor circuitry 222 filters (e.g., cleanses) the study data (e.g., to remove noise, artifacts, other irrelevant data, etc.). For example, the data pre-processor circuitry 222 can remove certain EEG artifacts from the study data that are specific to a corresponding study and/or participant. In some examples, the data pre-processor circuitry 222 analyzes the study data to determine a level of completeness of the study. In some examples, the data pre-processor circuitry 222 performs quality checks on the data. In some examples, the data pre-processor 222 performs completeness check(s) to determine a level of completeness of the study data. For example, the data pre-processor 222 can determine whether the study data includes response data for an entirety of the session and for corresponding modalities.

In some examples, the data pre-processor circuitry 222 separates the study data into regions of interest based on events of interest (e.g., unique markers, described in further detail below). In some examples, an example study session can last approximately 15-20 minutes, during which the data collection application circuitry 128 may collect first study data that is of greater importance to the market research entity 104 relative to second study data. In some such examples, the data pre-processor circuitry 222 can isolate and validate the first study data. In some examples, the data pre-processor circuitry 222 performs the quality check on the first data to determine whether a quality of the first data is acceptable for an event of interest.

In some examples, the data analyzer circuitry 226 uses techniques and/or mechanisms to personalize each participants' data to generate personalized data. The data pre-processor circuitry 222 of FIG. 2 includes example personalization circuitry 224, which is structured to extract signatures from the study data that correspond to the respective participant from which the study data was collected. For example, personalization circuitry 224 may identify frequency oscillations in the EEG measurements that are specific to the participant. However, it is understood that the personalization circuitry 224 is not limited to identifying frequency oscillations in EEG measurements and may identify additional or alternative signatures that correspond to the participant in other examples.

In some examples, the personalization circuitry 224 saves the personalized data in the database 204 by associating the personalized data with a respective participant. In some examples, the personalized data can be used to determine whether the participant is actually the person the participant alleges. In other words, the personalized data case be used to corroborate the identity of the participant. In some examples data personalization provides operational benefits. For example, the personalized data can be used to avoid repeating certain activities in each session, such as for example, calibration. That is, the personalized data can be used during calibration of data collection devices by the participant to reduce a duration of a session. In some examples, data personalization provides research benefits. For example, by generating personalized data for the participant across multiple study sessions, the market research entity 104 may be able to aggregate the data and apply insights to future research and/or publications.

In some examples, the data collection circuitry 108 includes means for pre-processing data. For example, the means for pre-processing data may be implemented by data pre-processor circuitry 222. In some examples, the data pre-processor circuitry 222 may be instantiated by programmable circuitry such as the example programmable circuitry 1512 of FIG. 15. For instance, the data pre-processor circuitry 222 may be instantiated by the example microprocessor 1700 of FIG. 17 executing machine executable instructions such as those implemented by at least blocks 1004 of FIG. 10. In some examples, the data pre-processor circuitry 222 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the data pre-processor circuitry 222 may be instantiated by any other combination of hardware, software, and/or firmware. For example, the data pre-processor circuitry 222 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection circuitry 108 includes example data analyzer circuitry 226, which is structured to analyze data collected for one or more studies. In some examples, the data analyzer circuitry 226 is instantiated by processor circuitry executing data analyzer instructions and/or configured to perform operations such as those represented by the flowchart of FIGS. 9-10. In some examples, the data analyzer circuitry 226 performs group analysis in response to detecting a sample of pre-processed study data that includes plurality of participant study data with desired demographics. As disclosed herein, a sample refers to a group of people who collected and transmitted study data to the market research entity 104 and who, when combined, align with a target demographic(s). In some examples, the sample includes a target amount of people that participated in the session. In some examples, the sample includes sub-sampling criteria for the study, such as (but not limited to) a target amount of men and women.

The data analyzer circuitry 226 of FIG. 2 can aggregate the study data (e.g. the neurophysiological and behavior responses) across a plurality of sessions corresponding to a plurality of participants. In some examples, the data analyzer circuitry 226 performs cross-modality analysis to unify (e.g., merge, combine, fuse, validate, etc.) the aggregated data to provide a robust measure of engagement and predict actionable behavior. Unifying as disclosed herein refers to techniques for combining different modalities to generate a cohesive message or diagnostic of what a marketing material solicits from the participants along a direction of the sessions (e.g., second to second). In some examples, the data analyzer circuitry 226 aligns or otherwise unifies the study data across modalities based on reaction times. In some examples, the cross-modality analysis enables more robust learning from aligned combinations of modalities.

Each modality provides an indication of a specific reaction(s). For example, analyzing EEG data can enable a determination that a video was particularly engaging at a specific time. Further, eye-tracking data can enable a determination of a region of the video that participant was viewing at the specific time. By unifying the data, the data analyzer circuitry 226 can enable a determination of which region of the video viewed by the participate at the specific time caused the increased engagement. As another example, analysis of facial encoding data by the data analyzer circuitry 226 can enable a determination not only that a specific portion of a video at a specific time is emotionally motivating, but also whether the emotion motivation is positive, negative, surprising, etc. Also, in some examples, data from individual participant sessions from a plurality of individuals can be combined to derive a group behavior that can be used to determine an effectiveness of a marketing material.

In some examples, the data analyzer circuitry 226 performs a cross modality analysis to generate outcome measures (e.g., attention, emotion, memory activation, subconscious associations to message/brands, etc.). In some examples, the data analyzer circuitry 226 provides a composite output characterizing the effectiveness of the marketing material from the study based on the cross-modality analysis. In some examples, the data analyzer circuitry 226 analyzes each modality separately. For example, the data analyzer circuitry 226 may analyze the eye-tracking data separate from the EEG data. However, unifying the data across the modalities enables more cohesive and/or robust insights because each type of measurement is a component of the aggregated or full participant response.

In some examples, the data collection circuitry 108 includes means for analyzing data. For example, the means for analyzing may be implemented by data analyzer circuitry 226. In some examples, the data analyzer circuitry 226 may be instantiated by programmable circuitry such as the example programmable circuitry 1512 of FIG. 15. For instance, the data analyzer circuitry 226 may be instantiated by the example microprocessor 1700 of FIG. 17 executing machine executable instructions such as those implemented by at least blocks 914, 1002-1022 of FIGS. 9-10. In some examples, the data analyzer circuitry 226 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the data analyzer circuitry 226 may be instantiated by any other combination of hardware, software, and/or firmware. For example, the data analyzer circuitry 226 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection circuitry 108 includes example report generator circuitry 228, which is structured to generate a report based on the analyzed data. In some examples, the report generator circuitry 228 is instantiated by processor circuitry executing report generator instructions and/or configured to perform operations such as those represented by the flowchart of FIG. 9. In some examples, a composite output with an effectiveness of various stimuli from the data analyzer circuitry 226 is directed to the report generator circuitry 228.

The report generator circuitry 228 of FIG. 2 includes example custom report circuitry 230, which allows the market research entity 104 and/or a client(s) (e.g., market participants) to self-serve custom insights from the composite modal outputs characterizing the effectiveness of the stimulus material. In some examples, the custom report circuitry 230 implements a client specific dashboard and/or database. In some examples, the custom report circuitry 230 may be a reporting platform that allows clients to dissect, scrutinize, and acutely analyze specific data, which also facilitates diagnostic assessment of the marketing materials and/or other stimulus. In some examples, the custom report circuitry 230 enables clients to generate custom insights across different modalities (e.g., EEG, eye-tracking, facial expression extraction, biometrics, post-survey questionnaire). For example, custom report circuitry 230 enables the client to retrieve data based on a certain specific time modality and/or specific signatures the client identifies. For example, an EEG sensor can measure approximately 256 times per second. The custom report circuitry 230 can enable the client to perform self-diagnostics on a second-by-second level. In some examples, the insights can help the client benchmark to types of advertisements or other marketing materials the client may prefer to benchmark to itself. In some examples, the custom report circuitry 230 implements means for customizing a data report.

In some examples, the data collection circuitry 108 includes means for generating a report. For example, the means for generating a report may be implemented by report generator circuitry 228. In some examples, the report generator circuitry 228 may be instantiated by programmable circuitry such as the example programmable circuitry 1512 of FIG. 15. For instance, the report generator circuitry 228 may be instantiated by the example microprocessor 1700 of FIG. 17 executing machine executable instructions such as those implemented by at least blocks 916 of FIG. 9. In some examples, the report generator circuitry 228 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the report generator circuitry 228 may be instantiated by any other combination of hardware, software, and/or firmware. For example, the report generator circuitry 228 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

While an example manner of implementing the data collection circuitry 108 of FIG. 1 is illustrated in FIG. 2, one or more of the elements, processes, and/or devices illustrated in FIG. 2 may be combined, divided, re-arranged, omitted, eliminated, and/or implemented in any other way. Further, the example interface circuitry 202, example participant recruiter circuitry 206, example feedback circuitry 218, example remote desktop interface circuitry 214, example data pre-processor circuitry 222, example study generator circuitry 220, example personalization circuitry 224, example data analyzer circuitry 226, example report generator circuitry 228, example custom report generator circuitry 230, and/or, more generally, the example data collection circuitry 108 of FIG. 2, may be implemented by hardware alone or by hardware in combination with software and/or firmware. Thus, for example, any of the example interface circuitry 202, example participant recruiter circuitry 206, example feedback circuitry 218, example remote desktop interface circuitry 214, example data pre-processor circuitry 222, example personalization circuitry 224, example study generator circuitry 220, example data analyzer circuitry 226, example report generator circuitry 228, example custom report generator circuitry 230, and/or, more generally, the example data collection circuitry 108, could be implemented by programmable circuitry in combination with machine readable instructions (e.g., firmware or software), processor circuitry, analog circuit(s), digital circuit(s), logic circuit(s), programmable processor(s), programmable microcontroller(s), graphics processing unit(s) (GPU(s)), digital signal processor(s) (DSP(s)), ASIC(s), programmable logic device(s) (PLD(s)), and/or FPLD(s) such as FPGAs. Further still, the example data collection circuitry 108 of FIG. 2 may include one or more elements, processes, and/or devices in addition to, or instead of, those illustrated in FIG. 2, and/or may include more than one of any or all of the illustrated elements, processes and devices.

FIG. 3 is a block diagram of an example implementation of the data collection application circuitry 128 of FIG. 1 for monitoring a participant during a session to obtain neurological, physiological, and/or behavioral data. The data collection application circuitry 128 of FIG. 3 may be instantiated (e.g., creating an instance of, bring into being for any length of time, materialize, implement, etc.) by programmable circuitry such as a CPU executing first instructions. Additionally or alternatively, the data collection application circuitry 128 of FIG. 3 may be instantiated (e.g., creating an instance of, bring into being for any length of time, materialize, implement, etc.) by (i) an ASIC and/or (ii) a FPGA structured and/or configured in response to execution of second instructions to perform operations corresponding to the first instructions. It should be understood that some or all of the circuitry of FIG. 3 may, thus, be instantiated at the same or different times. Some or all of the circuitry of FIG. 3 may be instantiated, for example, in one or more threads executing concurrently on hardware and/or in series on hardware. Moreover, in some examples, some or all of the circuitry of FIG. 3 may be implemented by microprocessor circuitry executing instructions and/or FPGA circuitry performing operations to implement one or more virtual machines and/or containers.

The data collection application circuitry 128 includes example interface circuitry 302 to facilitate communication between the data collection application circuitry 128 and the data collection circuitry 108 (e.g., the components thereof). In some examples, the interface circuitry 302 receives a survey from the data collection circuitry 108 that includes one or more questions to determine the participant's qualification to participate in the study. In some examples, data collection application circuitry 128 is structured to receive a study from the data collection circuitry 108. In some examples, the participant(s) may receive a direct notification (e.g., an email, an application alert, a text message, etc.) via the electronic device 102 and/or another electronic device. In some examples, the participant(s) may be asked to confirm their acceptance of and/or availability for the study via the survey and/or the study. In some examples, the participant can independently participate in the data collection session(s) and/or the survey at their own convenience.

The data collection application circuitry 128 includes example authenticator circuitry 304, which provides an interface through which the participant can securely log in to the data collection application circuitry 128. The participant may log in to the data collection application circuitry 128 to access the survey(s) and/or the study(s) to initiate a session. In some examples, the authenticator circuitry 304 utilizes biometrics to enable the participant to log in. For example, the authenticator circuitry 304 may utilize image data from the camera(s) 118 and perform facial recognition. In some examples, other biometrics may be utilized, such as fingerprint analysis. In some examples, voice recognition and/or another form of personalized recognition may be utilized. In some examples, the participant may provide a username/password. However, it is understood that any suitable authentication may be used in additional or alternative examples.

In some examples, the data collection application circuitry 128 includes means for authentication. For example, the means for authentication may be implemented by authenticator circuitry 304. In some examples, the authenticator circuitry 304 may be instantiated by programmable circuitry such as the example programmable circuitry 1612 of FIG. 16. For instance, the authenticator circuitry 304 may be instantiated by the example microprocessor 1700 of FIG. 17 executing machine executable instructions such as those implemented by at least blocks 1104 of FIG. 11. In some examples, the authenticator circuitry 304 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the authenticator circuitry 304 may be instantiated by any other combination of hardware, software, and/or firmware. For example, the authenticator circuitry 304 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection application circuitry 128 includes example storage circuitry 306, which is structured to store data. In some examples, the storage circuitry 306 is instantiated by processor circuitry executing storage instructions and/or configured to perform operations such as those represented by the flowcharts of FIGS. 11-14. In some examples, an example data packet(s) 308 that is received via the interface circuitry 302 is stored in the storage circuitry 306. The data packet(s) 308 can include, but is not limited to, training materials, a study, and/or a survey to determine eligibility to participate in the study. For example, the data packet(s) 308 can include stimulus materials and a corresponding study. In some examples, the data packet(s) 308 includes training materials (e.g., training instruction(s) 210, procedures 212, trial study(ies) 216, etc.), which may include detailed instructions to setup, connect, and calibrate a participant data connection. In some examples, the instructions allow calibration, baselining, and/or personalization of each participants' session (e.g., via results of the personalization circuitry 224 of FIG. 2). In some examples, the data packet(s) 308 includes an option to provide behavioral feedback and/or an answer(s) to one or more stimulus-related questions. In some examples, the storage circuitry 306 implements a secure local folder or other database into which example stimulus materials for the study are securely downloaded. In some examples, the storage circuitry 306 automatically downloads the session data needed to view the stimulus materials.

In some examples, the data collection application circuitry 128 includes means for storing data. For example, the means for authentication may be implemented by storage circuitry 306. In some examples, the storage circuitry 306 may be instantiated by programmable circuitry such as the example programmable circuitry 1612 of FIG. 16. For instance, the storage circuitry 306 may be instantiated by the example microprocessor 1700 of FIG. 17 executing machine executable instructions such as those implemented by at least blocks 1114 of FIG. 11. In some examples, the storage circuitry 306 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the storage circuitry 306 may be instantiated by any other combination of hardware, software, and/or firmware. For example, the storage circuitry 306 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection application circuitry 128 includes example participant trainer circuitry 310 to facilitate training of a participant prior to execution of a study. In some examples, the participant trainer circuitry 310 is instantiated by processor circuitry executing participant trainer instructions and/or configured to perform operations such as those represented by the flowcharts of FIGS. 11-14. As noted above, the participant may need and/or desire to go through an onboarding process before participating in a study. The participant recruiter circuitry 206 of FIG. 2 can transmit a data packet(s) to the electronic device 102 that enables the participant to engage in an initial training session, which may be a first step in the onboarding process. The onboarding process may additionally or alternatively include the intermediate training session during which a technician may re-iterate information from the initial training session, introduce the interested panelist to the data collection device, and/or set the participant up for a trial (e.g., training) study session, etc. The participant trainer circuitry 310 of FIG. 3 guides the participant through the initial training session, the intermediate training session and/or the one or more trial study sessions.

In some examples, the participant trainer circuitry 310 performs noise interference training. During the training process, the participant trainer circuitry 310 attempts to identify sources of the data interference (e.g., electronic interference, etc.) that could affect the study data. For EEG data, for example, the data interference may be a lighting source or another device propagating noise. In some examples, an artifact may affect the EEG frequencies or another frequency collected by the data collection application circuitry 128. In some examples, the participant trainer circuitry 310 and/or a human (e.g., via the participant trainer circuitry 310) may provide feedback to the participant to take an action to prevent such noise interference. In some examples, noise interference training is an iterative process that can cross trial study sessions and/or other study sessions and/or may occur one or more times during a single study session.

In some examples, the data collection application circuitry 128 includes means for training. For example, the means for training may be implemented by participant trainer circuitry 310. In some examples, the participant trainer circuitry 310 may be instantiated by programmable circuitry such as the example programmable circuitry 1612 of FIG. 16. For instance, the participant trainer circuitry 310 may be instantiated by the example microprocessor 1700 of FIG. 17 executing machine executable instructions such as those implemented by at least blocks 1106, 1202-1224, 1302-1320, 1402-1422 of FIGS. 11-14. In some examples, the participant trainer circuitry 310 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the participant trainer circuitry 310 may be instantiated by any other combination of hardware, software, and/or firmware. For example, the participant trainer circuitry 310 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection application circuitry 128 includes example remote support circuitry 312 to provide a connection to a trained support technician(s). In some examples, the remote support circuitry 312 is instantiated by processor circuitry executing remote support instructions and/or configured to perform operations. The remote support circuitry 312 allows the participant(s) to contact remote support technicians for support. In some examples, the remote support circuitry 312 is implemented by enabling instant messaging between the participant(s) (e.g., via the data collection application circuitry 128) and the support technician. In some examples, the remote support circuitry 312 is implemented by connecting the electronic device 102 with a support technician via a telephone call or other voice call.

In some examples, the remote support circuitry 312 enables remote access by the support technician(s) to the data collection application circuitry 128 executing on the electronic device 102 (e.g., via a remote desktop connection). For example, a trained technician may remotely view and/or interact with the data collection application circuitry 128 corresponding to the participant to identify an issue and/or communicate with the participant. In some examples, the remote support circuitry 312 enables additional or alternative connection techniques between the electronic device 102 and the support technician(s).

The data collection application circuitry 128 includes example facial emotion encoder circuitry 314 to encode facial expressions. In some examples, the facial emotion encoder circuitry 314 is instantiated by processor circuitry executing facial emotion encoder instructions and/or configured to perform operations such as those represented by the flowchart of FIG. 11. In some examples, the facial emotion encoder circuitry 314 utilizes image data from the example camera(s) 118 to infer the participant's emotion at a given moment and/or over time. For example, the facial emotion encoder circuitry 314 can detect a smile on a face of a participant and infer a joyful emotion.

The data collection application circuitry 128 includes example eye-tracking circuitry 316 to perform eye-tracking. In some examples, the eye-tracking circuitry 316 is instantiated by processor circuitry executing eye-tracking instructions and/or configured to perform operations such as those represented by the flowchart of FIG. 11. In some examples, the eye-tracking circuitry 316 utilizes image data from the example camera(s) 118 to determine where the participant(s) is looking at a given moment and/or over time. In some examples, the eye-tracking circuitry 316 identifies a size of a user's pupils.

The data collection application circuitry 128 includes example session manager circuitry 318 to manage a study. In some examples, the session manager circuitry 318 is instantiated by processor circuitry executing session manager instructions and/or configured to perform operations such as those represented by the flowchart of FIGS. 11-14. In some examples, the session manager circuitry 318 determines whether the participant(s) is securely logged into the data collection application circuitry 128. For example, the session manager circuitry 318 can determine whether the participant logged into the data collection application circuitry 128 via the authenticator circuitry 304 (e.g., via facial recognition, fingerprint recognition, username/password, etc.) and/or whether the secure connection remains established. If the secure connection is not established, session manager circuitry 318 may provide an alert to the participant to authenticate.

When the participant establishes a secure connection with the data collection application circuitry 128, the session manager circuitry 318 can detect a data packet(s) 308 containing a study. In other words, prior to analyzing the data packet(s) 308 containing the study, determining device calibration, and/or initiating the study, the session manager circuitry 318 can identify the secure connection. In some examples, upon detection of the data packet(s) 308, the session manager circuitry 318 analyzes contents of the data packet 308 to identify which data collection device(s) is to be utilized. The session manager circuitry 318 of FIG. 3 provides an indication of the one or more data collections devices to example calibration manager circuitry 320 to facilitate calibration. In additional or alternative examples, the session manager circuitry 318 determines whether the one or more data collection devices are calibrated. When the session manager circuitry 318 identifies one or more un-calibrated data collection devices, the session manager circuitry 318 provides an indication to example calibration manager circuitry 320 to calibrate the ones or more un-calibrated data collection devices.

In some examples, the session manager circuitry 318 identifies a first measurement device to be calibrated, and provides an indication to the calibration manger circuitry 320 to instruct a participant to calibrate the first measurement device. As discussed in further detail below, when the first measurement device is calibrated, the session manager circuitry 318 can render a study to the participant, which includes a material of interest. During the study, the session manager circuitry 318 records measurements of biological responses of the study participant using the calibrated first measurement device. In some examples, the session manager circuitry 318 uses the timer 120 to associate timestamps with one or more recorded measurements.

The data collection application circuitry 128 includes the example calibration manager circuitry 320 to manage calibration(s) of one or more data collection devices to be used for the study. In some examples, the calibration manager circuitry 320 is instantiated by processor circuitry executing calibration manager instructions and/or configured to perform operations such as those represented by the flowchart of FIGS. 11-14. The calibration manager circuitry 320 of FIG. 3 performs checks on the data collection device(s) to determine whether the data collection device(s) is connected and/or functioning properly.

In some examples, the calibration manager circuitry 320 facilitates self-calibration of the data collection device(s) and/or a nervous system measurement(s). The calibration manager circuitry 320 can provide guidance (e.g., instructions) to the participant(s) on how to set-up and/or calibrate sensors to generate an effective signal quality between the sensor(s) and the data collection application circuitry 128. For example, the calibration manager circuitry 320 can systematically guide the participant into connecting the hardware, the calibration process (e.g., step-by-step guide(s) to generate high quality data for a session), etc. The calibration manager circuitry 320 enables the participant(s) to set-up, initiate, and begin the study session(s) without supervision of a trained technician and/or at a time convenient to the participant(s). The calibration manager circuitry 320 of FIG. 3 enables the market research entity 104 to obtain study data from many more participants and across a larger number of demographics, which have been left out of studies performed by traditional data collection systems that relied on trained technicians. In some examples, the calibration manager circuitry 320 can apply personalized data from a previous session during the calibration process that reduces an amount of calibrating needed before beginning a study, reducing an amount of computing resources need to perform calibration.

In some examples, the calibration manager circuitry 320 facilitates speed calibration after head and/or face position calibration. In some examples, the calibration manager circuitry 320 facilitate speed calibration by directing the participant to look at a dot or other insignia on the calibration screen, which may disappear upon detection of the participant's gaze at the dot. The participant may be directed to identify different dots at different times (e.g., five per round). In some examples, the calibration manager circuitry 320 provides multiple arounds of speed calibration. In some examples, the calibration manager circuitry 320 may generate and/or display a speed calibration score that identifies how successful the calibration was (e.g., 5/4, 4/5, etc.). If the participant receives a score of less than 100%, the calibration manager circuitry 320 may allow the participant to complete one or more additional attempts at speed calibration.

In some examples, the participant is allowed a certain (e.g., threshold) amount of attempts at speed calibration. In some examples, when the participant is unable to successfully complete speed calibration, the participant may be able to participate in the study without eye-tracking. For example, the study may include an indication of whether the eye-tracking capability is mandatory to complete the study. When the eye-tracking is not mandatory, the calibration manager circuitry 320 may pass the participant to another screen, such as a subsequent calibration, to the study, to a feedback screen, etc.

In some examples, the calibration manager circuitry 320 includes facial expression calibration. During facial expression calibration, the calibration manager circuitry 320 can detect or otherwise measure conditions surrounding the electronic device 102. For example, the conditions can include (but are not limited to) a brightness level, contrast, etc. The calibration manager circuitry 320 can utilize the conditions surrounding the electronic device 102 to calibrate the facial emotion encoder circuitry 314. In some examples, the calibration manager circuitry 320 provides feedback to the participant regarding the conditions, such as to reduce and/or increase an amount of ambient light surrounding the electronic device 102. In some examples, the calibration manager circuitry 320 provides feedback to the participant regarding movements of the head and/or face to assist in creating a baseline for the facial expression calibration.

In some examples, the data collection application circuitry 128 includes means for facilitating calibration. For example, the means for facilitating calibration may be implemented by calibration manager circuitry 320. In some examples, the calibration manager circuitry 320 may be instantiated by programmable circuitry such as the example programmable circuitry 1612 of FIG. 16. For instance, the calibration manager circuitry 320 may be instantiated by the example microprocessor 1700 of FIG. 17 executing machine executable instructions such as those implemented by at least blocks 1106, 1202-1224, 1302-1320, 1402-1422 of FIGS. 11-14. In some examples, the calibration manager circuitry 320 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the calibration manager circuitry 320 may be instantiated by any other combination of hardware, software, and/or firmware. For example, the calibration manager circuitry 320 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

In some examples, the session manager circuitry 318 tests connections and/or calibrations of nervous system measurements and/or devices to record the nervous system measurements. In some examples, the session manager circuitry 318 determines readiness for the session based on connectivity and calibration results. For example, the session manager circuitry 318 may not allow the participant(s) to begin the study until the nervous system measurement are connected and calibrated. In some examples, when the session manager circuitry 318 determines the nervous system measurements and/or devices to record the nervous system measurements are connected and calibrated, the session manager circuitry 318 allows the participant(s) to initiate the session. When participant(s) is ready, the participant(s) can proceed to the start of the session.

An example session includes (but is not limited to) one or more of a series of stimuli (video or image), tasks that produce or induce an active response, image or word probes, instructions, etc. In some examples, upon an initiation of the study by the participant, the session manager circuitry 318 plays the study script. During the session, the session manager circuitry 318 records one or more nervous system measurements to generate example neurological data 324 and stores the example neurological data 324 in the storage circuitry 306.

In some examples, the session manager circuitry 318 synchronizes time events across multiple nervous system measurements and/or different modal systems across. In some examples, a modal system refers to one or more measurements from one or more components that can be combined to generate an insight. For example, the participant's emotion at a given moment (e.g., determined by the facial emotion encoder circuitry 314) can be combined with a determination of where the participant is looking at the give moment to determine what emotion a portion of a marketing material solicited from the participant.

The data collection application circuitry 128 of FIG. 3 includes example focus tracker circuitry 326 to monitor a focus level of the participant. In some examples, focus tracker circuitry 326 is instantiated by processor circuitry executing focus tracker instructions and/or configured to perform operations such as those represented by the flowcharts of FIG. 11-14. The focus tracker circuitry 326 can implement an algorithm that measures participant focus and/or engagement with the marketing material during the session. For example, the focus tracker circuitry 326 may utilize one or more modalities, such as EEG, eye-tracking, and/or behavioral measurements during the session (e.g., viewing stimulus materials) to determine whether the participant is engaging with the marketing material. For example, the focus tracker circuitry 326 can determine whether the study participant looks away from the display 114 a threshold amount of times within a specific duration, through the study, etc. The focus tracker circuitry 326 may monitor (e.g., periodically, aperiodically, continuously, etc.) for data quality base, signal quality, EEG quality base, subject focus (e.g., eyes on screen, head position within certain boundaries etc.). In some examples, the focus tracker circuitry 326 intervenes during a session to enable the market research entity 104 pre-emptively respond to salvage the study data. For example, the focus tracker circuitry 326 may provide feedback to the participate (e.g., in real time) for corrective action(s).

At the end of the session, the session manager circuitry 318 enables the participants to provide behavioral feedback. In some examples, the session manager circuitry 318 provides the participant(s) with stimulus-related questions and allows the participant(s) to respond to the questions. For example, the questions can include emotions elicited in the participant by the material during the session, etc. In some examples, the session manager circuitry 318 generates or stores a data file corresponding to the study that includes the recorded measurements and/or behavioral feedback.

In some examples, the data collection application circuitry 128 includes means for managing a study session. For example, the means for managing may be implemented by session manager circuitry 318. In some examples, the session manager circuitry 318 may be instantiated by programmable circuitry such as the example programmable circuitry 1612 of FIG. 16. For instance, the session manager circuitry 318 may be instantiated by the example microprocessor 1700 of FIG. 17 executing machine executable instructions such as those implemented by at least blocks 1100 of FIG. 11. In some examples, the session manager circuitry 318 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the session manager circuitry 318 may be instantiated by any other combination of hardware, software, and/or firmware. For example, the session manager circuitry 318 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

The data collection application circuitry 128 includes example validation circuitry 328, which is structured to validate data recorded during a study and to upload the data to a server (e.g., the data collection circuitry 108). In some examples, the validation circuitry 328 is instantiated by processor circuitry executing validation instructions and/or configured to perform operations such as those represented by the flowchart of FIG. 11. The validation circuitry 328 of FIG. 3 can perform one or more session quality checks to ensure task compliance, data integrity, hardware status, etc. In some examples, the validation includes two parts (e.g., portions, segments, etc.). In some examples, a first part of the validation is to determine whether the session is complete (e.g., meets any requirements, such as input requirements, session duration, inputs that need to happen a certain amount of times, events that need to last for a certain amount of time, etc.). In some examples, a second part of the validation includes identifying a signal quality of the session. However, it is understood that the validation may include additional or alternative parts and/or different parts can be combined.

In some examples, the completeness may be based on a duration of the session. For example, if the study includes a plurality of videos that are collectively 20 minutes in length and the study is estimated to take 30 minutes to complete, the validation circuitry 328 may identify an amount of time in which the participant completed the study and compare that amount of time to the estimate completion time. If the participant completed the study in 15 minutes, the validation circuitry 328 may identify the study as incomplete.

In some examples, the completeness may be based on identification of one or more unique markers (e.g., events, etc.) associated with the marketing material. The unique marker(s) may be different for each study. In some examples, the unique marker(s) may be built into the study. The unique markers indicate specific events of interest for which the market research entity 104 desires measurements.

The unique marker(s) may be, for example, an image, a video, a part of a video, a sequence of logos, an experience, etc. The unique markers indicate an expectation of certain events during the session. For example, the unique marker may be a 30 second video. The validation circuitry 328 may analyze the study data to determine whether all 30 seconds were viewed or whether less than the 30 second were viewed.

In some examples, a failure to identify one or more unique markers may result in reduced compensation for the participant. In some examples, identification or lack thereof of the unique marker(s) may be determinative of whether the session is a qualified that can be used in analysis. In some examples, failure to identify one or more unique markers may necessitate a re-sampling with another participant.

In some examples, the validation circuitry 328 determines a signal quality corresponding to the study session for the second part of the validation. That is, the validation circuitry 328 performs a data quality check(s). For example, the validation circuitry 328 may apply an algorithm to the study data that calculates the EEG and/or eye-tracking signal quality of the overall session. The validation circuitry 328 may identify whether a good signal quality is maintained through the session, whether the data is of a certain quality, etc. The validation circuitry 328 may associate identifications with the study data as preliminary indicators. In some examples, the preliminary indicators may be metadata attached to a data packet corresponding to the study data.

The validation circuitry 328 of FIG. 3 uploads the study data (e.g., the data file) after the validation process. In some examples, the validation circuitry 328 encodes the study data prior to transmission. In some examples, the validation circuitry 328 securely uploads the study data to cloud servers. For example, the validation circuitry 328 initiates upload of the neurophysiological, behavioral and session metadata back to the cloud servers at the conclusion of the session. The upload may include validation data generated during the validation process, which may affect compensation for the participant. For example, if the validation circuitry 328 determines that the study was not fully complete, the validation circuitry 328 may include an indication of the partial completion. In some examples, the partial completion indication may result in the participant receiving partial or no compensation for the study. In some examples, the validation circuitry 328 may provide an alert and/or another indication that over-sampling may be needed (e.g., if one or more criterion are not met by the study study). In some examples, the validation results are shown to the participant. In other examples, the validation results are uploaded to the server without being shown to the participant.

In some examples, the data collection application circuitry 128 includes means for validating a study. For example, the means for validating may be implemented by validation circuitry 328. In some examples, the validation circuitry 328 may be instantiated by programmable circuitry such as the example programmable circuitry 1612 of FIG. 16. For instance, the validation circuitry 328 may be instantiated by the example microprocessor 1700 of FIG. 17 executing machine executable instructions such as those implemented by at least blocks 1118 of FIG. 11. In some examples, the validation circuitry 328 may be instantiated by hardware logic circuitry, which may be implemented by an ASIC, XPU, or the FPGA circuitry 1800 of FIG. 18 configured and/or structured to perform operations corresponding to the machine readable instructions. Additionally or alternatively, the validation circuitry 328 may be instantiated by any other combination of hardware, software, and/or firmware. For example, the validation circuitry 328 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) configured and/or structured to execute some or all of the machine readable instructions and/or to perform some or all of the operations corresponding to the machine readable instructions without executing software or firmware, but other structures are likewise appropriate.

Figure 4:
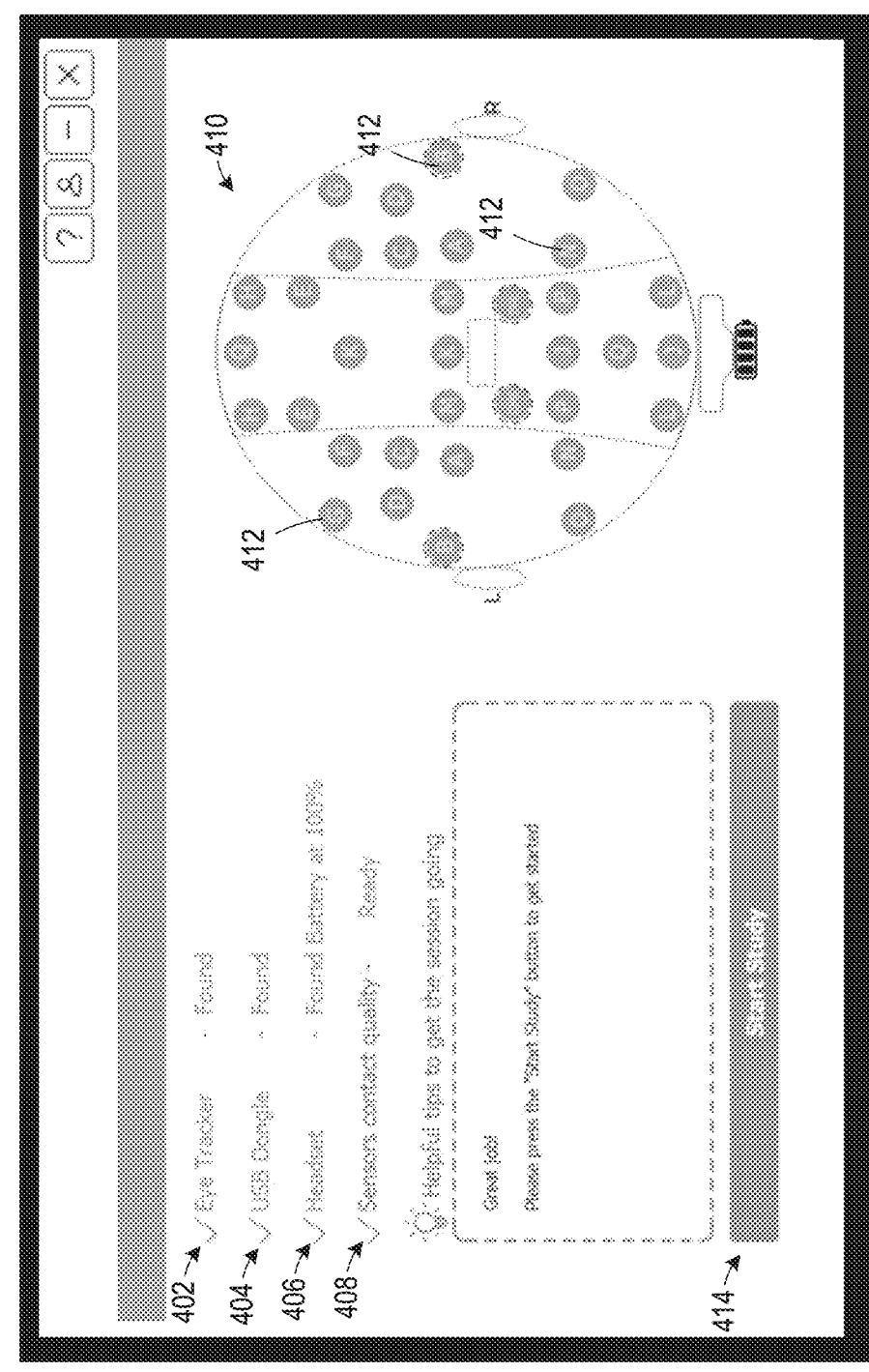
FIG. 4 illustrates a first example calibration user interface.

FIG. 4 illustrates an example calibration user interface or screen 400 in accordance with teachings of this disclosure for calibrating one or more data collection devices. The calibration screen 400 may be rendered by the calibration manager circuitry 320. As illustrated in FIG. 4, the calibration manager circuitry 320 provides an indicator for a plurality of data collection devices. The calibration screen 400 of FIG. 4 includes an example first indicator 402 for eye-tracking connectivity, an example second indicator 404 for USB dongle connectivity (e.g., for connection of a measurement device), an example third indicator 406 for headset connectivity and battery level, and an example fourth indicator 408 for EEG electrode connectivity. The calibration screen(s) 400 may include additional or alternative indicators in other examples, such as (but not limited to) network connection indicators, study download progress and/or success indicators, etc.

The calibration screen 400 of FIG. 4 also illustrates an example interactive EEG calibration visual 410 that may be implemented by the calibration manager circuitry 320. The interactive EEG calibration visual 410 includes a plurality of nodes 412 representing electrodes of an EEG sensor 122. One or nodes 412 may render as a first color (or other indication) when a connection of the node 412 satisfies a threshold, and a second color (or other indication) when a connection of the node 412 fails to satisfy a threshold. In some examples, the EEG calibration is successful when a threshold amount of nodes 412 receives has the first color indication. As illustrated in FIG. 4, the calibration screen 400 can include a link to helpful tips to begin the session. For example, the helpful tips can include tips on setting up the EEG system.

As illustrated in FIG. 4, the calibration screen 400 includes a "start study" icon 414 that becomes available upon calibration of the devices needed for the study session. For example, the participant may be unable to continue to the study until calibration is completed. For example, the "start study" icon may be unavailable until the devices are calibrated.

Figure 5:
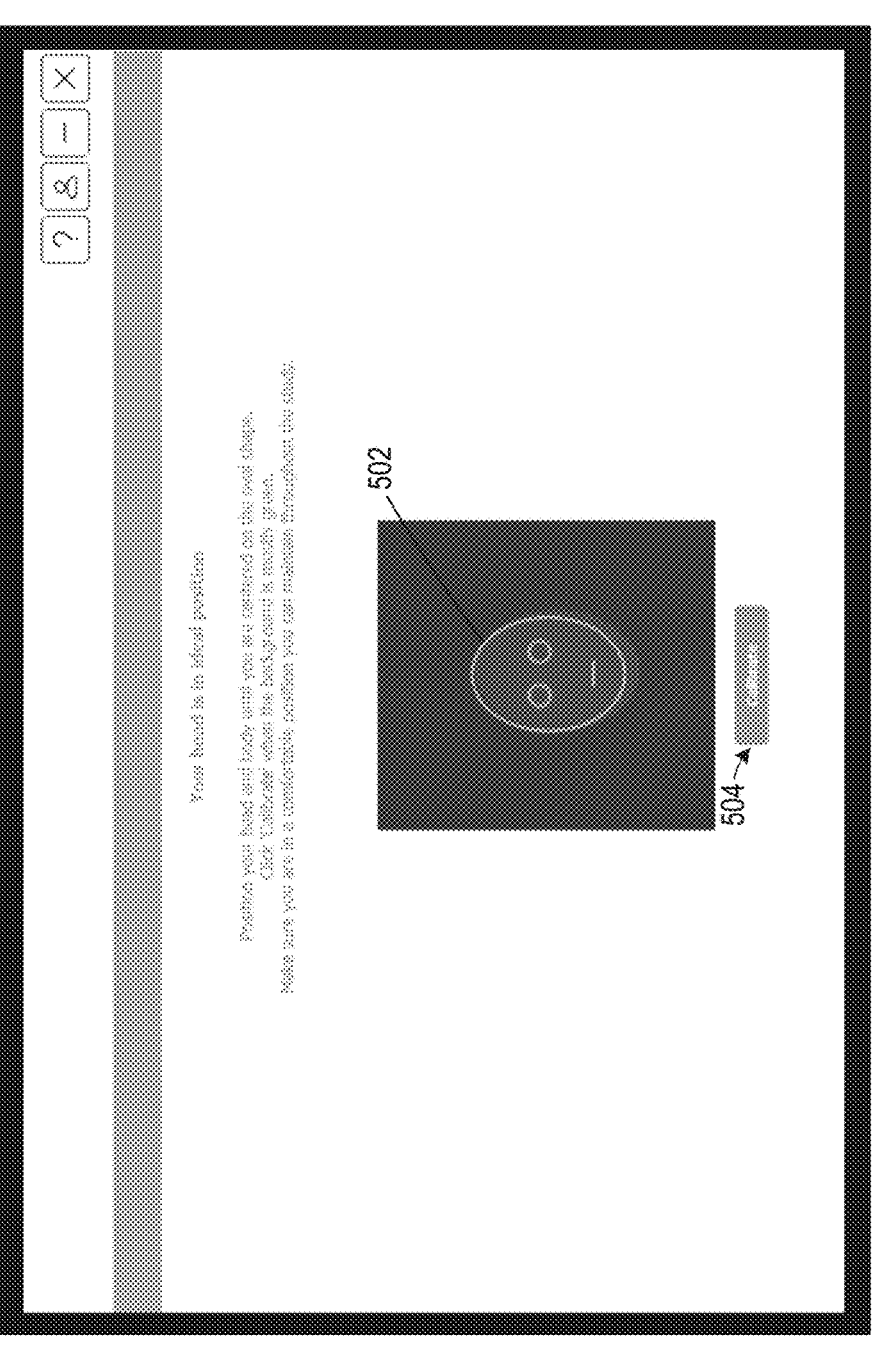
FIG. 5 illustrates a second example calibration user interface.

FIG. 5 illustrates another example calibration user interface or screen 500 in accordance with teachings of this disclosure for calibrating one or more data collection devices. The calibration screen 500 can be rendered by the calibration manager circuitry 320. The calibration manager circuitry 320 provides visual feedback for eye-tracking calibration. As illustrated in FIG. 5, calibration screen 500 includes a designated area 502 (e.g., an oval or other shape). A head and body of the participant is into be positioned until centered in the area 502. In this example, the participant is to click a "calibrate" icon 504 upon a background 506 in which the designated area 502 is disposed includes a specific indication (e.g., a color, etc.). In some examples, the alignment helps to ensure that the participant is at a distance centered position relative to the laptop that enable the eye-tracking circuitry 316 to perform eye-tracking.

While an example manner of implementing the data collection application circuitry 128 of FIG. 1 is illustrated in FIGS. 1 and 3, one or more of the elements, processes, and/or devices illustrated in FIGS. 1 and 3 may be combined, divided, re-arranged, omitted, eliminated, and/or implemented in any other way. Further, the example interface circuitry 302, example authenticator circuitry 304, example storage circuitry 306, example participant trainer circuitry 310, example remote support circuitry 312, example facial emotion encoder circuitry 314, example eye-tracking circuitry 316, example session manager circuitry 318, example focus tracker circuitry 326, example calibration manager circuitry 320, example validation circuitry 328, and/or, more generally, the example data collection application circuitry 128 of FIGS. 1 and 3, may be implemented by hardware alone or by hardware in combination with software and/or firmware. Thus, for example, any of the example interface circuitry 302, example authenticator circuitry 304, example storage circuitry 306, example participant trainer circuitry 310, example remote support circuitry 312, example facial emotion encoder circuitry 314, example eye-tracking circuitry 316, example session manager circuitry 318, example focus tracker circuitry 326, example calibration manager circuitry 320, example validation circuitry 328, and/or, more generally, the example data collection application circuitry 128, could be implemented by programmable circuitry in combination with machine readable instructions (e.g., firmware or software), processor circuitry, analog circuit(s), digital circuit(s), logic circuit(s), programmable processor(s), programmable microcontroller(s), GPU(s), DSP(s), ASIC(s), programmable logic device(s) (PLD(s)), and/or field programmable logic device(s) (FPLD(s)) such as FPGAs. Further still, the example data collection application circuitry 128 of FIGS. 1 and 3 may include one or more elements, processes, and/or devices in addition to, or instead of, those illustrated in FIGS. 1 and 3, and/or may include more than one of any or all of the illustrated elements, processes and devices.

FIG. 6 is a block diagram of an example implementation 600 of the data collection system 100 of FIGS. 1-3 in accordance with teachings of this disclosure. The implementation 600 begins when the example study generator circuitry 220 generates an example study. The study generator circuitry 220 and/or the participant recruiter circuitry 206 select participants 602 (e.g., from the example panelist database 110 of FIG. 1 and/or the onboarded participant data 217 of FIG. 2) to participate in the study. The study generator circuitry 220 transmits the study to the selected participants 602, each of which is associated with a respective electronic device(s) 102 and/or other similar electronic devices. While three participants 602 are shown in the illustrated example of FIG. 6, the study can include less than three participants 602 (e.g., one or two) or more than three participants 602 in other examples.

The participants 602 access the study via the example data collection application circuitry 128. In some examples, the participants log into the data collection application circuitry 128 to access the study. In some examples, the study includes at least one modality 602, 604, 606 for gathering response data. For example, an example first modality 602 may include an EEG and/or an EKG, an example second modality 604 may include facial emotion encoding and/or eye-tracking, and an example third modality 606 may include response time and/or galvanic skin response data. However, the modalities 602, 604, 606 can differ in other examples.

In some examples, the example session manager circuitry 318 enables the participants to calibrate devices corresponding to each modality 602, 604, 606. When the devices are calibrated and the participant(s) are ready to begin the study, the session manager circuitry 318 plays the study script and gathers data for each modality 602, 604, 606.

Upon completion of the study, the example validation circuitry 328 performs one or more session quality checks to ensure task compliance, data integrity, hardware status, etc. Upon validation of the study, the validation circuitry 328 uploads the gathered data to remote servers such as, for example, a cloud server.

The interface circuitry 202 of the data collection circuitry 108 receives the uploaded study data. In some examples, the example feedback circuitry 218 provides feedback to the participants. In some examples, the pre-processor circuitry 222 and/or the data analyzer circuitry 226 analyzes the data to generate insights. In some examples, the example report generator circuitry 228 generates a report based on the insights.

Figure 7:
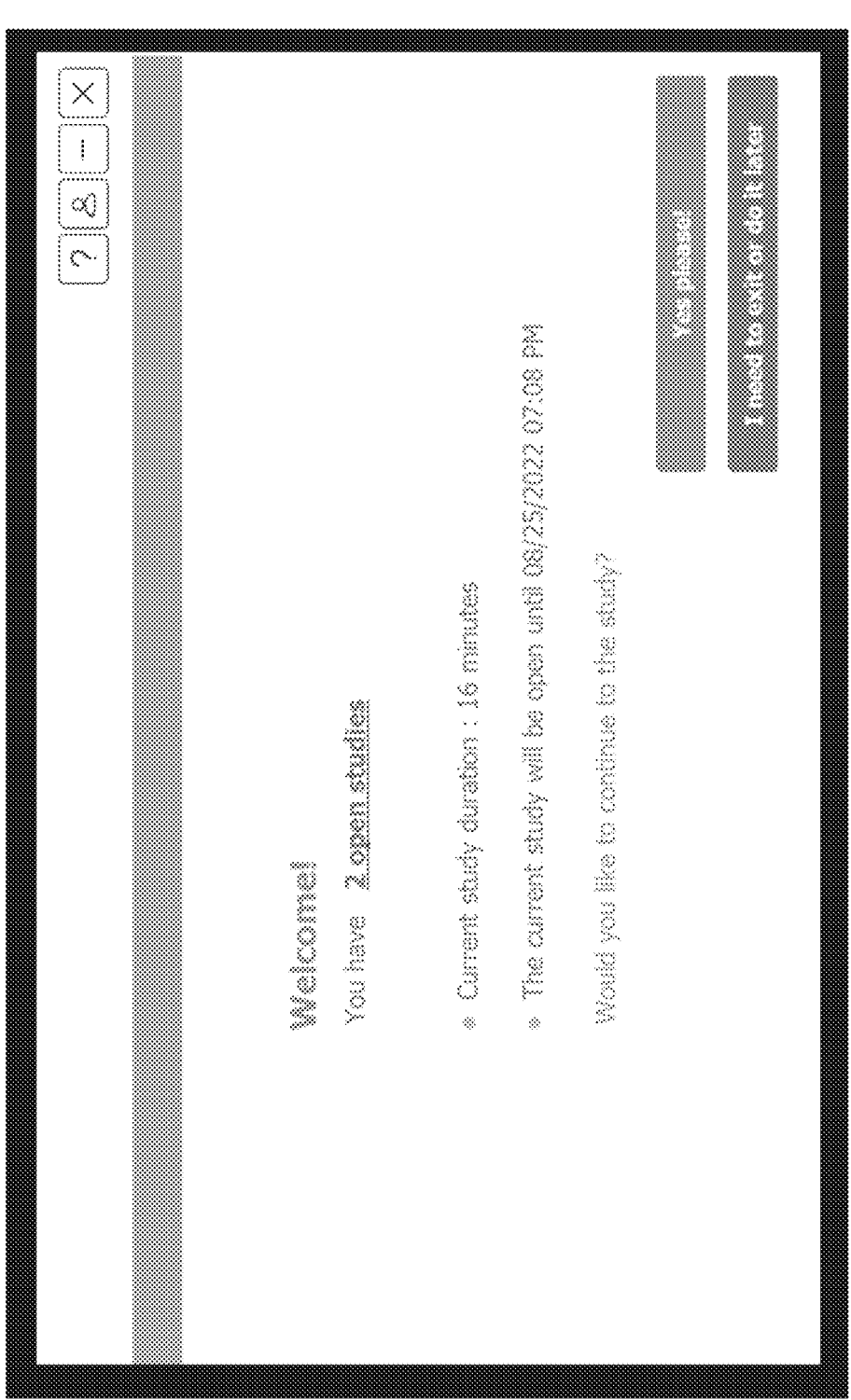
FIG. 7 illustrates an example study entrance user interface.

FIG. 7 illustrates an example study entrance user interface or screen 700 corresponding to the example data collection application circuitry of FIGS. 1, 3, and 6 in accordance with teachings of this disclosure. The study entrance screen 700 of FIG. 7 allows the participant to identify which study(ies) is available, a direction of the study, and when the study will close. The study entrance screen 700 of FIG. 7 allows to continue with the study or to exit. As illustrated in FIG. 7, the data collection application circuitry 128 allows the participant to return at a later point to complete the study a time convenient to the participant.

Figure 8:
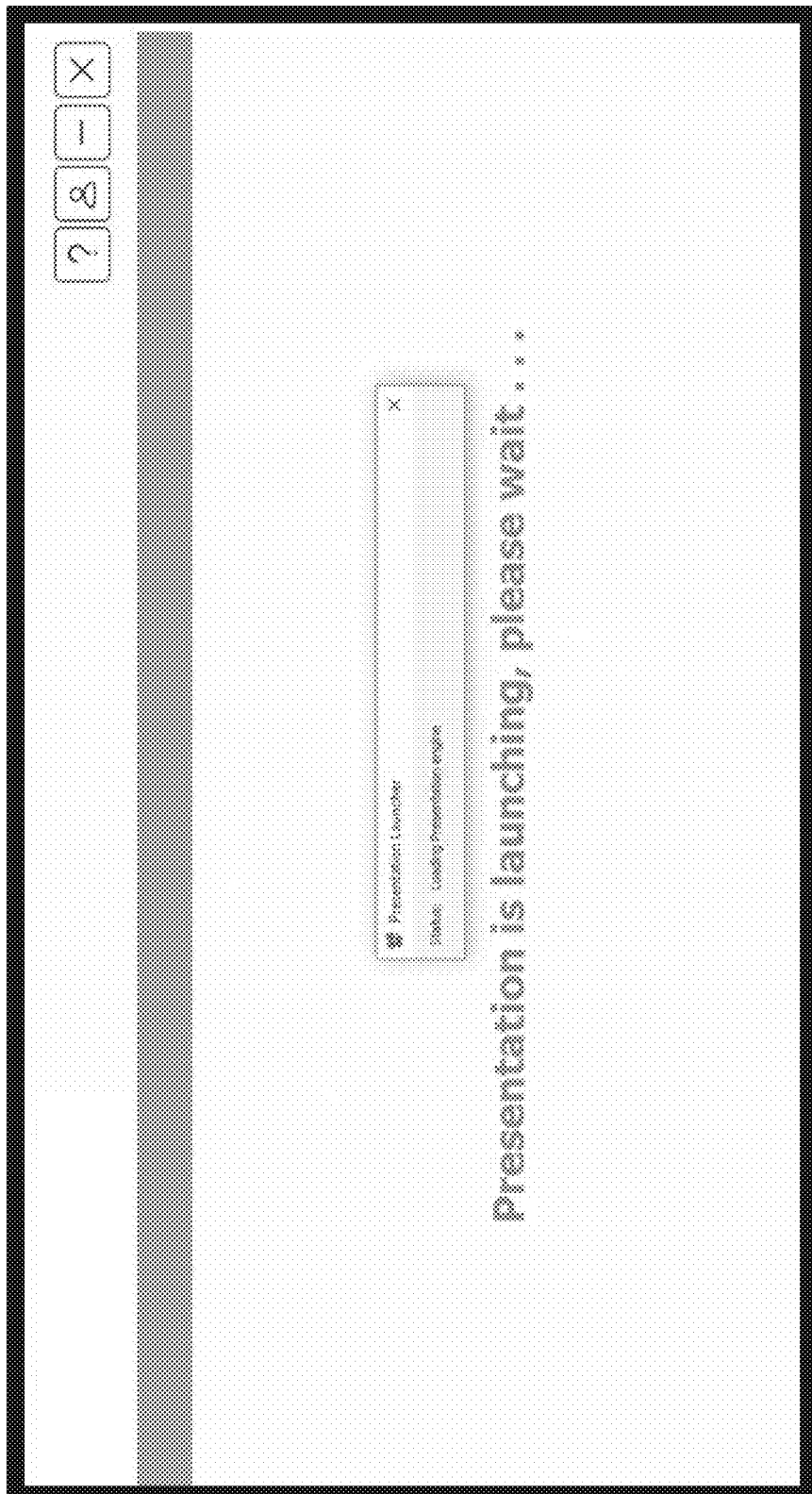
FIG. 8 illustrates an example presentation launching user interface.

FIG. 8 illustrates an example presentation launching user interface or screen 800 corresponding to the example data collection application circuitry of FIGS. 1, 3, and 6 in accordance with teachings of this disclosure. The presentation launching screen 800 may alert the participant that the example session manager circuitry 220 is preparing to launch the study.

While an example manner of implementing the data collection system 100 of FIG. 1 is illustrated in FIGS. 1-7, one or more of the elements, processes, and/or devices illustrated in FIGS. 1-7 may be combined, divided, re-arranged, omitted, eliminated, and/or implemented in any other way. Further, the example data collection circuitry 108, the example data collection application circuitry 128, and/or, more generally, the example data collection system 100 of FIGS. 1-7, may be implemented by hardware alone or by hardware in combination with software and/or firmware. Thus, for example, any of the example data collection circuitry 108, the example data collection application circuitry 128, and/or, more generally, the example data collection system 100, could be implemented by programmable circuitry in combination with machine readable instructions (e.g., firmware or software), processor circuitry, analog circuit(s), digital circuit(s), logic circuit(s), programmable processor(s), programmable microcontroller(s), GPU(s), DSP(s), ASIC(s), programmable logic device(s) (PLD(s)), and/or FPLD(s) such as FPGAs. Further still, the example data collection system 100 of FIGS. 1-7 may include one or more elements, processes, and/or devices in addition to, or instead of, those illustrated in FIGS. 1-7, and/or may include more than one of any or all of the illustrated elements, processes and devices.

Flowchart(s) representative of example machine readable instructions, which may be executed by programmable circuitry to implement and/or instantiate the data collection system 100 of FIG. FIGS. 1-7 and/or representative of example operations which may be performed by programmable circuitry to implement and/or instantiate the data collection system 100 of FIG. FIGS. 1-7, are shown in FIGS. 9-14. The machine readable instructions may be one or more executable programs or portion(s) of one or more executable programs for execution by programmable circuitry such as the programmable circuitry 1512 and/or 1612 shown in the example processor platform 1500 and/or 1622 discussed below in connection with FIGS. 15 and/or 16 and/or may be one or more function(s) or portion(s) of functions to be performed by the example programmable circuitry (e.g., an FPGA) discussed below in connection with FIGS. 17 and/or 18. In some examples, the machine readable instructions cause an operation, a task, etc., to be carried out and/or performed in an automated manner in the real world. As used herein, "automated" means without human involvement.

The program may be embodied in instructions (e.g., software and/or firmware) stored on one or more non-transitory computer readable and/or machine readable storage medium such as cache memory, a magnetic-storage device or disk (e.g., a floppy disk, a Hard Disk Drive (HDD), etc.), an optical-storage device or disk (e.g., a Blu-ray disk, a Compact Disk (CD), a Digital Versatile Disk (DVD), etc.), a Redundant Array of Independent Disks (RAID), a register, ROM, a solid-state drive (SSD), SSD memory, non-volatile memory (e.g., electrically erasable programmable read-only memory (EEPROM), flash memory, etc.), volatile memory (e.g., Random Access Memory (RAM) of any type, etc.), and/or any other storage device or storage disk. The instructions of the non-transitory computer readable and/or machine readable medium may program and/or be executed by programmable circuitry located in one or more hardware devices, but the entire program and/or parts thereof could alternatively be executed and/or instantiated by one or more hardware devices other than the programmable circuitry and/or embodied in dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a human and/or machine user) or an intermediate client hardware device gateway (e.g., a radio access network (RAN)) that may facilitate communication between a server and an endpoint client hardware device. Similarly, the non-transitory computer readable storage medium may include one or more mediums. Further, although the example program is described with reference to the flowchart(s) illustrated in FIGS. 9-14, many other methods of implementing the example data collection system 100 may alternatively be used. For example, the order of execution of the blocks of the flowchart(s) may be changed, and/or some of the blocks described may be changed, eliminated, or combined. Additionally or alternatively, any or all of the blocks of the flow chart may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The programmable circuitry may be distributed in different network locations and/or local to one or more hardware devices (e.g., a single-core processor (e.g., a single core CPU), a multi-core processor (e.g., a multi-core CPU, an XPU, etc.)). For example, the programmable circuitry may be a CPU and/or an FPGA located in the same package (e.g., the same integrated circuit (IC) package or in two or more separate housings), one or more processors in a single machine, multiple processors distributed across multiple servers of a server rack, multiple processors distributed across one or more server racks, etc., and/or any combination(s) thereof.

The machine readable instructions described herein may be stored in one or more of a compressed format, an encrypted format, a fragmented format, a compiled format, an executable format, a packaged format, etc. Machine readable instructions as described herein may be stored as data (e.g., computer-readable data, machine-readable data, one or more bits (e.g., one or more computer-readable bits, one or more machine-readable bits, etc.), a bitstream (e.g., a computer-readable bitstream, a machine-readable bitstream, etc.), etc.) or a data structure (e.g., as portion(s) of instructions, code, representations of code, etc.) that may be utilized to create, manufacture, and/or produce machine executable instructions. For example, the machine readable instructions may be fragmented and stored on one or more storage devices, disks and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of computer-executable and/or machine executable instructions that implement one or more functions and/or operations that may together form a program such as that described herein.

In another example, the machine readable instructions may be stored in a state in which they may be read by programmable circuitry, but require addition of a library (e.g., a dynamic link library (DLL)), a software development kit (SDK), an application programming interface (API), etc., in order to execute the machine-readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable, computer readable and/or machine readable media, as used herein, may include instructions and/or program(s) regardless of the particular format or state of the machine readable instructions and/or program(s).

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example operations of FIGS. 9-14 may be implemented using executable instructions (e.g., computer readable and/or machine readable instructions) stored on one or more non-transitory computer readable and/or machine readable media. As used herein, the terms non-transitory computer readable medium, non-transitory computer readable storage medium, non-transitory machine readable medium, and/or non-transitory machine readable storage medium are expressly defined to include any type of computer readable storage device and/or storage disk and to exclude propagating signals and to exclude transmission media. Examples of such non-transitory computer readable medium, non-transitory computer readable storage medium, non-transitory machine readable medium, and/or non-transitory machine readable storage medium include optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms "non-transitory computer readable storage device" and "non-transitory machine readable storage device" are defined to include any physical (mechanical, magnetic and/or electrical) hardware to retain information for a time period, but to exclude propagating signals and to exclude transmission media. Examples of non-transitory computer readable storage devices and/or non-transitory machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer-readable instructions, machine-readable instructions, etc.

FIG. 9 is a flowchart representative of example machine readable instructions and/or example operations 900 that may be executed, instantiated, and/or performed by programmable circuitry to obtain and analyze neuro-response data and/or physiological response data corresponding to a study. The example machine-readable instructions and/or the example operations 900 of FIG. 9 begin at block 902, at which the example study generator circuitry 220 generates an example study. For example, the study generator circuitry 220 facilitates the development of protocols and/or study designs for a study by allowing a selection input one or more modalities of interest for the study based on a target for the study. For example, a researcher may select EEG and eye-tracking, just EEG, just eye-tracking, etc. In some examples, the study generator circuitry 220 generates instructions that describe how to set up, connect, and calibrate a participant's data connection(s) based on the one or modalities of interest.

At block 904, the example participant recruiter circuitry 206 screens and/or selects a participant(s) for the study. For example, the participant recruiter circuitry 206 may search demographics and/or attributes desired for the study against the example panelist database 110 and/or the example onboarded participant data 217 to identify potential participants that qualify for the study. The participant recruiter circuitry 206 may select one or more potential participants and transmit the study to the participants. In some examples, the participant recruiter circuitry 206 may request confirmation of whether the participant agrees to participate in the study.

At block 906, the study generator circuitry 220 transmits the study to the selected participant(s) (e.g., via the example interface circuitry 202). For example, the data collection circuitry 108 may transmit a data packet (e.g., an example data packet(s) 308) to an example electronic device 102 associated with the participant(s) and/or an example identifier associated with the participant(s) that includes the study (e.g., instructions, marketing material(s), etc.)

At block 908, the example data collection circuitry 108 obtains study data from the participant(s) for the study (e.g., via the example interface circuitry 202). For example, during a session corresponding to the study, and/or upon completion of a session corresponding to the study (or anytime thereafter), the participant(s) (e.g., via example session manager circuitry 318 of the example data collection application circuitry 128) may transmit response data corresponding to the study to the data collection circuitry 108. In some examples, response data is transmitted through multiple communications. In some examples, the study data includes indicators of a level of completeness of the study and/or a quality of the study data.

At block 910, the example feedback circuitry 218 may provide feedback to the participant(s) (e.g., via the example interface circuitry 202). For example, the feedback circuitry 218 may transmit feedback to the participant(s) with an assessment of the session, to confirm successful upload of response data, to indicate the participant will receive less than full compensation, other feedback disclosed herein, etc.

At block 912, the feedback circuitry 218 transmits compensation and/or a confirmation thereof to the example electronic device 102 corresponding to the participant(s). For example, the participant(s) receive compensation for completing the study. The feedback circuitry 218 may transmit the compensation to the participant (e.g., via the data collection application circuitry 128, the electronic device, etc.) and/or a confirmation that the compensation will be provided to the participant.

At block 914, the example data analyzer circuitry 226 analyzes the data obtained from the participant(s). For example, the data analyzer circuitry 226 may apply techniques that blend multiple modes of neural signatures and measurement mechanisms assess the effectiveness of a marketing material(s). The data analyzer circuitry 226 may pre-process study data for each participant(s) separately. The data analyzer circuitry 226 may aggregate and unify the neurophysiological and behavior responses to provide a robust measure of engagement and predict actionable behavior. In some examples, the data analyzer circuitry 226 generates a composite output with an effectiveness of the marketing material(s).

At block 916, the example report generator circuitry 228 generates a report. For example, the report generator circuitry 228 may generate a report that includes insights based on the composite output. In some examples, the report generator circuitry 228 allows clients (e.g., of the market research entity 104) to self-serve custom insights from the composite modal outputs characterizing the effectiveness of the stimulus material. For example, the report generator circuitry 228 may allow the client to parse, audit, scrutinize, and/or otherwise study the response data, the composite output, and/or a report to generate additional or alternative insights. In some examples, the report generator circuitry 228 allows the client to generate diagnostics on a second-by-second level.

Figure 10:
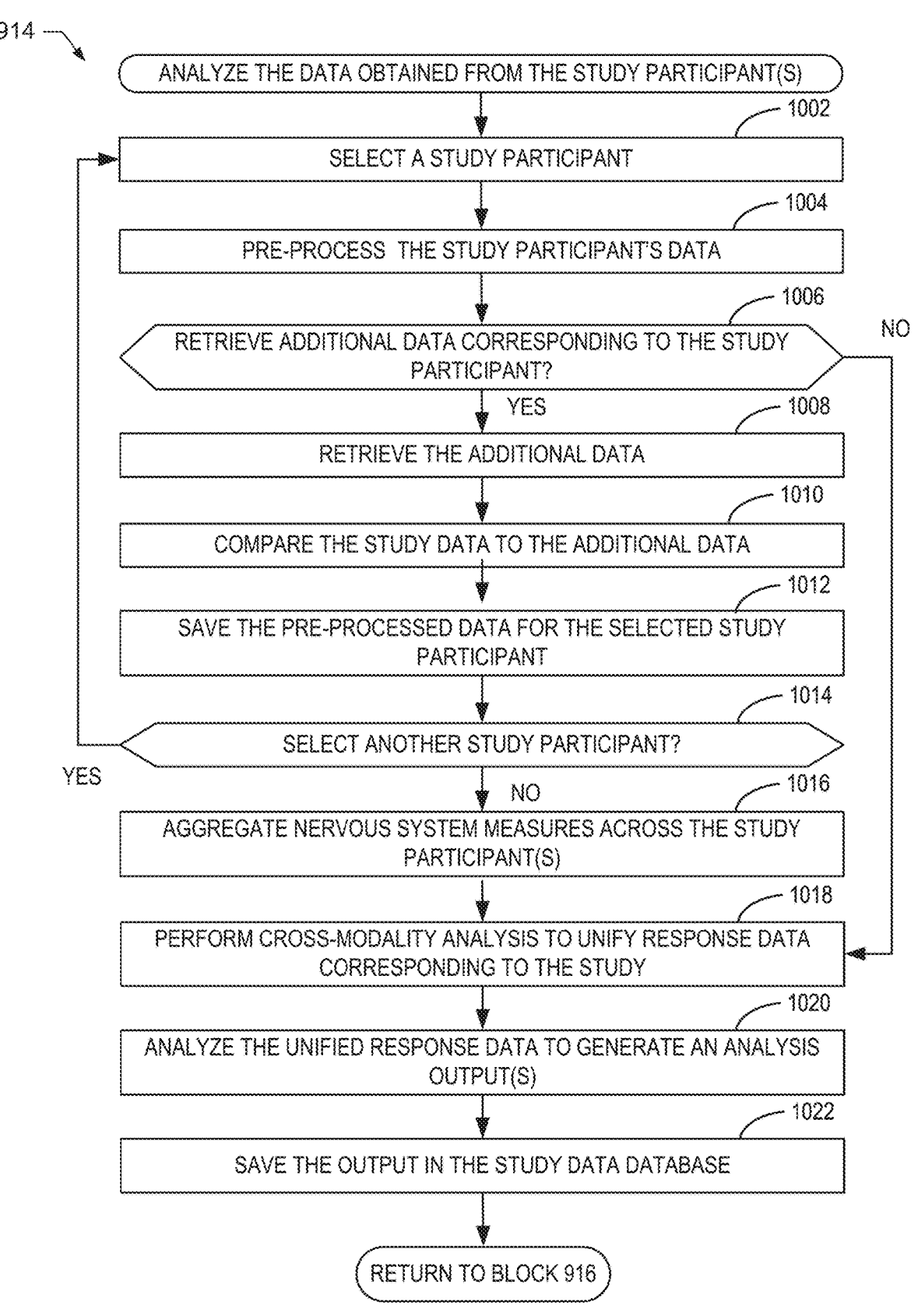

FIG. 10 is a flowchart representative of example machine readable instructions and/or example operations 914 that may be executed, instantiated, and/or performed by programmable circuitry to analyze the response data obtained from the participant(s). The machine readable instructions and/or the operations 914 of FIG. 10 begin at block 1002, at which the example data analyzer circuitry 226 retrieves study data corresponding to a participant. For example, the data analyzer circuitry 226 may retrieve study data that includes response data uploaded to the data collection circuitry 108 by the participant (e.g., via the electronic device 102).

At block 1004, the example data pre-processor circuitry 222 pre-processes the study data. For example, the data pre-processor circuitry 222 may separate the study data into regions of interest based on events of interest to identify. The data pre-processor circuitry 222 may remove certain data from the study data, such as EEG artifacts that are specific to the participant. The data pre-processor circuitry 222 may isolate data of specific interest based on the events of interest. In some examples, the data pre-processor circuitry 222 may apply uses techniques to personalize the participant's response data to generate personalized data.

At block 1006, the example data analyzer circuitry 226 determines whether to retrieve additional data for the participant. For example, the data analyzer circuitry 226 may determine to retrieve additional data corresponding to personalized data previously generated for the participant. If the answer to block 1006 is YES, control advances to block 1008, at which the data analyzer circuitry 226 retrieves the additional data (e.g., from the onboarded participant data 217). If the answer to block 1006 is NO, control advances to block 1012.

At block 1010, the data analyzer circuitry 226 compares the response data corresponding to the current study data to personalized data. For example, the data analyzer circuitry 226 may compare the response data to the personalize data to determine the data correspond to the same person. At block 1012, the data analyzer circuitry 226 saves the pre-processed study data for the participant. For example, the data analyzer circuitry 226 may save the pre-processed study data with additional pre-processed study data corresponding to other participants within a sample.

At block 1014, the data analyzer circuitry 226 determines whether to select another participant. For example, the data analyzer circuitry 226 may determine to retrieve study data corresponding to another participant if the study data for another participant in the sample has not been pre-processed. If the answer to block 1014 is YES, control returns to block 1002. If the answer to block 1014 is NO, control advances to block 1016.

At block 1016, the data analyzer circuitry 226 aggregates pre-processed study data across participants in a sample. For example, the data analyzer circuitry 226 may obtain pre-processed study data for a plurality of participants that participated in a study and are part of a sample and aggregates the data. For example, the data analyzer circuitry 226 may aggregate nervous system measurements across the participants' study sessions.

At block 1018, the data analyzer circuitry 226 performs cross-modality analysis to unify response data across the study sessions. For example, the data analyzer circuitry 226 may apply techniques that blend multiple modes of neural signatures and measurements by combining the different modalities to generate a cohesive message or diagnostic of what a marketing material solicited from the participants along a direction of the sessions. Because each modality provides an indication of a specific reaction(s), combining the modalities at, for example, a specific time can allow the data analyzer circuitry 226 to determine what response was elicited and what cause the response. For example, by identifying EEG measurements (e.g., emotional response) with eye-tracking data (e.g., to identify a region of a screen being view) at a specific time can enable the data analyzer circuitry to identify that the material rendered on that part of the screen at the specific time elicited a specific emotional response. The data analyzer circuitry 226 may unify response data across participant sessions based on unique markers and/or along a timeline of the sessions.

At block 1020, the data analyzer circuitry 226 analyzes the unified response data to generate an analysis output. For example, the data analyzer circuitry 226 may analyze the unified data to assess the effectiveness of marketing material(s). For example, the data analyzer circuitry 226 may analyze the unified neurophysiological and behavior responses to provide a robust measure of engagement and predict actionable behavior.

At block 1022, the data analyzer circuitry 226 saves the output(s) and associated data in the study data database 112. For example, the data analyzer circuitry 226 may save the output(s), the pre-processed study data, the aggregated response data in the study data database 112 to allow custom reporting by clients. In some examples, the data analyzer circuitry 226 transmits the output to the example report generator circuitry 228.

FIG. 11 is a flowchart representative of example machine readable instructions and/or example operations 1100 that may be executed, instantiated, and/or performed by programmable circuitry to facilitate participation in a study. The machine readable instructions and/or the operations 1100 of FIG. 11 begin at block 1102, at which the example data collection application circuitry 128 receives a study and/or a notification thereof via the example interface circuitry 302. For example, the study may be in the form of an example data packet(s) 308.

At block 1104, the example storage circuitry 306 downloads example study material (e.g., from the data packet(s) 308) in response to detecting a secure connection. For example, the participant(s) may log into the data collection application circuitry 128 to establish the secure connection.

At block 1106, the calibration manager circuitry 320 performs interactive calibration(s) and/or connection testing. In some examples, the calibration manager circuitry 320 renders guidance on calibration(s) of a data collection device(s) needed for the study. For example, the calibration manager circuitry 320 may facilitate interactive guidance on calibrating one or more data collection devices. The data collection device(s) may include, for example, the example EEG sensor(s) 122, the facial emotion encoder circuitry 314, the eye-tracking circuitry 316, the example EKG sensor(s) 126, the example camera(s) 118, etc.

At block 1108, the example session manager circuitry 318 determines whether the measurement device(s) are calibrated. For example, the session manager circuitry 318 may perform one or more calibration tests to determine whether the measurement devices are calibrated. If the answer to block 1108 is NO, control returns to block 1106. If the answer to block 1108 is YES, control advances to block 1110.

At block 1110, the session manager circuitry 318 initiates the example timer 120 in response to a selection to begin the study. For example, the session manager circuitry 318 may initiate the timer 120 in response to detecting the selection by the participant to begin the study.

At block 1112, the session manager circuitry 318 plays a study script corresponding to the study. The study script can include a series of stimuli, tasks that request an active response(s), image and/or word probes, instructions, etc.

At block 1114, the session manager circuitry 318 records measurements corresponding to the participant(s), synchronizing time events across different modal systems. For example, during the study, the session manager circuitry 318 records measurements from the measurement device(s), such as nervous system measurement, facial encoding measurements, eye-tracking measurements. Based on the timer 120, the session manager circuitry 318 synchronizes time events across the different modal systems. For example, the session manager circuitry 318 can synchronize an EEG measurement and a facial expression of the participant at a specific moment to determine the participant's response to the material.

At block 1116, the session manager circuitry 318 renders stimulus-related questions in response to completion of the study. For example, the study may include the stimulus-related questions, which can be survey questions. Thus, the session manager circuitry 318 enables the participant(s) to answer stimulus-related (e.g., survey) questions.

At block 1118, the example validation circuitry 328 performs a quality check(s) corresponding to the session. For example, the validation circuitry 328 may perform a series of session quality checks to ensure task compliance, data integrity, hardware status, etc.

At block 1120, the example validation circuitry 328 transmits the collected data and other data to the market research entity 104 and/or the data collection circuitry 108. For example, the validation circuitry 328 may securely upload the data to remote servers including, for example, cloud based servers of the market research entity 104.

Figure 12:
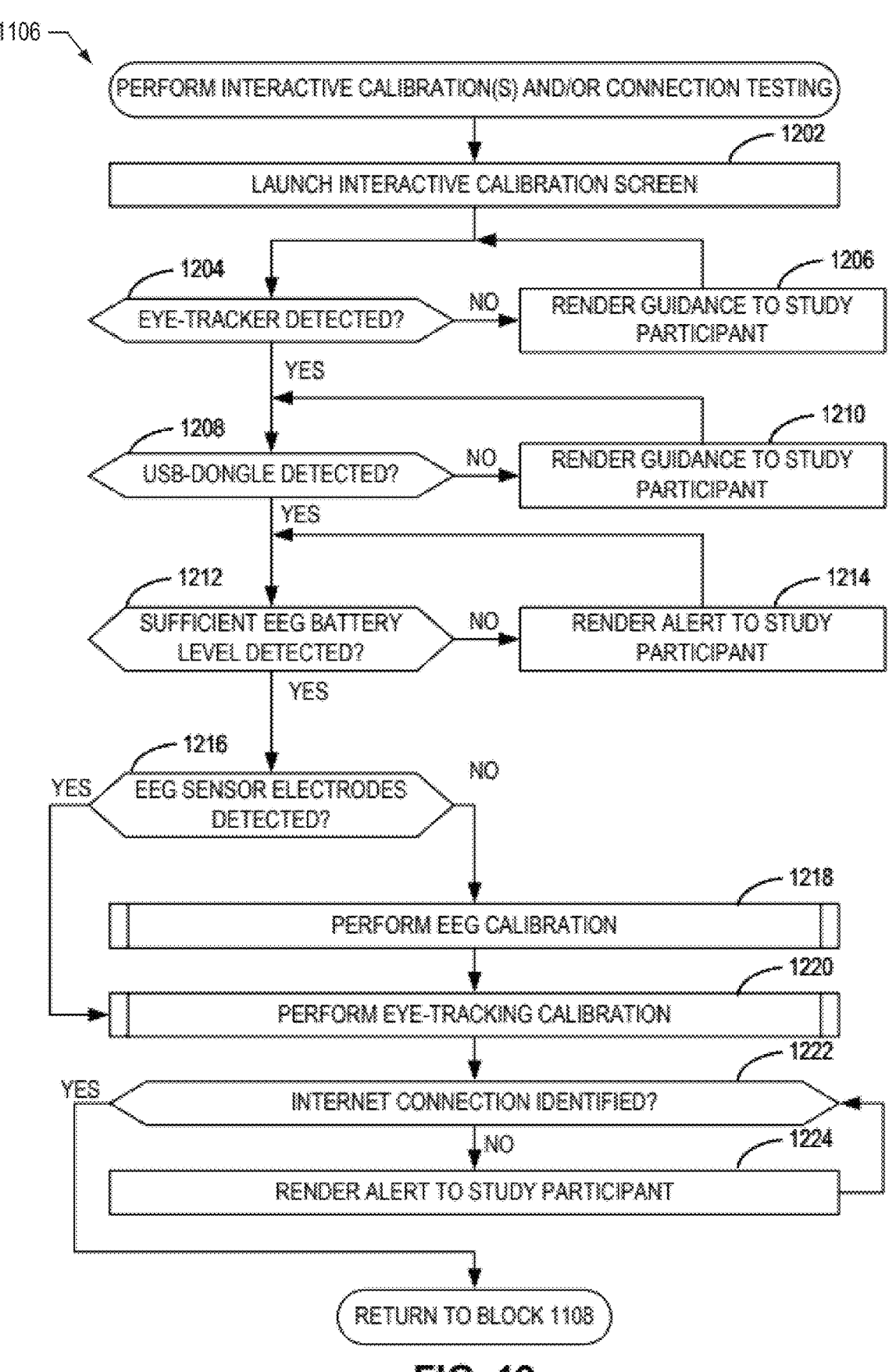

FIG. 12 is a flowchart representative of example machine readable instructions and/or example operations 1106 that may be executed, instantiated, and/or performed by programmable circuitry to facilitate interactive calibration(s) and/or connection testing. The machine readable instructions and/or the operations 1106 of FIG. 12 begin at block 1202, at which the calibration manager circuitry 320 launches an example interactive calibration screen (e.g., calibration screen 400, 500).

At block 1204, the calibration manager circuitry 320 determines whether a connection to an example eye-tracker (e.g., eye-tracking circuitry 316 of FIG. 3) is detected. If the answer to block 1204 is NO, control advances to block 1206. If the answer to block 1204 is YES, control advances to block 1208.

At block 1206, the calibration manager circuitry 320 renders guidance to the participant. For example, the calibration manager circuitry 320 may render feedback on how to connect the eye-tracking circuitry 316 with the data collection application circuitry 128 for the study.

At block 1208, the calibration manager circuitry 320 determines whether a connection to an example USB-dongle is detected. For example, the USB-dongle may be used to communicatively coupled the EEG sensor 122 to the electronic device 102. In some examples, the USB-dongle is used to feed in the EEG data from the headset. If the answer to block 1208 is NO, control advances to block 1210. If the answer to block 1208 is YES, control advances to block 1212.

At block 1210, the calibration manager circuitry 320 renders guidance to the participant. For example, the calibration manager circuitry 320 may render feedback on how to connect the USB dongle to the electronic device 102 and/or how to connect the EEG sensor 122 with the data collection application circuitry 128 for the study.

At block 1212, the calibration manager circuitry 320 determines whether sufficient EEG battery level is detected. For example, an example EEG battery level is illustrated in the calibration screen 400 of FIG. 4. In some examples, the battery level is sufficient if the battery is predicted to last longer than a direction of the study. If the answer to block 1212 is NO, control advances to block 1214. If the answer to block 1212 is YES, control advances to block 1216.

At block 1214, the calibration manager circuitry 320 renders an alert to the participant. For example, the calibration manager circuitry 320 may alert the participant that the EEG sensor 122 needs to be charged and/or connected to a power source before the participant can participate in the study. Control then returns to block 1212.

At block 1216, the calibration manager circuitry 320 determines whether example electrodes on the EEG sensor 122 are detected. For example, the calibration manager circuitry 320 may perform a check to determine whether one or more electrodes of the EEG sensor 122 can be identified by the data collection application circuitry 108. If the answer to block 1216 is NO, control advances to block 1218. If the answer to block 1216 is YES, control advances to block 1220.

At block 1218, the calibration manager circuitry 320 performs interactive EEG calibration for the EEG sensor 112.

At block 1220, the calibration manager circuitry 320 performs interactive eye-tracking calibration for the eye-tracking circuitry 316.

At block 1222, the calibration manager circuitry 320 determines whether a network connection, e.g., an internet connection is detected. For example, the calibration manager circuitry 320 may perform a check to determine whether the electronic device 102 includes a connection to an example network (e.g., network 106). If the answer to block 1222 is NO, control advances to block 1224. If the answer to block 1222 is YES, control advance to block 1108 of FIG. 11.

At block 1224, the calibration manager circuitry 320 renders an alert to the participant. For example, the calibration manager circuitry 320 may alert the participant that an internet connection is needed to complete the study and/or upload study data to the data collection circuitry 108. In the example of FIG. 12, control returns to block 1222 at which the calibration manager circuitry 320 determines whether the internet connection is detected. For example, an internet connection may be necessary to complete the study. In additional or alternative example, control may return to block 1108 to allow the participant to complete the study and upload the study data at a later time (e.g., when an internet connection is achieved).

Figure 13:
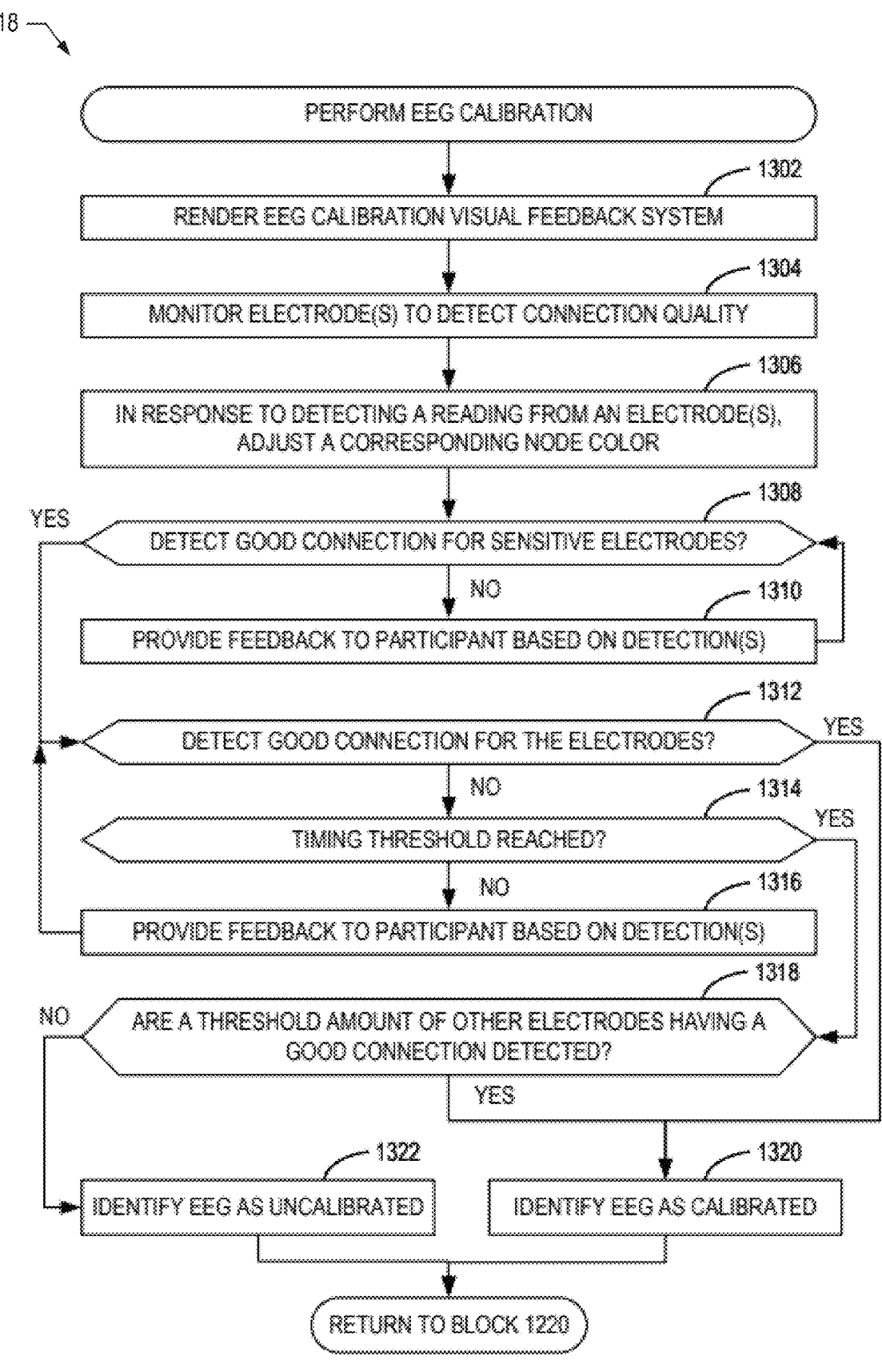

FIG. 13 is a flowchart representative of example machine readable instructions and/or example operations 1218 that may be executed, instantiated, and/or performed by programmable circuitry to facilitate EEG calibration. The machine readable instructions and/or the operations 1218 of FIG. 13 begin at block 1302, at which the calibration manager circuitry 320 renders an example EEG calibration visual feedback system (e.g., illustrated in the calibration screen 400 of FIG. 4).

At block 1304, the calibration manager circuitry 320 monitors the electrodes to detect respective connection qualities with the data collection application circuitry 128.

At block 1306, in response to detecting a reading from an electrode(s), the calibration manager circuitry 320 adjusts a corresponding node connection indication such as, for example, a node color. For example, the calibration manager circuitry 320 may detect a good quality connection with a first electrode and a surface of the head of the participant and, in response, adjust a first node connection indication corresponding to the first electrode to a first color (e.g., green) indicative of the good quality connection. If the calibration manager circuitry 320 detects a connection with a second electrode, but the quality is less than a certain (e.g., threshold) level, the calibration manager circuitry 320 may adjust a second node connection indication corresponding to the second electrode to a second color (e.g., orange) indicative of the less-than-good quality connection between the second electrode and the surface of the head of the participant. If the calibration manager circuitry 320 detects does not detect a connection with a third second electrode, the calibration manager circuitry 320 may adjust a third node connection indication corresponding to the third electrode to a third color (e.g., red) indicative of the lack of connection of the third electrode and the head of the participant.

At block 1308, the calibration manager circuitry 320 determines whether a good connection, for example sensitive electrodes is detected. For example, the EEG sensor 122 may include specific electrodes that are more important to connect than other electrodes. The calibration manager circuitry 320 may determine whether those specific electrodes have good connections before detecting connections with other, less important electrodes. If the answer to block 1308 is NO, control advances to block 1310 at which, the calibration manager circuitry 320 provides feedback to the participant based on the detection. For example, the calibration manager circuitry 320 may render guidance on connecting the sensitive electrode(s) based on a level of connection, a type of electrode pin, a type of hair of the participant, etc. Control then returns to block 1308. If the answer to block 1308 is YES, control advances to block 1312.

At block 1312, the calibration manager circuitry 320 determines whether good connections are detected for the other electrodes. If the answer to block 1312 is YES, control advances to block 1320 at which the calibration manager circuitry 320 identifies the EEG sensor 112 as calibrated. If the answer to block 1314 is NO, control advances to block 1314.

At block 1314, the calibration manager circuitry 320 determines whether a timing threshold has been reached. The timing threshold may be a threshold amount of time a participant may spend calibrating a device, such as the EEG sensor 122. If the answer to block 1314 is NO, and the timing threshold is not reached, control advances to block 1316 at which the calibration manager circuitry 320 provides feedback to the participant based on the connections detected with the other electrodes. For example, the calibration manager circuitry 320 may render guidance on connecting the other electrode(s) based on a level of connection, a type of hair of the participant, etc. If the answer to block 1316 is YES and the timing threshold is met, control advances to block 1318.

At block 1318, the calibration manager circuitry 320 determines whether a threshold amount of the other electrodes having a good connection is detected. For example, the calibration manager circuitry 320 may identify whether a specific percentage and/or ratio of electrodes have received good connections. If the answer to block 1318 is YES, control advances to block 1320 at which the calibration manager circuitry 320 identifies the EEG sensor 122 as calibrated. Thus, if the participant is able to achieve a certain (e.g., low threshold) level of connection quality, the participant may be able to continue with the study. If the answer to block 1318 is NO, control advances to block 1322, at which the calibration manager circuitry 320 identifies the EEG sensor 122 as uncalibrated. Thus, if the participant is unable to achieve a certain (e.g., low threshold) level of connection quality, the participant may not be able to continue with the study. Control returns to block 1220 of FIG. 12.

FIG. 14 is a flowchart representative of example machine readable instructions and/or example operations 1220 that may be executed, instantiated, and/or performed by programmable circuitry to facilitate eye-tracking calibration. The machine readable instructions and/or the operations 1220 of FIG. 14 begin at block 1402, at which the calibration manager circuitry 320 renders an example eye-tracking calibration visual feedback system (e.g., illustrated in the calibration screen 500 of FIG. 5).

At block 1404, the calibration manager circuitry 320 renders an example head position alignment image to perform alignment. For example, the head position alignment image may be an oval in which the participant is instructed to align a head of the participant.

At block 1406, the calibration manager circuitry 320 monitor the eye-tracking circuitry 316 to detect a user head within the alignment image.

At block 1408, the calibration manager circuitry 320 determines whether the user head is detected within the alignment image. If the answer to block 1408 is NO, control returns to block 1406 at which the calibration manager circuitry 320 continues to monitor the eye-tracking circuitry 316 to detect the user head within the alignment image.

At block 1410, the calibration manager circuitry 320 initiates an example timer 120 in response to detecting a selection to begin eye-tracker calibration.

At block 1412, the calibration manager circuitry 320 renders an example indicator to begin an eye-tracking calibration. For example, the indicator may be a color dot, a flashing dot, and/or other insignia that appears on a display screen.

At block 1414, the calibration manager circuitry 320 monitor the eye-tracking circuitry 316 to detect a user eye(s) (e.g., a user gaze) directed at the indicator(s).

At block 1416, after a duration of time, the calibration manager circuitry 320 removes the indicator. For example, the calibration manager circuitry 320 may cause the indicator to appear to explode and disappear after a number of seconds (e.g., two seconds).

At block 1418, the calibration manager circuitry 320 determines whether to render another indicator. For example, the calibration manager circuitry 320 may iterate through a plurality of indicators in an eye-tracking calibration. In some examples, the indicator(s) moves position during each presentation, causing the participant to change eye gaze to find the indicator at each iteration within the duration of time.

At block 1420, the calibration manager circuitry 320 generates and renders a score for the eye-tracking calibration. For example, the score may be a percentage of indicators at which the calibration manager circuitry 320 detected the user gaze in alignment with the respective indicator.

At block 1422, the calibration manager circuitry 320 determines whether to re-iterate the eye-tracking calibration. In some examples, the calibration manager circuitry 320 allows the participant to iterate through the eye-tracking calibration up to a certain (e.g., threshold) number of times (e.g., three iterations). If the participant completed the threshold number of iterations, the calibration manager circuitry 320 may determine not to re-iterate the eye-tracking calibration. If the participant received a perfect score, the calibration manager circuitry 220 may determine not to re-iterate the eye-tracking calibration. If the participant did not receive a perfect score and did not reach the threshold number of iterations, the calibration manager circuitry 220 may determine to re-iterate the eye-tracking calibration. If the answer to block 1422 is YES, control returns to block 1412, at which the calibration manager circuitry 320 renders another example indicator to being another eye-tracking calibration. If the answer to block 1422 is NO, control returns to block 1222 of FIG. 12.

Figure 15:
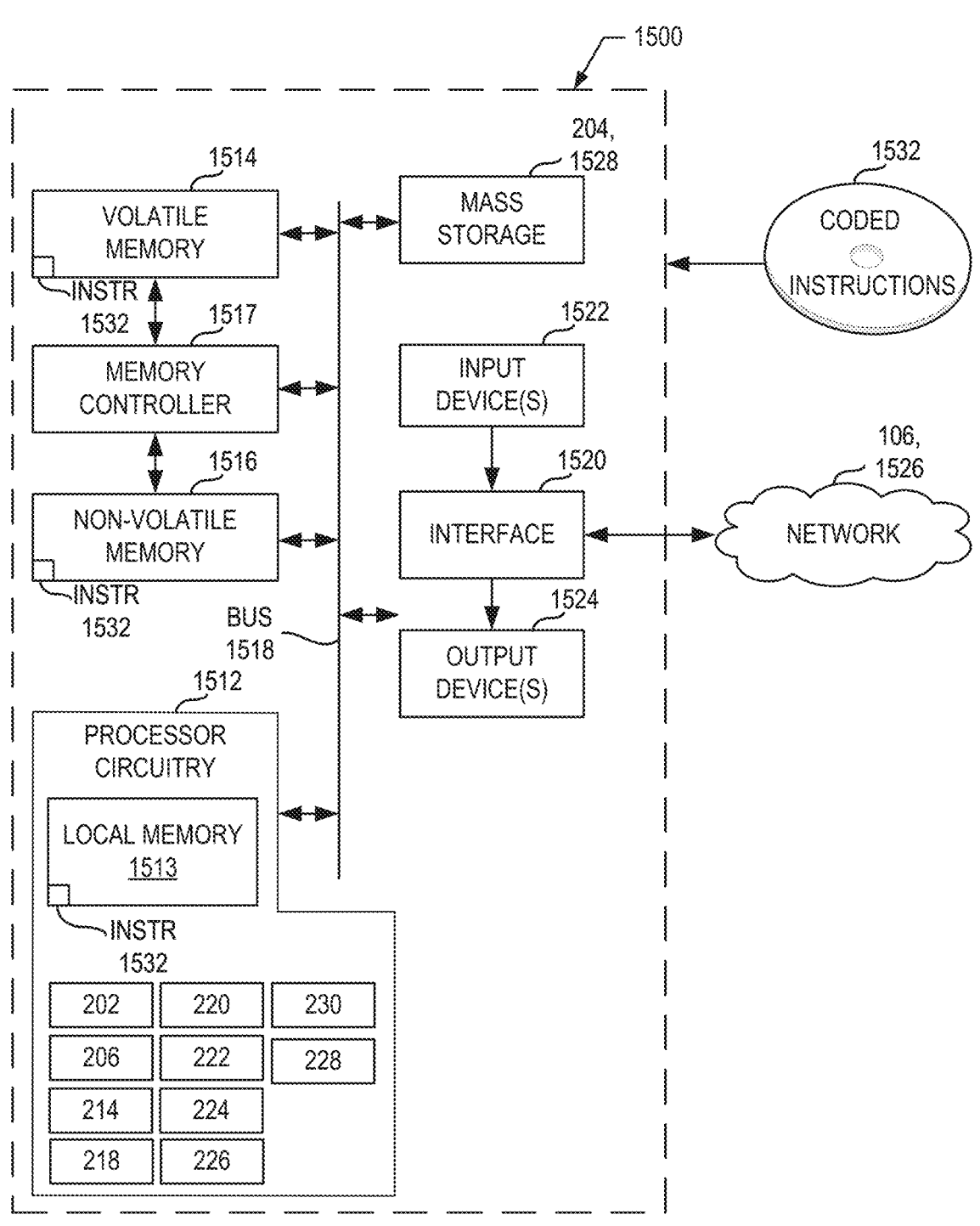
FIG. 15 is a block diagram of an example processing platform including programmable circuitry structured to execute, instantiate, and/or perform the example machine readable instructions and/or perform the example operations of FIGS. 9-10 to implement the data collection circuitry 108 of FIGS. 1-2.

FIG. 15 is a block diagram of an example programmable circuitry platform 1500 structured to execute and/or instantiate the example machine-readable instructions and/or the example operations of FIGS. 9-10 to implement the data collection circuitry 108 of FIGS. 1-2. The programmable circuitry platform 1500 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a digital video recorder, a Blu-ray player, a gaming console, a personal video recorder, a set top box, a headset (e.g., an augmented reality (AR) headset, a virtual reality (VR) headset, etc.) or other wearable device, or any other type of computing and/or electronic device.

The programmable circuitry platform 1500 of the illustrated example includes programmable circuitry 1512. The programmable circuitry 1512 of the illustrated example is hardware. For example, the programmable circuitry 1512 can be implemented by one or more integrated circuits, logic circuits, FPGAs, microprocessors, CPUs, GPUs, DSPs, and/or microcontrollers from any desired family or manufacturer. The programmable circuitry 1512 may be implemented by one or more semiconductor based (e.g., silicon based) devices. In this example, the programmable circuitry 1512 implements interface circuitry 202, participant recruiter circuitry 206, feedback circuitry 218, remote desktop interface circuitry 214, data pre-processor circuitry 222, example personalization circuitry 224, study generator circuitry 220, data analyzer circuitry 226, report generator circuitry 228, and/or custom report generator circuitry 230.

The programmable circuitry 1512 of the illustrated example includes a local memory 1513 (e.g., a cache, registers, etc.). The programmable circuitry 1512 of the illustrated example is in communication with main memory 1514, 1516, which includes a volatile memory 1514 and a non-volatile memory 1516, by a bus 1518. The volatile memory 1514 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1516 may be implemented by flash memory and/or any other desired type of memory device. Access to the main memory 1514, 1516 of the illustrated example is controlled by a memory controller 1517. In some examples, the memory controller 1517 may be implemented by one or more integrated circuits, logic circuits, microcontrollers from any desired family or manufacturer, or any other type of circuitry to manage the flow of data going to and from the main memory 1514, 1516.

The programmable circuitry platform 1500 of the illustrated example also includes interface circuitry 1520. The interface circuitry 1520 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1522 are connected to the interface circuitry 1520. The input device(s) 1522 permit(s) a user (e.g., a human user, a machine user, etc.) to enter data and/or commands into the programmable circuitry 1512. The input device(s) 1522 can be implemented by, for example, an audio sensor, a microphone, a camera (still or video), a keyboard, a button, a mouse, a touchscreen, a trackpad, a trackball, an isopoint device, and/or a voice recognition system.

One or more output devices 1524 are also connected to the interface circuitry 1520 of the illustrated example. The output device(s) 1524 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1520 of the illustrated example, thus, typically includes a graphics driver card, a graphics driver chip, and/or graphics processor circuitry such as a GPU.

The interface circuitry 1520 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1526. The communication can be by, for example, an Ethernet connection, a digital subscriber line (DSL) connection, a telephone line connection, a coaxial cable system, a satellite system, a beyond-line-of-sight wireless system, a line-of-sight wireless system, a cellular telephone system, an optical connection, etc.

The programmable circuitry platform 1500 of the illustrated example also includes one or more mass storage discs or devices 1528 to store firmware, software, and/or data. Examples of such mass storage discs or devices 1528 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 1532, which may be implemented by the machine readable instructions of FIGS. 9-10, may be stored in the mass storage device 1528, in the volatile memory 1514, in the non-volatile memory 1516, and/or on at least one non-transitory computer readable storage medium such as a CD or DVD which may be removable.

Figure 16:
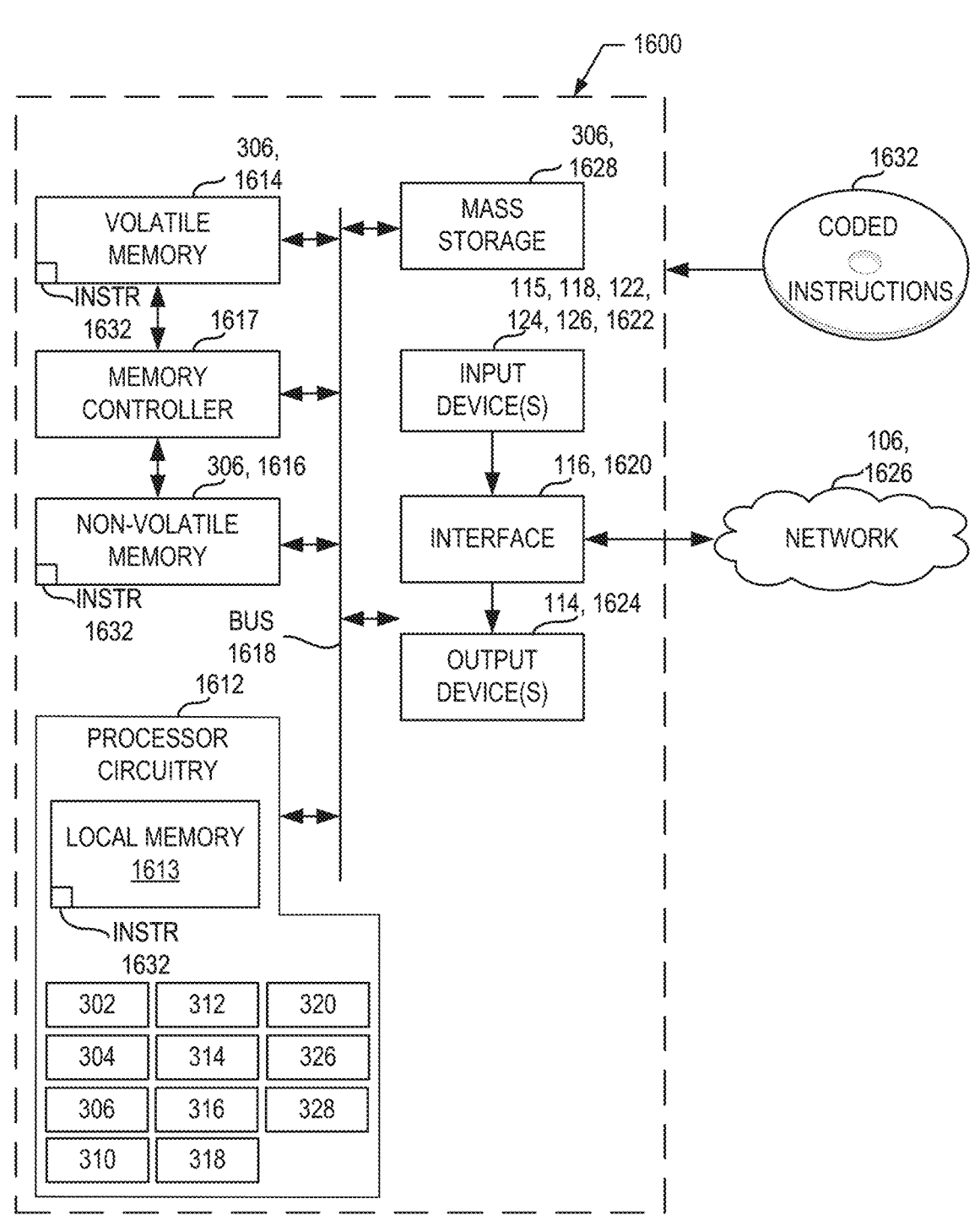
FIG. 16 is a block diagram of an example processing platform including programmable circuitry structured to execute, instantiate, and/or perform the example machine readable instructions and/or perform the example operations of FIGS. 11-14 to implement the data collection application circuitry of FIGS. 1 and 3.

FIG. 16 is a block diagram of an example programmable circuitry platform 1600 structured to execute and/or instantiate the example machine-readable instructions and/or the example operations of FIGS. 10-14 to implement the data collection application circuitry 128 of FIGS. 1 and 3. The programmable circuitry platform 1600 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a digital video recorder, a Blu-ray player, a gaming console, a personal video recorder, a set top box, a headset (e.g., an augmented reality (AR) headset, a virtual reality (VR) headset, etc.) or other wearable device, or any other type of computing and/or electronic device.

The programmable circuitry platform 1600 of the illustrated example includes programmable circuitry 1612. The programmable circuitry 1612 of the illustrated example is hardware. For example, the programmable circuitry 1612 can be implemented by one or more integrated circuits, logic circuits, FPGAs, microprocessors, CPUs, GPUs, DSPs, and/or microcontrollers from any desired family or manufacturer. The programmable circuitry 1612 may be implemented by one or more semiconductor based (e.g., silicon based) devices. In this example, the programmable circuitry 1612 implements interface circuitry 302, authenticator circuitry 304, storage circuitry 306, participant trainer circuitry 310, remote support circuitry 312, facial emotion encoder circuitry 314, eye-tracking circuitry 316, session manager circuitry 318, focus tracker circuitry 326, calibration manager circuitry 320, and/or validation circuitry 328.

The programmable circuitry 1612 of the illustrated example includes a local memory 1613 (e.g., a cache, registers, etc.). The programmable circuitry 1612 of the illustrated example is in communication with main memory 1614, 1616, which includes a volatile memory 1614 and a non-volatile memory 1616, by a bus 1618. The volatile memory 1614 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1616 may be implemented by flash memory and/or any other desired type of memory device. Access to the main memory 1614, 1616 of the illustrated example is controlled by a memory controller 1617. In some examples, the memory controller 1617 may be implemented by one or more integrated circuits, logic circuits, microcontrollers from any desired family or manufacturer, or any other type of circuitry to manage the flow of data going to and from the main memory 1614, 1616.

The programmable circuitry platform 1600 of the illustrated example also includes interface circuitry 1620. The interface circuitry 1620 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1622 are connected to the interface circuitry 1620. The input device(s) 1622 permit(s) a user (e.g., a human user, a machine user, etc.) to enter data and/or commands into the programmable circuitry 1612. The input device(s) 1622 can be implemented by, for example, an audio sensor, a microphone, a camera (still or video), a keyboard, a button, a mouse, a touchscreen, a trackpad, a trackball, an isopoint device, and/or a voice recognition system.

One or more output devices 1624 are also connected to the interface circuitry 1620 of the illustrated example. The output device(s) 1624 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1620 of the illustrated example, thus, typically includes a graphics driver card, a graphics driver chip, and/or graphics processor circuitry such as a GPU.

The interface circuitry 1620 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1626. The communication can be by, for example, an Ethernet connection, a digital subscriber line (DSL) connection, a telephone line connection, a coaxial cable system, a satellite system, a beyond-line-of-sight wireless system, a line-of-sight wireless system, a cellular telephone system, an optical connection, etc.

The programmable circuitry platform 1600 of the illustrated example also includes one or more mass storage discs or devices 1628 to store firmware, software, and/or data. Examples of such mass storage discs or devices 1628 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 1632, which may be implemented by the machine readable instructions of FIGS. 10-14, may be stored in the mass storage device 1628, in the volatile memory 1614, in the non-volatile memory 1616, and/or on at least one non-transitory computer readable storage medium such as a CD or DVD which may be removable.

Figure 17:
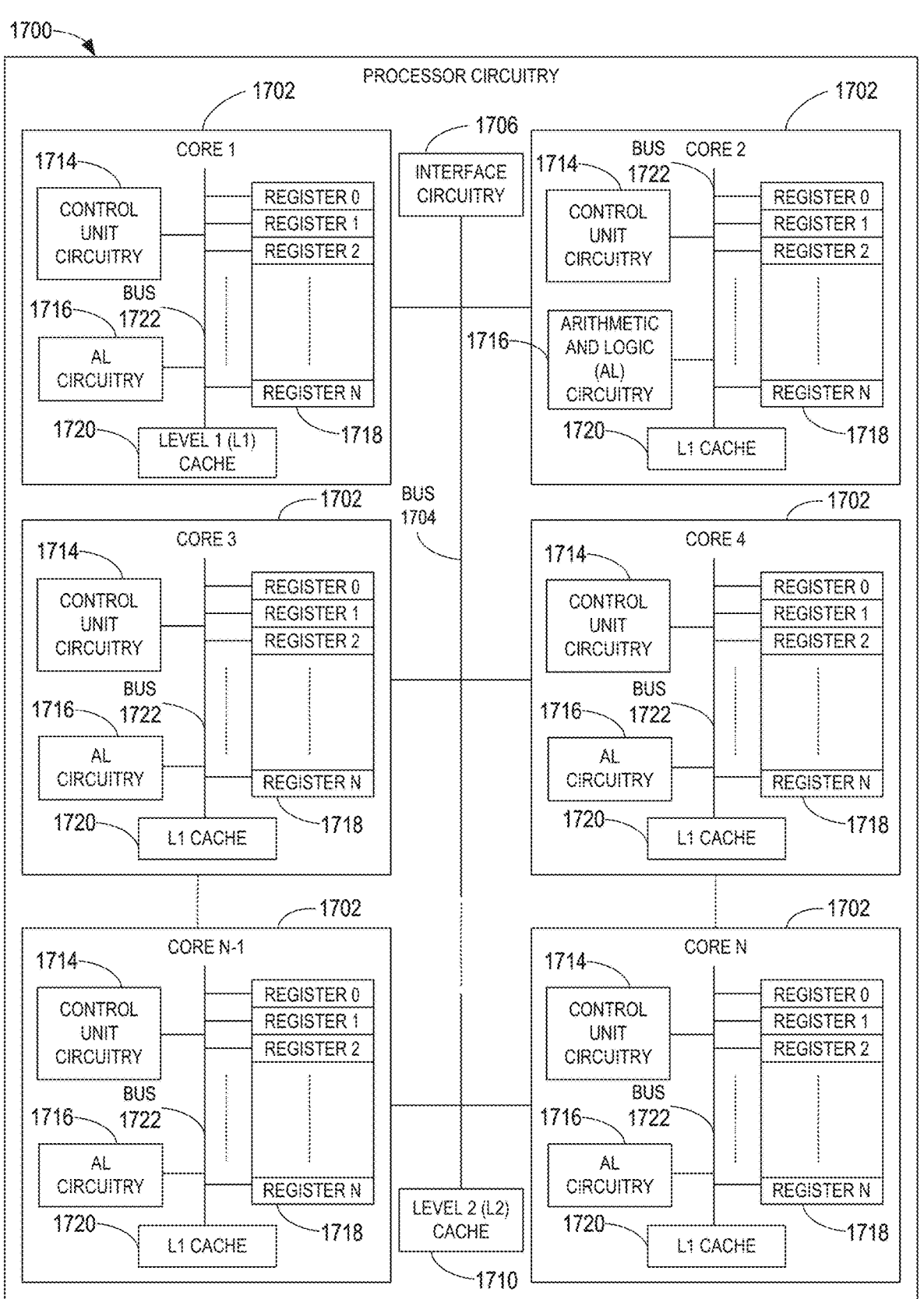
FIG. 17 is a block diagram of an example implementation of the programmable circuitry of FIG. 15 and/or FIG. 16.

FIG. 17 is a block diagram of an example implementation of the programmable circuitry 1512 of FIG. 15. In this example, the programmable circuitry 1512 of FIG. 15 is implemented by a microprocessor 1700. For example, the microprocessor 1700 may be a general-purpose micropro- cessor (e.g., general-purpose microprocessor circuitry). The microprocessor 1700 executes some or all of the machine- readable instructions of the flowcharts of FIGS. 9-10 and/or 11-14 to effectively instantiate the circuitry of FIG. 2 as logic circuits to perform operations corresponding to those machine readable instructions. In some such examples, the circuitry of FIGS. 1-3 is instantiated by the hardware circuits of the microprocessor 1700 in combination with the machine-readable instructions. For example, the micropro- cessor 1700 may be implemented by multi-core hardware circuitry such as a CPU, a DSP, a GPU, an XPU, etc. Although it may include any number of example cores 1702 (e.g., 1 core), the microprocessor 1700 of this example is a multi-core semiconductor device including N cores. The cores 1702 of the microprocessor 1700 may operate inde- pendently or may cooperate to execute machine readable instructions. For example, machine code corresponding to a firmware program, an embedded software program, or a software program may be executed by one of the cores 1702 or may be executed by multiple ones of the cores 1702 at the same or different times. In some examples, the machine code corresponding to the firmware program, the embedded soft- ware program, or the software program is split into threads and executed in parallel by two or more of the cores 1702. The software program may correspond to a portion or all of the machine readable instructions and/or operations repre- sented by the flowcharts of FIGS. 9-10 and/or 11-14.

The cores 1702 may communicate by a first example bus 1704. In some examples, the first bus 1704 may be imple- mented by a communication bus to effectuate communica- tion associated with one(s) of the cores 1702. For example, the first bus 1704 may be implemented by at least one of an Inter-Integrated Circuit (I2C) bus, a Serial Peripheral Inter- face (SPI) bus, a PCI bus, or a PCIe bus. Additionally or alternatively, the first bus 1704 may be implemented by any other type of computing or electrical bus. The cores 1702 may obtain data, instructions, and/or signals from one or more external devices by example interface circuitry 1706. The cores 1702 may output data, instructions, and/or signals to the one or more external devices by the interface circuitry 1706. Although the cores 1702 of this example include example local memory 1720 (e.g., Level 1 (L1) cache that may be split into an L1 data cache and an L1 instruction cache), the microprocessor 1700 also includes example shared memory 1710 that may be shared by the cores (e.g., Level 2 (L2 cache)) for high-speed access to data and/or instructions. Data and/or instructions may be transferred (e.g., shared) by writing to and/or reading from the shared memory 1710. The local memory 1720 of each of the cores 1702 and the shared memory 1710 may be part of a hierarchy of storage devices including multiple levels of cache memory and the main memory (e.g., the main memory 1514, 1516 of FIG. 15). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 1702 may be referred to as a CPU, DSP, GPU, etc., or any other type of hardware circuitry. Each core 1702 includes control unit circuitry 1714, arithmetic and logic (AL) circuitry (sometimes referred to as an ALU) 1716, a plurality of registers 1718, the local memory 1720, and a second example bus 1722. Other structures may be present. For example, each core 1702 may include vector unit circuitry, single instruction multiple data (SIMD) unit cir- cuitry, load/store unit (LSU) circuitry, branch/jump unit circuitry, floating-point unit (FPU) circuitry, etc. The control unit circuitry 1714 includes semiconductor-based circuits structured to control (e.g., coordinate) data movement within the corresponding core 1702. The AL circuitry 1716 includes semiconductor-based circuits structured to perform one or more mathematic and/or logic operations on the data within the corresponding core 1702. The AL circuitry 1716 of some examples performs integer based operations. In other examples, the AL circuitry 1716 also performs float- ing-point operations. In yet other examples, the AL circuitry 1716 may include first AL circuitry that performs integer- based operations and second AL circuitry that performs floating-point operations. In some examples, the AL cir- cuitry 1716 may be referred to as an Arithmetic Logic Unit (ALU).

The registers 1718 are semiconductor-based structures to store data and/or instructions such as results of one or more of the operations performed by the AL circuitry 1716 of the corresponding core 1702. For example, the registers 1718 may include vector register(s), SIMD register(s), general- purpose register(s), flag register(s), segment register(s), machine-specific register(s), instruction pointer register(s), control register(s), debug register(s), memory management register(s), machine check register(s), etc. The registers 1718 may be arranged in a bank as shown in FIG. 17. Alternatively, the registers 1718 may be organized in any other arrangement, format, or structure, such as by being distributed throughout the core 1702 to shorten access time. The second bus 1722 may be implemented by at least one of an I2C bus, a SPI bus, a PCI bus, or a PCIe bus.

Each core 1702 and/or, more generally, the microproces- sor 1700 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 1700 is a semiconduc- tor device fabricated to include many transistors intercon- nected to implement the structures described above in one or more integrated circuits (ICs) contained in one or more packages.

The microprocessor 1700 may include and/or cooperate with one or more accelerators (e.g., acceleration circuitry, hardware accelerators, etc.). In some examples, accelerators are implemented by logic circuitry to perform certain tasks more quickly and/or efficiently than can be done by a general-purpose processor. Examples of accelerators include ASICs and FPGAs such as those discussed herein. A GPU, DSP and/or other programmable device can also be an accelerator. Accelerators may be on-board the microprocessor 1700, in the same chip package as the microprocessor 1700 and/or in one or more separate packages from the microprocessor 1700.

Figure 18:
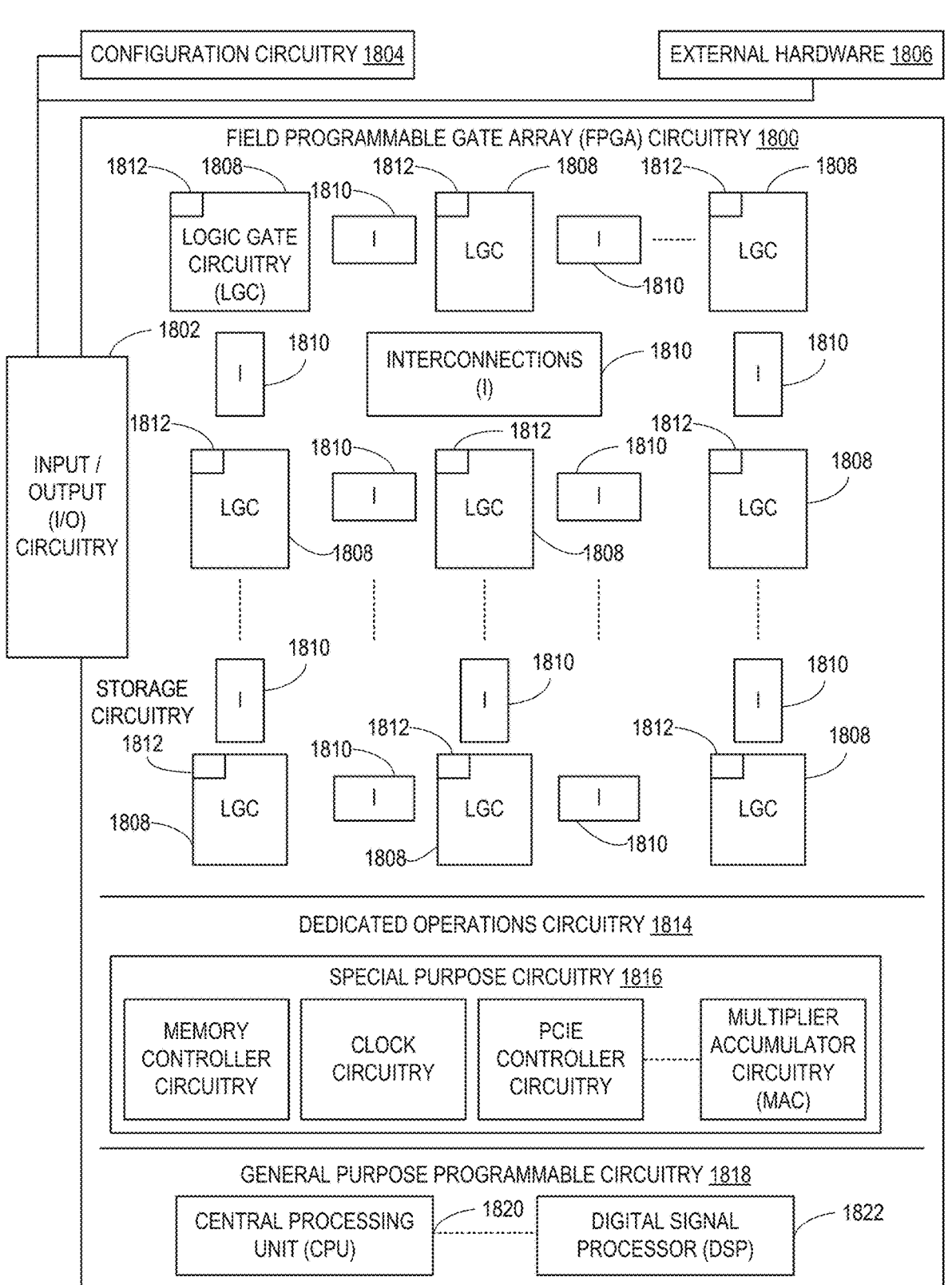
FIG. 18 is a block diagram of another example implementation of the programmable circuitry of FIG. 15 and/or FIG. 16.

FIG. 18 is a block diagram of another example implementation of the programmable circuitry 1512, 1612 of FIGS. 15 and/or 16. In this example, the programmable circuitry 1512, 1612 of FIGS. 15 and/or 16 is implemented by FPGA circuitry 1800. For example, the FPGA circuitry 1800 may be implemented by an FPGA. The FPGA circuitry 1800 can be used, for example, to perform operations that could otherwise be performed by the example microprocessor 1700 of FIG. 17 executing corresponding machine readable instructions. However, once configured, the FPGA circuitry 1800 instantiates the operations and/or functions corresponding to the machine readable instructions in hardware and, thus, can often execute the operations/functions faster than they could be performed by a general-purpose microprocessor executing the corresponding software.

More specifically, in contrast to the microprocessor 1700 of FIG. 17 described above (which is a general purpose device that may be programmed to execute some or all of the machine readable instructions represented by the flowchart(s) of FIGS. 9-10 and/or 11-14 but whose interconnections and logic circuitry are fixed once fabricated), the FPGA circuitry 1800 of the example of FIG. 18 includes interconnections and logic circuitry that may be configured, structured, programmed, and/or interconnected in different ways after fabrication to instantiate, for example, some or all of the operations/functions corresponding to the machine readable instructions represented by the flowchart(s) of FIGS. 9-10 and/or 11-14. In particular, the FPGA circuitry 1800 may be thought of as an array of logic gates, interconnections, and switches. The switches can be programmed to change how the logic gates are interconnected by the interconnections, effectively forming one or more dedicated logic circuits (unless and until the FPGA circuitry 1800 is reprogrammed). The configured logic circuits enable the logic gates to cooperate in different ways to perform different operations on data received by input circuitry. Those operations may correspond to some or all of the instructions (e.g., the software and/or firmware) represented by the flowchart(s) of FIGS. 9-10 and/or 11-14. As such, the FPGA circuitry 1800 may be configured and/or structured to effectively instantiate some or all of the operations/functions corresponding to the machine readable instructions of the flowchart(s) of FIGS. 9-10 and/or 11-14 as dedicated logic circuits to perform the operations/functions corresponding to those software instructions in a dedicated manner analogous to an ASIC. Therefore, the FPGA circuitry 1800 may perform the operations/functions corresponding to the some or all of the machine readable instructions of FIGS. 9-10 and/or 11-14 faster than the general-purpose microprocessor can execute the same.

In the example of FIG. 18, the FPGA circuitry 1800 is configured and/or structured in response to being programmed (and/or reprogrammed one or more times) based on a binary file. In some examples, the binary file may be compiled and/or generated based on instructions in a hardware description language (HDL) such as Lucid, Very High Speed Integrated Circuits (VHSIC) Hardware Description Language (VHDL), or Verilog. For example, a user (e.g., a human user, a machine user, etc.) may write code or a program corresponding to one or more operations/functions in an HDL; the code/program may be translated into a low-level language as needed; and the code/program (e.g., the code/program in the low-level language) may be converted (e.g., by a compiler, a software application, etc.) into the binary file. In some examples, the FPGA circuitry 1800 of FIG. 18 may access and/or load the binary file to cause the FPGA circuitry 1800 of FIG. 18 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1800 of FIG. 18 to cause configuration and/or structuring of the FPGA circuitry 1800 of FIG. 18, or portion(s) thereof.

In some examples, the binary file is compiled, generated, transformed, and/or otherwise output from a uniform software platform utilized to program FPGAs. For example, the uniform software platform may translate first instructions (e.g., code or a program) that correspond to one or more operations/functions in a high-level language (e.g., C, C++, Python, etc.) into second instructions that correspond to the one or more operations/functions in an HDL. In some such examples, the binary file is compiled, generated, and/or otherwise output from the uniform software platform based on the second instructions. In some examples, the FPGA circuitry 1800 of FIG. 18 may access and/or load the binary file to cause the FPGA circuitry 1800 of FIG. 18 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1800 of FIG. 18 to cause configuration and/or structuring of the FPGA circuitry 1800 of FIG. 18, or portion(s) thereof.

The FPGA circuitry 1800 of FIG. 18, includes example input/output (I/O) circuitry 1802 to obtain and/or output data to/from example configuration circuitry 1804 and/or external hardware 1806. For example, the configuration circuitry 1804 may be implemented by interface circuitry that may obtain a binary file, which may be implemented by a bit stream, data, and/or machine-readable instructions, to configure the FPGA circuitry 1800, or portion(s) thereof. In some such examples, the configuration circuitry 1804 may obtain the binary file from a user, a machine (e.g., hardware circuitry (e.g., programmable or dedicated circuitry) that may implement an Artificial Intelligence/Machine Learning (AI/ML) model to generate the binary file), etc., and/or any combination(s) thereof). In some examples, the external hardware 1806 may be implemented by external hardware circuitry. For example, the external hardware 1806 may be implemented by the microprocessor 1700 of FIG. 17.

The FPGA circuitry 1800 also includes an array of example logic gate circuitry 1808, a plurality of example configurable interconnections 1810, and example storage circuitry 1812. The logic gate circuitry 1808 and the configurable interconnections 1810 are configurable to instantiate one or more operations/functions that may correspond to at least some of the machine readable instructions of FIGS. 9-10 and/or 11-14 and/or other desired operations. The logic gate circuitry 1808 shown in FIG. 18 is fabricated in blocks or groups. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1808 to enable configuration of the electrical structures and/or the logic gates to form circuits to perform desired operations/functions. The logic gate circuitry 1808 may include other electrical structures such as look-up tables (LUTs), registers (e.g., flip-flops or latches), multiplexers, etc.

The configurable interconnections 1810 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1808 to program desired logic circuits.

The storage circuitry 1812 of the illustrated example is structured to store result(s) of the one or more of the operations performed by corresponding logic gates. The storage circuitry 1812 may be implemented by registers or the like. In the illustrated example, the storage circuitry 1812 is distributed amongst the logic gate circuitry 1808 to facilitate access and increase execution speed.

The example FPGA circuitry 1800 of FIG. 18 also includes example dedicated operations circuitry 1814. In this example, the dedicated operations circuitry 1814 includes special purpose circuitry 1816 that may be invoked to implement commonly used functions to avoid the need to program those functions in the field. Examples of such special purpose circuitry 1816 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1800 may also include example general purpose programmable circuitry 1818 such as an example CPU 1820 and/or an example DSP 1822. Other general purpose programmable circuitry 1818 may additionally or alternatively be present such as a GPU, an XPU, etc., that can be programmed to perform other operations.

Although FIGS. 17 and 18 illustrate two example implementations of the programmable circuitry 1512, 1612 of FIGS. 15 and/or 16, many other approaches are contemplated. For example, FPGA circuitry may include an on-board CPU, such as one or more of the example CPU 1820 of FIG. 17. Therefore, the programmable circuitry 1512, 1612 of FIGS. 15 and/or 16 may additionally be implemented by combining at least the example microprocessor 1700 of FIG. 17 and the example FPGA circuitry 1800 of FIG. 18. In some such hybrid examples, one or more cores 1702 of FIG. 17 may execute a first portion of the machine readable instructions represented by the flowchart(s) of FIGS. 9-10 and/or 11-14 to perform first operation(s)/function(s), the FPGA circuitry 1800 of FIG. 18 may be configured and/or structured to perform second operation(s)/function(s) corresponding to a second portion of the machine readable instructions represented by the flowcharts of FIGS. 9-10 and/or 11-14, and/or an ASIC may be configured and/or structured to perform third operation(s)/function(s) corresponding to a third portion of the machine readable instructions represented by the flowcharts of FIGS. 9-10 and/or 11-14.

It should be understood that some or all of the circuitry of FIG. 1-3 may, thus, be instantiated at the same or different times. For example, same and/or different portion(s) of the microprocessor 1700 of FIG. 17 may be programmed to execute portion(s) of machine-readable instructions at the same and/or different times. In some examples, same and/or different portion(s) of the FPGA circuitry 1800 of FIG. 18 may be configured and/or structured to perform operations/functions corresponding to portion(s) of machine-readable instructions at the same and/or different times.

In some examples, some or all of the circuitry of FIGS. 1-3 may be instantiated, for example, in one or more threads executing concurrently and/or in series. For example, the microprocessor 1700 of FIG. 17 may execute machine readable instructions in one or more threads executing concurrently and/or in series. In some examples, the FPGA circuitry 1800 of FIG. 18 may be configured and/or structured to carry out operations/functions concurrently and/or in series. Moreover, in some examples, some or all of the circuitry of FIG. 1-3 may be implemented within one or more virtual machines and/or containers executing on the microprocessor 1700 of FIG. 17.

In some examples, the programmable circuitry 1512, 1612 of FIGS. 15 and/or 16 may be in one or more packages. For example, the microprocessor 1700 of FIG. 17 and/or the FPGA circuitry 1800 of FIG. 18 may be in one or more packages. In some examples, an XPU may be implemented by the programmable circuitry 1512, 1612 of FIGS. 15 and/or 16, which may be in one or more packages. For example, the XPU may include a CPU (e.g., the microprocessor 1700 of FIG. 17, the CPU 1820 of FIG. 18, etc.) in one package, a DSP (e.g., the DSP 1822 of FIG. 18) in another package, a GPU in yet another package, and an FPGA (e.g., the FPGA circuitry 1800 of FIG. 18) in still yet another package.

Figure 19:
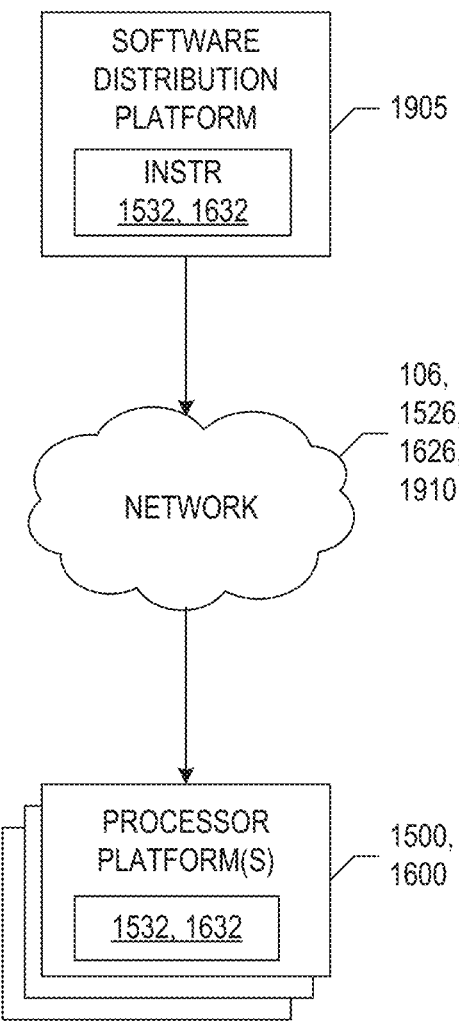
FIG. 19 is a block diagram of an example software/firmware/instructions distribution platform (e.g., one or more servers) to distribute software, instructions, and/or firmware (e.g., corresponding to the example machine readable instructions of FIGS. 9-10 and/or 11-14) to client devices associated with end users and/or consumers (e.g., for license, sale, and/or use), retailers (e.g., for sale, re-sale, license, and/or sub-license), and/or original equipment manufacturers (OEMs) (e.g., for inclusion in products to be distributed to, for example, retailers and/or to other end users such as direct buy customers).

A block diagram illustrating an example software distribution platform 1905 to distribute software such as the example machine readable instructions 1532, 1632 of FIGS. 15 and/or 16 to other hardware devices (e.g., hardware devices owned and/or operated by third parties from the owner and/or operator of the software distribution platform) is illustrated in FIG. 19. The example software distribution platform 1905 may be implemented by any computer server, data facility, cloud service, etc., capable of storing and transmitting software to other computing devices. The third parties may be customers of the entity owning and/or operating the software distribution platform 1905. For example, the entity that owns and/or operates the software distribution platform 1905 may be a developer, a seller, and/or a licensor of software such as the example machine readable instructions 1532, 1632 of FIGS. 15 and/or 16. The third parties may be consumers, users, retailers, OEMs, etc., who purchase and/or license the software for use and/or re-sale and/or sub-licensing. In the illustrated example, the software distribution platform 1905 includes one or more servers and one or more storage devices. The storage devices store the machine readable instructions 1532, 1632, which may correspond to the example machine readable instructions of FIGS. 9-10 and/or 11-14, as described above. The one or more servers of the example software distribution platform 1905 are in communication with an example network 1910, which may correspond to any one or more of the Internet and/or any of the example networks described above. In some examples, the one or more servers are responsive to requests to transmit the software to a requesting party as part of a commercial transaction. Payment for the delivery, sale, and/or license of the software may be handled by the one or more servers of the software distribution platform and/or by a third party payment entity. The servers enable purchasers and/or licensors to download the machine readable instructions 1532, 1632 from the software distribution platform 1905. For example, the software, which may correspond to the example machine readable instructions of FIGS. 9-10 and/or 11-14, may be downloaded to the example programmable circuitry platform 1500,1600, which is to execute the machine readable instructions 1532, 1632 to implement the data collection system 100. In some examples, one or more servers of the software distribution platform 1905 periodically offer, transmit, and/or force updates to the software (e.g., the example machine readable instructions 1532, 1632 of FIGS. 15 and/or 16) to ensure improvements, patches, updates, etc., are distributed and applied to the software at the end user devices. Although referred to as software above, the distributed "software" could alternatively be firmware.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities, etc., the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities, etc., the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements, or actions may be implemented by, e.g., the same entity or object. Additionally, although individual features may be included in different examples or claims, these may possibly be combined, and the inclusion in different examples or claims does not imply that a combination of features is not feasible and/or advantageous.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for case of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly within the context of the discussion (e.g., within a claim) in which the elements might, for example, otherwise share a same name.

As used herein, "approximately" and "about" modify their subjects/values to recognize the potential presence of variations that occur in real world applications. For example, "approximately" and "about" may modify dimensions that may not be exact due to manufacturing tolerances and/or other real world imperfections as will be understood by persons of ordinary skill in the art. For example, "approximately" and "about" may indicate such dimensions may be within a tolerance range of +/−10% unless otherwise specified herein.

As used herein "substantially real time" refers to occurrence in a near instantaneous manner recognizing there may be real world delays for computing time, transmission, etc. Thus, unless otherwise specified, "substantially real time" refers to real time+1 second.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "programmable circuitry" is defined to include (i) one or more special purpose electrical circuits (e.g., an ASIC) structured to perform specific operation(s) and including one or more semiconductor-based logic devices (e.g., electrical hardware implemented by one or more transistors), and/or (ii) one or more general purpose semiconductor-based electrical circuits programmable with instructions to perform specific functions(s) and/or operation(s) and including one or more semiconductor-based logic devices (e.g., electrical hardware implemented by one or more transistors). Examples of programmable circuitry include programmable microprocessors such as Central Processor Units (CPUs) that may execute first instructions to perform one or more operations and/or functions, FPGAs that may be programmed with second instructions to cause configuration and/or structuring of the FPGAs to instantiate one or more operations and/or functions corresponding to the first instructions, GPUs that may execute first instructions to perform one or more operations and/or functions, DSPs that may execute first instructions to perform one or more operations and/or functions, XPUs, Network Processing Units (NPUs) one or more microcontrollers that may execute first instructions to perform one or more operations and/or functions and/or integrated circuits such as ASICs. For example, an XPU may be implemented by a heterogeneous computing system including multiple types of programmable circuitry (e.g., one or more FPGAs, one or more CPUs, one or more GPUs, one or more NPUs, one or more DSPs, etc., and/or any combination(s) thereof), and orchestration technology (e.g., application programming interface(s) (API(s)) that may assign computing task(s) to whichever one(s) of the multiple types of programmable circuitry is/are suited and available to perform the computing task(s).

From the foregoing, it will be appreciated that example systems, methods, apparatus, and articles of manufacture have been disclosed that collect and analyze neurological data and/or physiological data measured at a remote location, providing the ability to collect neurological data from people without trained experts or human supervision. Disclosed systems, methods, apparatus, and articles of manufacture enable collection of data across geographies, demographics, and/or outside of normal operating hours. Disclosed systems, methods, apparatus, and articles of manufacture enable collection of larger amounts of data by enabling a greater amount of participants to participate in a study and/or to facilitate a larger amount of studies. Disclosed systems, methods, apparatus, and articles of manufacture improve the efficiency of using a computing device by utilizing personalized data during calibration of a data collection device(s). Disclosed systems, methods, apparatus, and articles of manufacture are accordingly directed to one or more improvement(s) in the operation of a machine such as a computer or other electronic and/or mechanical device.

Example methods, apparatus, systems, and articles of manufacture to remotely measure biological response data are disclosed herein. Further examples and combinations thereof include the following:

Example 1 includes an apparatus comprising interface circuitry, machine readable instructions, and programmable circuitry to at least one of instantiate or execute the machine readable instructions to generate a study based on one or more target modalities, transmit the study to electronic devices corresponding to study participants, obtain response data corresponding to the study, and aggregate the response data across the study participants and across the target modalities.

Example 2 includes the apparatus of example 1, wherein the programmable circuitry is to at least one of instantiate or execute the machine readable instructions to select the study participants based on attributes associated the study participants.

Example 3 includes the apparatus of example 2, wherein the attributes include at least one of demographics, purchase preferences, consumption history, or geographic data.

Example 4 includes the apparatus of example 1, wherein the target modalities include at least one electroencephalography (EEG), eye-tracking, facial emotion encoding, response time, galvanic skin response, or electrocardiograms (EKG).

Example 5 includes the apparatus of example 1, wherein the programmable circuitry is to at least one of instantiate or execute the machine readable instructions to the apparatus of example 1, wherein the programmable circuitry is to at least one of instantiate or execute the machine readable instructions to confirm completeness of the study based on the obtained response data, remove noise from the obtained response data, and separate the response data into regions of interest.

Example 6 includes the apparatus of example 1, wherein the programmable circuitry is to at least one of instantiate or execute the machine readable instructions to combine aggregated response data of two or more modalities to generate an outcome measure.

Example 7 includes the apparatus of example 6, wherein the programmable circuitry is to at least one of instantiate or execute the machine readable instructions to generate a report based on the outcome measurement.

Example 8 includes a non-transitory machine readable storage medium comprising instructions to cause programmable circuitry to at least generate a study based on one or more modalities, transmit the study to electronic devices corresponding to study participants, obtain response data corresponding to the study, and aggregate the response data across the study participants and across the modalities.

Example 9 includes the non-transitory machine readable storage medium of example 8, wherein the instructions are to cause the programmable circuitry to select the study participants based on attributes associated the study participants.

Example 10 includes the non-transitory machine readable storage medium of example 8, wherein the attributes include at least one of demographics, purchase preferences, consumption history, or geographic data.

Example 11 includes the non-transitory machine readable storage medium of example 8, wherein the target modalities include at least one electroencephalography (EEG), eye-tracking, facial emotion encoding, response time, galvanic skin response, or electrocardiograms (EKG).

Example 12 includes the non-transitory machine readable storage medium of example 8, wherein the instructions are to cause the programmable circuitry to confirm completeness of the study based on the obtained response data, remove noise from the obtained response data, and separate the response data into regions of interest.

Example 13 includes the non-transitory machine readable storage medium of example 8, wherein the programmable circuitry is to at least one of instantiate or execute the machine readable instructions to combine aggregated response data of two or more modalities to generate an outcome measure.

Example 14 includes the non-transitory machine readable storage medium of example 13, wherein the instructions are to cause the programmable circuitry to generate a report based on the outcome measurement.

Example 15 includes a method comprising generating, by executing an instruction with programmable circuitry, a study based on one or more target modalities, transmitting, by executing an instruction with programmable circuitry, the study to electronic devices corresponding to study participants, obtain response data corresponding to the study, and aggregating, by executing an instruction with programmable circuitry, the response data across the study participants and across the target modalities.

Example 16 includes the method of example 15, further including selecting the study participants based on attributes associated the study participants.

Example 17 includes the method of example 15, wherein the attributes include at least one of demographics, purchase preferences, consumption history, or geographic data.

Example 18 includes the method of example 15, wherein the target modalities include at least one electroencephalography (EEG), eye-tracking, facial emotion encoding, response time, galvanic skin response, or electrocardiograms (EKG).

Example 19 includes the method of example 15, further including confirming completeness of the study based on the obtained response data, removing noise from the obtained response data, and separating the response data into regions of interest.

Example 20 includes the method of example 15, further including combining aggregated response data of two or more modalities to generate an outcome measure.

Example 21 includes the method of example 20, further including generating a report based on the outcome measure.

Example 22 includes an apparatus comprising interface circuitry, machine readable instructions, and programmable circuitry to at least one of instantiate or execute the machine readable instructions to detect and analyze a study data packet, identify a measurement device to be calibrated based on the study data packet, when the measurement device is calibrated, render a study corresponding to the study data packet, the study to include a material of interest, record measurements corresponding to the study using the calibrated measurement device, and store the recorded measurements in a data file.

Example 23 includes the apparatus of example 22, wherein the material of interest includes at least one of a video, an image, a product, a word, or an advertisement.

Example 24 includes the apparatus of example 22, wherein the programmable circuitry is to at least one of instantiate or execute the machine readable instructions to render the study by displaying a script corresponding to the study.

Example 25 includes the apparatus of example 22, wherein the programmable circuitry is to at least one of instantiate or execute the machine readable instructions to generate timestamps during the study, the timestamps to be associated with respective ones of the recorded measurements.

Example 26 includes the apparatus of example 22, wherein the programmable circuitry is to at least one of instantiate or execute the machine readable instructions to monitor a participant of the study during execution of the study based on eye-tracking data.

Example 27 includes the apparatus of example 22, wherein the programmable circuitry is to at least one of instantiate or execute the machine readable instructions to analyze the data file to determine a level of completeness of the study.

Example 28 includes the apparatus of example 22, wherein the programmable circuitry is to at least one of instantiate or execute the machine readable instructions to transmit the data file to an electronic device.

Example 29 includes a non-transitory machine readable storage medium comprising instructions to cause programmable circuitry to at least detect and analyze a study data packet, identify a measurement device to be calibrated based on the study data packet, when the measurement device is calibrated, render a study corresponding to the study data packet, the study to include a material of interest, record measurements corresponding to the study using the calibrated measurement device, and store the recorded measurements in a data file.

Example 30 includes the non-transitory machine readable storage medium of example 29, wherein the material of interest includes at least one of a video, an image, a product, a word, or an advertisement.

Example 31 includes the non-transitory machine readable storage medium of example 29, wherein the instructions are to cause the programmable circuitry to render the study by displaying a script corresponding to the study.

Example 32 includes the non-transitory machine readable storage medium of example 29, wherein the instructions are to cause the programmable circuitry to generate timestamps during the study, the timestamps to be associated with respective ones of the recorded measurements.

Example 33 includes the non-transitory machine readable storage medium of example 29, wherein the instructions are to cause the programmable circuitry to monitor a participant of the study during execution of the study based on eye-tracking data.

Example 34 includes the non-transitory machine readable storage medium of example 29, wherein the instructions are to cause the programmable circuitry to analyze the data file to determine a level of completeness of the study.

Example 35 includes the non-transitory machine readable storage medium of example 29, wherein the instructions are to cause the programmable circuitry to transmit the data file to an electronic device.

Example 36 includes a method comprising detecting and analyzing, by executing at least one instruction with programmable circuitry, a study data packet, identifying a measurement device to be calibrated based on the study data packet, when the measurement device is calibrated, rendering a study corresponding to the study data packet, the study to include a material of interest, recording measurements corresponding to the study using the calibrated measurement device, and storing the recorded measurements in a data file.

Example 37 includes the method of example 36, wherein the material of interest includes at least one of a video, an image, a product, a word, or an advertisement.

Example 38 includes the method of example 36, wherein the rendering of the study includes displaying a script corresponding to the study.

Example 39 includes the method of example 36, further including generating timestamps during the study, the timestamps to be associated with respective ones of the recorded measurements.

Example 40 includes the method of example 36, further including monitoring a participant of the study during execution of the study based on eye-tracking data.

Example 41 includes the method of example 36, further including analyzing the data file to determine a level of completeness of the study.

Example 42 includes the method of example 36, further including transmitting the data file to an electronic device.

Example 43 includes One or more servers at a first location to distribute first instructions and second instructions on a network, the one or more servers comprising at least one storage device including third instructions, and programmable circuitry to execute the third instructions to transmit the first instructions over the network to a second location and the second instructions over the network to a third location, the first instructions, when executed, cause a first device operated by a first person to at least identify a first measurement device to be calibrated, instruct the first person to calibrate the first measurement device, when the first measurement device is calibrated, render a study to the first person, the study to include a material of interest, record first measurements of a first biological response of the first person to the study using the calibrated first measurement device, and transmit the recorded first measurements in a data file to a conductor of the study, the second instructions, when executed, cause a second device operated by a second person to at least identify a second measurement device to be calibrated, instruct the second person to calibrate the second measurement device, when the second measurement device is calibrated, render the study to the second person, record second measurements of a second biological response of the second person to the study using the calibrated second measurement device, and transmit the recorded second measurements in a data file to the conductor.

Example 44 includes the one or more servers of example 43, wherein the first person is a first patient, the second location is a first home, the second person is a second patient, the third location is a second home, and the conductor is a healthcare provider.

Example 45 includes the one or more servers of example 43, wherein the second location is a first home, the third location is a second home, and the material of interest is an advertisement or entertainment.

Example 46 includes the one or more servers of example 45, wherein the first instructions timestamp the first measurements and the second instructions timestamp the second measurements and third instructions are to transmit fourth instructions over the network to a fourth location, fourth instructions, when executed, align the first measurements and the second measurements and determine an aggregate response to the material of interest based on the aligned first measurements and second measurements.

The following claims are hereby incorporated into this Detailed Description by this reference. Although certain example systems, apparatus, articles of manufacture, and methods have been disclosed herein, the scope of coverage of this patent is not limited thereto. On the contrary, this patent covers all systems, apparatus, articles of manufacture, and methods fairly falling within the scope of the claims of this patent.

What is claimed is:

1. An apparatus comprising:
interface circuitry;
machine readable instructions; and
at least one programmable circuit to at least one of instantiate or execute the machine readable instructions to:
generate a study based at least on electroencephalography (EEG) and eye-tracking;
cause transmission of the study to electronic devices corresponding to study participants;
provide personalized calibration settings and an interactive calibration visual to at least one of the study participants to calibrate an EEG measurement device and an eye tracking device, the interactive calibration visual including:
a first visual indication of when nodes of the EEG measurement device have electrical connectivity that satisfies a threshold, and
a second visual indication to align a study participant relative to a display to calibrate the eye tracking device;
after the EEG measurement device and the eye tracking device are calibrated, cause presentation of the study;
obtain response data corresponding to the study; and
aggregate the response data from the EEG measurement device and the eye tracking device across the study participants.

2. The apparatus of claim 1, wherein one or more of the at least one programmable circuit is to select the study participants based on attributes associated with the study participants.

3. The apparatus of claim 2, wherein the attributes include at least one of demographics, purchase preferences, consumption history, or geographic data.

4. The apparatus of claim 1, wherein the study is based on at least one of facial emotion encoding, response time, galvanic skin response, or electrocardiograms (EKG).

5. The apparatus of claim 1, wherein one or more of the at least one programmable circuit to:
identify presentation of video during the study for a threshold amount of time;
confirm completeness of the study based on the obtained response data and the presentation of video for at least the threshold amount of time;
remove noise from the obtained response data; and
separate the response data into regions of interest.

6. The apparatus of claim 1, wherein one or more of the at least one programmable circuit is to combine aggregated response data of two or more data collection modalities to generate an outcome measure.

7. The apparatus of claim 6, wherein one or more of the at least one programmable circuit is to generate a report based on the outcome measurement.

8. The apparatus of claim 1, wherein the personalized calibration settings are based on calibration from a prior study session with the respective study participant.

9. A non-transitory machine readable storage medium comprising instructions to cause at least one programmable circuit to at least:
generate a study based at least on data collected via electroencephalography (EEG) and data collected via eye-tracking;
cause transmission of the study and an interactive calibration visual to electronic devices corresponding to study participants, the interactive calibration visual to direct calibration of an EEG measurement device and an eye tracking device, the interactive calibration visual including:
a first visual indication of when nodes of the EEG measurement device have electrical connectivity that satisfies a threshold, and
a second visual indication to align a study participant relative to a display for calibrating the eye tracking device;
after the EEG measurement device and the eye tracking device are calibrated, cause presentation of the study;
collect response data corresponding to the study via the EEG measurement device and the eye tracking device; and
aggregate the response data from the EEG measurement device and the eye tracking device across the study participants.

10. The non-transitory machine readable storage medium of claim 9, wherein the instructions are to cause one or more of the at least one programmable circuit to select the study participants based on attributes associated the study participants.

11. The non-transitory machine readable storage medium of claim 9, wherein the attributes include at least one of demographics, purchase preferences, consumption history, or geographic data.

12. The non-transitory machine readable storage medium of claim 9, wherein the study is based on at least one of facial emotion encoding, response time, galvanic skin response, or electrocardiograms (EKG).

13. The non-transitory machine readable storage medium of claim 9, wherein the instructions are to cause at least one of the at least one programmable circuit to:
identify presentation of a sequence of logos during the study;
confirm completeness of the study based on the obtained response data and the presentation of the sequence of logos;
remove noise from the obtained response data; and
separate the response data into regions of interest.

14. The non-transitory machine readable storage medium of claim 9, wherein the instructions are to cause at least one of the at least one programmable circuit to combine aggregated response data of two or more modalities to generate an outcome measure.

15. The non-transitory machine readable storage medium of claim 14, wherein the instructions are to cause at least one of the at least one programmable circuit to generate a report based on the outcome measurement.

\* \* \* \* \*